United States Patent [19]
Sarrine et al.

[11] Patent Number: 5,460,709
[45] Date of Patent: Oct. 24, 1995

[54] AUTOMATIC ELECTROPHORESIS METHOD AND APPARATUS

[75] Inventors: Robert J. Sarrine, Beaumont; Henry A. Garsee, Kountze; Charles D. Kelley, Beaumont; Michael T. Everitt, Beaumont; Earl W. Boone, Beaumont; Philip A. Guadagno, Vidor; Eric H. Petersen; Tipton L. Golias, both of Beaumont, all of Tex.

[73] Assignee: Helena Laboratories Corporation, Beaumont, Tex.

[21] Appl. No.: 124,502

[22] Filed: Sep. 21, 1993

Related U.S. Application Data

[63] Continuation-in-part of Ser. No. 79,378, Jun. 21, 1993, abandoned.

[51] Int. Cl.$^6$ .......................... G01N 27/26; G01N 27/447
[52] U.S. Cl. ...................................... 204/299 R; 204/182.8
[58] Field of Search ........................... 204/182.8, 299 R; 356/344

[56] References Cited

U.S. PATENT DOCUMENTS

| | | | |
|---|---|---|---|
| 4,130,824 | 12/1978 | Amos et al. | 356/344 X |
| 4,298,796 | 11/1981 | Warner et al. | 250/328 |
| 4,360,418 | 11/1982 | Golias | 204/299 R |
| 4,391,689 | 7/1983 | Golias | 204/299 R X |
| 4,781,464 | 11/1988 | Allington et al. | 356/419 |
| 4,810,348 | 3/1989 | Sarrine et al. | 204/299 R |
| 4,827,780 | 5/1989 | Sarrine et al. | 204/289 R X |
| 4,890,247 | 12/1989 | Sarrine et al. | 204/182.8 X |
| 4,909,920 | 3/1990 | Sarrine et al. | 204/299 R |
| 4,938,080 | 7/1990 | Sarrine et al. | 204/299 R |
| 4,954,237 | 9/1990 | Sarrine et al. | 204/299 R |
| 4,960,999 | 10/1990 | McKean et al. | 204/299 R X |

Primary Examiner—John Niebling
Assistant Examiner—John S. Starsiak, Jr.
Attorney, Agent, or Firm—Spencer, Frank & Schneider

[57] ABSTRACT

An electrophoresis apparatus for automatically performing medical assays includes an electrophoresis platform which cooperates with a gantry assembly. The electrophoresis platform and the gantry assembly are movable along paths that are perpendicular to each other. An applicator assembly includes pipettes which transfer fluid samples from a specimen tray to an electrophoresis plate mounted on the electrophoresis platform. The electrophoresis platform then moves to a position into the gantry assembly, where electrophoresis is conducted to separate the samples into different fractions. The electrophoresis platform then moves beneath a reagent pouring station where a reagent is applied to make the separated fractions fluoresce under ultraviolet light. The electrophoresis platform is then moved beneath the gantry assembly again, and an air knife in the gantry assembly spreads the reagent. After incubation and drying of the electrophoresis plate, the electrophoresis platform and gantry assembly are moved relative to one another while the electrophoresis plate is read with the aid of ultraviolet lamps and a photomultiplier tube mounted in the gantry assembly. The gain of the photomultiplier tube is automatically adjusted and the data gathered is automatically edited to remove background noise. The edited results can be printed or displayed on a video monitor. Techniques for calibrating the electrophoresis apparatus are also disclosed.

19 Claims, 38 Drawing Sheets

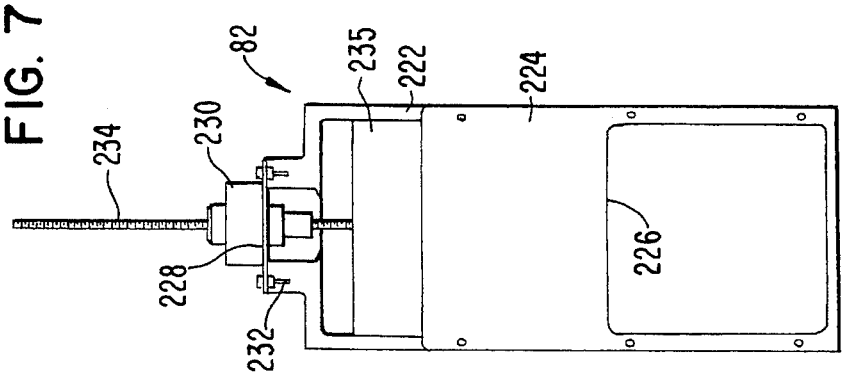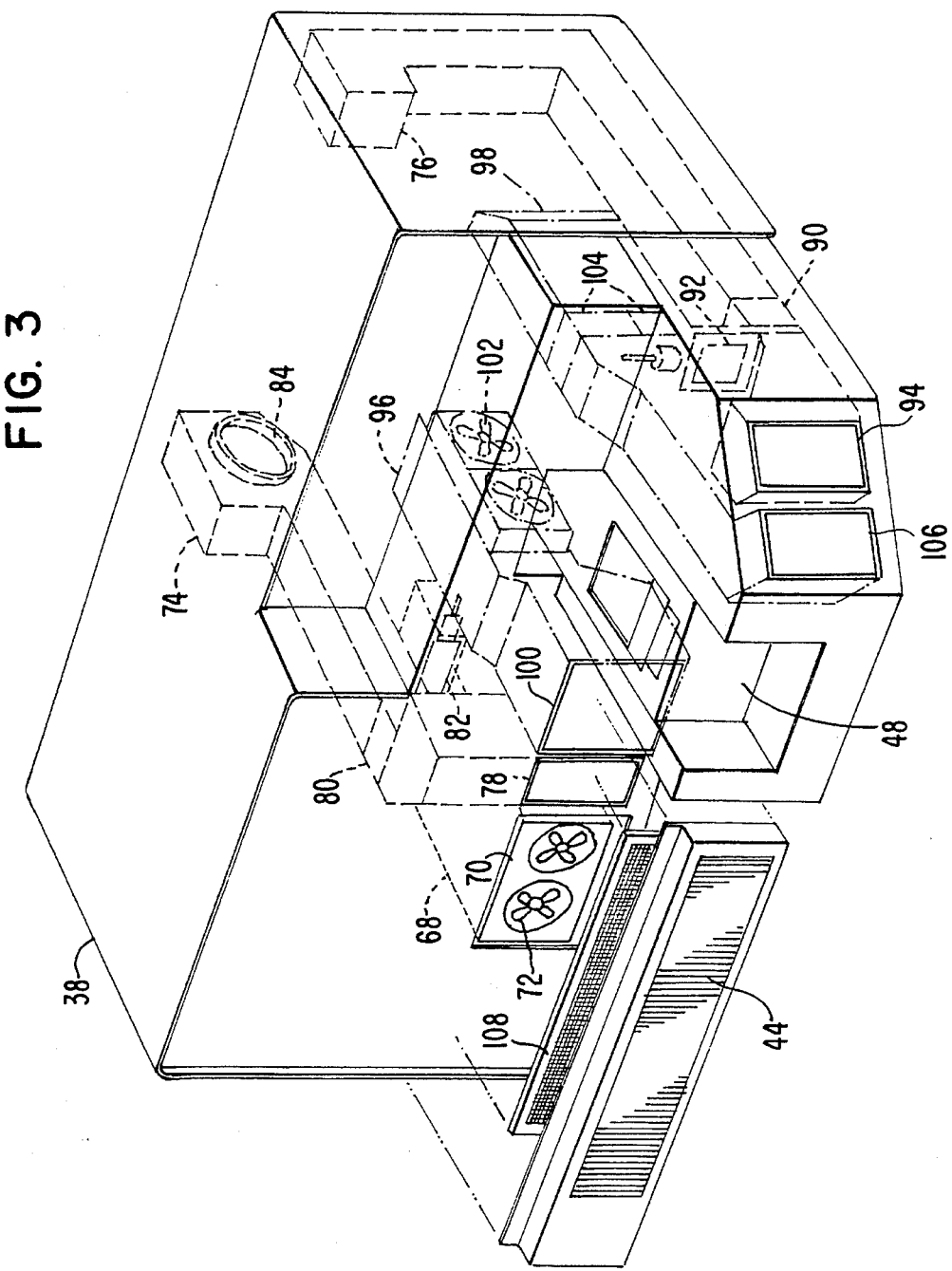

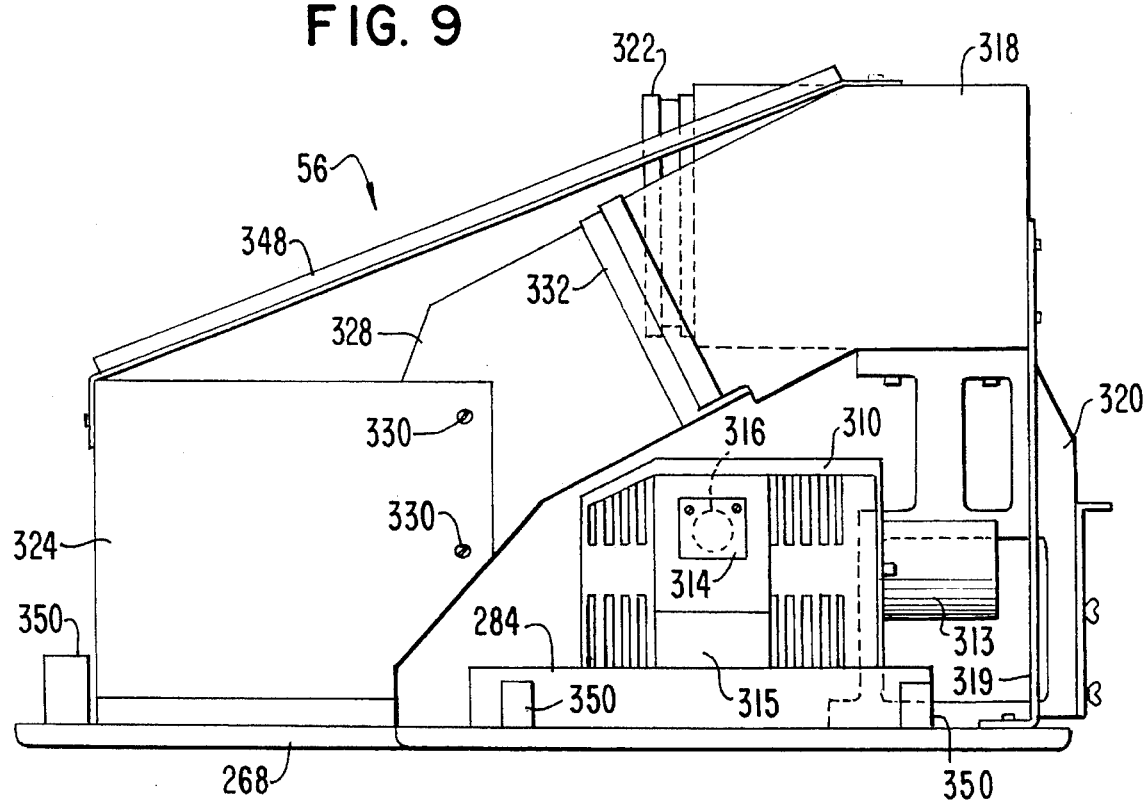
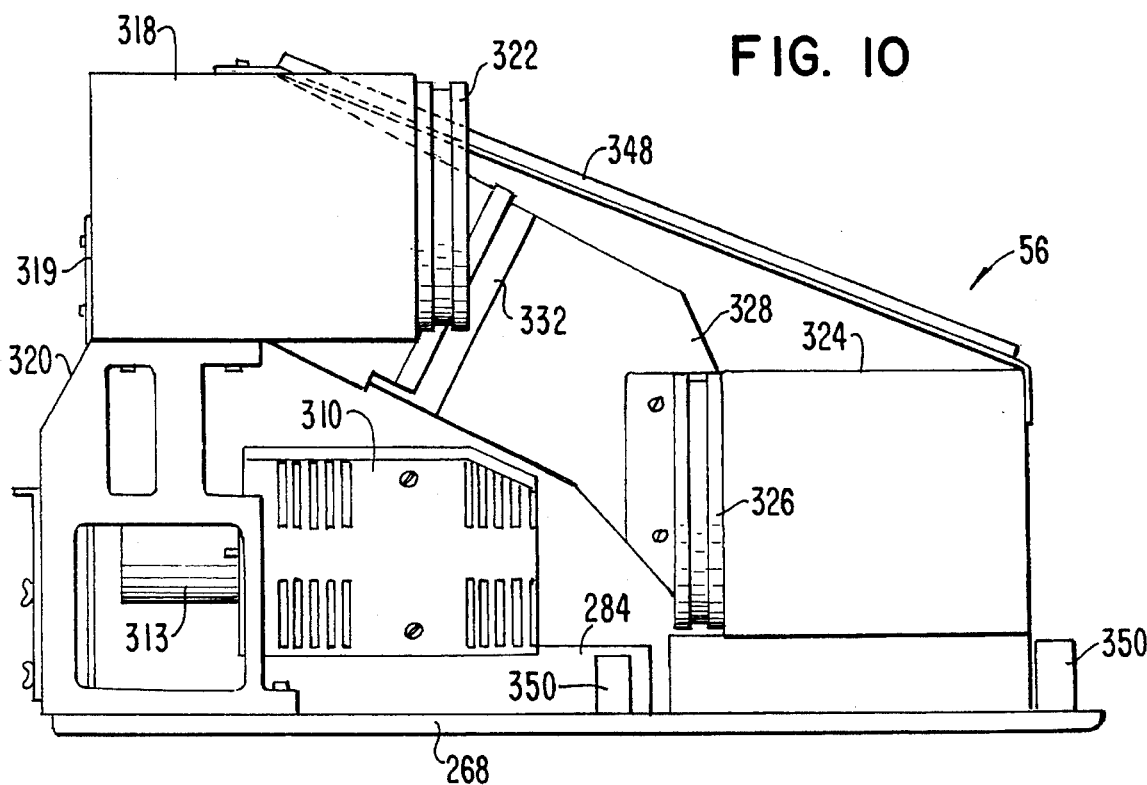

| FRACTION | % | IV |
|---|---|---|
| MM | 46.0 | 29.9 |
| MB | 34.4 | 22.4 |
| BB | 19.6 | 12.7 |
| TOTAL | | 64.9 |

| FRACTION | % | IV |
|---|---|---|
| MM | 46.0 | 29.9 |
| MB | 34.4 | 22.4 |
| BB | 19.6 | 12.7 |
| TOTAL | | 64.9 |

AUTOMATIC ELECTROPHORESIS METHOD AND APPARATUS

CROSS REFERENCE TO RELATED APPLICATION

This is a continuation-in-part of application Ser. No. 08/079,378, filed Jun. 21, 1993 now abandoned. The disclosure of this parent application is incorporated herein by reference.

BACKGROUND OF THE INVENTION

The present invention is directed in general to the field of electrophoretic analysis of liquid samples, such as biological specimens. More particularly, the invention is directed to a method and apparatus for automatically conducting electrophoresis with an electrophoresis plate.

Valuable information can be obtained by an analysis of certain biological fluids from a patient, such as blood serum, when diagnosing the patient's illness. Electrophoresis is known to be an effective technique for separating the various components of such fluid for subsequent analyses using optical densitometry techniques. The physical phenomenon underlying electrophoretic analysis is that particles which have an effective electric charge and which are deposited on a solid or semi-solid medium are caused to move with respect to the medium by an electric field applied across the medium. Particles of different types move at different rates, so a mixture of different types of particles is separated into its different components or fractions by electrophoretic analysis. These separated fractions may then be stained by exposing them to a suitable reagent so that the fractions can be optically detected using visible or ultraviolet light.

The electrophoresis process has been performed through a series of manual steps for many years. The manual process typically has started with the operator preparing an electrophoresis chamber by filling appropriate cavities of the chamber with buffer solution. Buffer solution is a liquid used in the electrophoresis process to maintain the surface of the electrophoretic medium in a moist condition and to provide an electrical interface to a power source applied to the chamber so that an electric field may be applied to the medium. The electrophoresis medium is typically a gel substance such as cellulose acetate or agarose that has been coated onto a Mylar (trademark) substrate to form an electrophoresis plate. The liquid sample to be examined is typically blood serum, but of course may be other liquids.

After the operator has prepared the electrophoresis chamber, he then applies consistent volumes of the samples to precise locations on the electrophoresis medium. The operator then places the medium into the electrophoresis chamber so that the edges of the medium are immersed in two buffer cavities at each of its longitudinal ends. Electrophoresis is then performed using a precise and consistent high voltage applied for a precise and consistent interval of time across the buffer cavities.

After electrophoresis has been completed, the operator applies a uniform coating of a staining reagent or stain to the surface of the medium, allowing a precise and consistent interval of time for the reagent and samples to chemically combine. The staining reagent is a liquid used after electrophoresis to chemically combine with the separated fractions of the fluid samples, causing the fractions to exhibit optical characteristics.

Next, the operator places the electrophoresis medium into a temperature-controlled oven and incubates it using a precise and consistent temperature and time interval. Incubation is the process of controlling the chemical reaction between the fractions of the liquid samples and the staining reagent by means of applying heat for a fixed interval of time.

Next, the operator dries the electrophoresis medium by increasing the oven temperature for a second precise and consistent temperature and time interval. The drying process stops the reaction between the separated fractions and the reagent by removing water from the medium. The medium can then be examined using optical densitometry techniques to determine which fractions were present in the original samples and to find their relative proportions.

The manual process described above requires careful attention by the operator in order to provide accurate and reproducible results. It is therefore not surprising that techniques for performing electrophoresis automatically have been developed. For example, U.S. Pat. Nos. 4,360,418 and 4,391,689 to Golias describe an automated electrophoresis and staining apparatus and method. U.S. Pat. Nos. 4,810,348, 4,890,247, 4,909,920, and 4,954,237 to Sarrine et al also describe an automated electrophoresis apparatus and method. An automated applicator assembly with pipettes for transferring samples to the electrophoresis medium during automated analysis is described in U.S. Pat. Nos. 4,827,780 and 4,938,080 to Sarrine et al. All of these patents, which are assigned to the assignee of the present invention, are incorporated herein by reference.

SUMMARY OF THE INVENTION

An object of the invention is to provide an improved method and apparatus for automatically conducting electrophoresis.

Another object of the invention is to provide an electrophoresis method and apparatus in which an electrophoresis plate is movable in a first direction and an optical means for scanning the electrophoresis plate is movable in an orthogonal second direction.

Another object is to provide an electrophoresis apparatus having an air knife which spreads a liquid reagent across the electrophoresis plate, and which can additionally be used to remove excess water from the plate before the samples are deposited on it and to blow hot air against the plate to help dry it after incubation. A related object is to provide air duct valves to isolate the electrophoresis platform from the ambient atmosphere except when air is being blown through the air knife.

Another object of the invention is to provide a method for automatically adjusting the anode voltage supplied to a photomultiplier tube in an automatic electrophoresis apparatus.

Another object is to provide a method for automatically editing data collected by an automatic electrophoresis apparatus to reduce background noise.

Another object is to provide a method for chemically avoiding background noise due to albumin when isoenzymes of creatine kinase are assayed using an automatic electrophoresis apparatus.

Another object of the invention is to provide an improved method for calibrating an applicator assembly having pipettes which transfer samples.

Another object is to provide an improved method for calibrating an electrophoresis apparatus having a platform which moves an electrophoresis plate along a first path and a gantry assembly which moves optical means for scanning the electrophoresis plate along a second path that is orthogonal to the first path.

Another object of the invention is to provide an improved method for calibrating temperature sensors and power supplies in an automatic electrophoresis machine.

In accordance with a first aspect of the invention, an electrophoresis apparatus includes: a first support for an electrophoresis plate which includes an electrophoresis medium layer; first means for moving the first support along a first linear path; an optical detector; a second support for the optical detector; and second means for moving the second support along a second linear path that passes over the first linear path and that is substantially perpendicular to the first linear path.

The first support may be an electrophoresis platform having electrodes that contact the electrophoresis medium layer.

The electrophoresis apparatus may additionally include an applicator assembly for depositing at least one liquid sample on the electrophoresis plate, the applicator assembly being disposed above the first linear path, and a reagent pouring station which is also disposed above the first linear path.

The second support may be a gantry assembly on which the optical detector is mounted, an air knife additionally being mounted on the gantry assembly. The air knife may be selectively isolated from the ambient atmosphere by one or more motor-operated air duct valves. A heater may be included in the gantry assembly to heat the air blown by the air knife to help dry the electrophoresis plate after it has been treated with reagent and incubated.

The gantry assembly may also be provided with a lamp housing for ultraviolet lamps which are part of a removable lamp assembly, and an arrangement for releasably latching the lamp assembly to the lamp housing so that the ultraviolet lamps can easily be replaced.

The optical detector may be a photomultiplier tube whose gain is automatically adjusted before data is gathered by scanning each track and reducing the anode voltage supplied to the photomultiplier tube each time the output of the photomultiplier tube, as indicated by the output of a photomultiplier tube amplifier, exceeds a predetermined value. The amplifier may have an adjustable gain and an adjustable offset. The data collected by the automatic electrophoresis apparatus may be stored in memory and automatically edited by ignoring peaks that occur outside predetermined ranges, and by establishing a base line for peaks within the predetermined ranges.

In accordance with a second aspect of the invention, a method for calibrating an electrophoresis apparatus which has a lamp for emitting ultraviolet light, a support for receiving an electrophoresis plate, and an optical detector for scanning the electrophoresis plate while it is exposed to ultraviolet light, includes the steps of: (a) placing a calibration template on the support, the calibration template having a first fluorescent line and a second fluorescent line that is perpendicular to the first line; (b) clearing a first position counter; (c) clearing a second position counter; (d) actuating a first motor to move the support and the sensor relative to one another so that the sensor passes over and detects the first line, a first position encoder being operatively connected to the first motor, the first position encoder emitting pulses as the first motor rotates; (e) using the first position counter to count the pulses emitted by the first position encoder while step (d) is conducted; (f) storing the count reached by the first position counter when the sensor detects the first line; (g) actuating a second motor to move the support and sensor relative to one another so that the sensor passes over and detects the second line, a second position encoder being operatively connected to the second motor, the second position encoder emitting pulses as the second motor rotates; (h) using the second position counter to count the pulses emitted by the second position encoder while step (g) is being conducted; and (i) storing the count reached by the second position counter when the sensor detects the second line.

In accordance with a third aspect of the invention, a method for calibrating an applicator assembly having a first member, a barrel that is vertically mounted on the first member and that has a bottom end, a second member, and a plunger that is vertically mounted on the second member and that extends into the barrel, includes the steps of: (a) clearing a first position counter; (b) clearing a second position counter; (c) actuating a first motor to move the first member to an elevated position above a support, a first position counter being operatively connected to the first motor, the first position encoder emitting pulses as the first motor rotates, the pulses emitted by the first position encoder being counted by the first position counter; (d) checking the distance between the support and the bottom end of the barrel with a go/no-go feeler gauge to determine whether the bottom end of the barrel lies within a first predetermined range of distances from the support; (e) if the bottom end of the barrel does not lie within the first predetermined range of distances from the support, actuating the first motor again to move the first member to a different position above the support; (f) repeating steps (d) and (e) until the bottom end of the barrel lies within the first predetermined range of distances from the support; (g) storing the count reached by the first position counter when the bottom end of the barrel lies within the predetermined range of distances from the support; (h) actuating a second motor to move the second member to an elevated position above the first member, the second motor being fixedly mounted with respect to the first member, a second position encoder being operatively connected to the second motor, the second position encoder emitting pulses as the second motor rotates, the pulses emitted by the second position encoder being counted by the second position counter; (i) checking the distance between the first and second members with a go/no-go feeler gauge to determine whether the distance between the members lies within a second predetermined range; (j) if the distance between the first and second members does not lie within the second predetermined range, actuating the second motor again to change the distance between the first and second members; (k) repeating steps (i) and (j) until the distance between the first and second members lies within the second predetermined range; and (1) storing the count reached by the second position counter when the distance between the first and second members lies within the second predetermined range.

In accordance with a fourth aspect of the invention, a method for analyzing a liquid sample includes the steps of: (a) depositing the sample on an electrophoresis medium layer; (b) establishing an electric field across the electrophoresis medium layer; (c) pouring a reagent on the electrophoresis medium layer; (d) spreading the reagent by blowing air against the electrophoresis medium layer through an air knife slot while moving the air knife slot and the electrophoresis medium layer with respect to one another; (e) shining ultraviolet light on the electrophoresis medium layer; and (f) scanning the electrophoresis medium layer with an optical sensor.

In accordance with a fifth aspect of the invention, a method for assaying isoenzymes of creatine kinase in a liquid sample includes the steps of: (a) placing the liquid sample in a receptacle; (b) transferring the sample to an electrophoresis medium layer; (c) establishing an electric field across the electrophoresis medium layer; (d) depositing a reagent on the electrophoresis medium layer; (e) shining ultraviolet light on the electrophoresis medium layer; (f) scanning the electrophoresis medium layer with an optical sensor; and (g) exposing the sample to a pH indicator dye before step (f) is conducted.

BRIEF DESCRIPTION OF THE DRAWINGS

FIG. 3 is a perspective view schematically illustrating air duct systems inside the housing;

FIG. 7 is a front view of an air valve in one of the air duct systems shown in FIG. 3;

FIG. 9 is a front view of the gantry assembly;

FIG. 10 is a rear view of the gantry assembly;

DESCRIPTION OF THE PREFERRED EMBODIMENT

Figure 1:
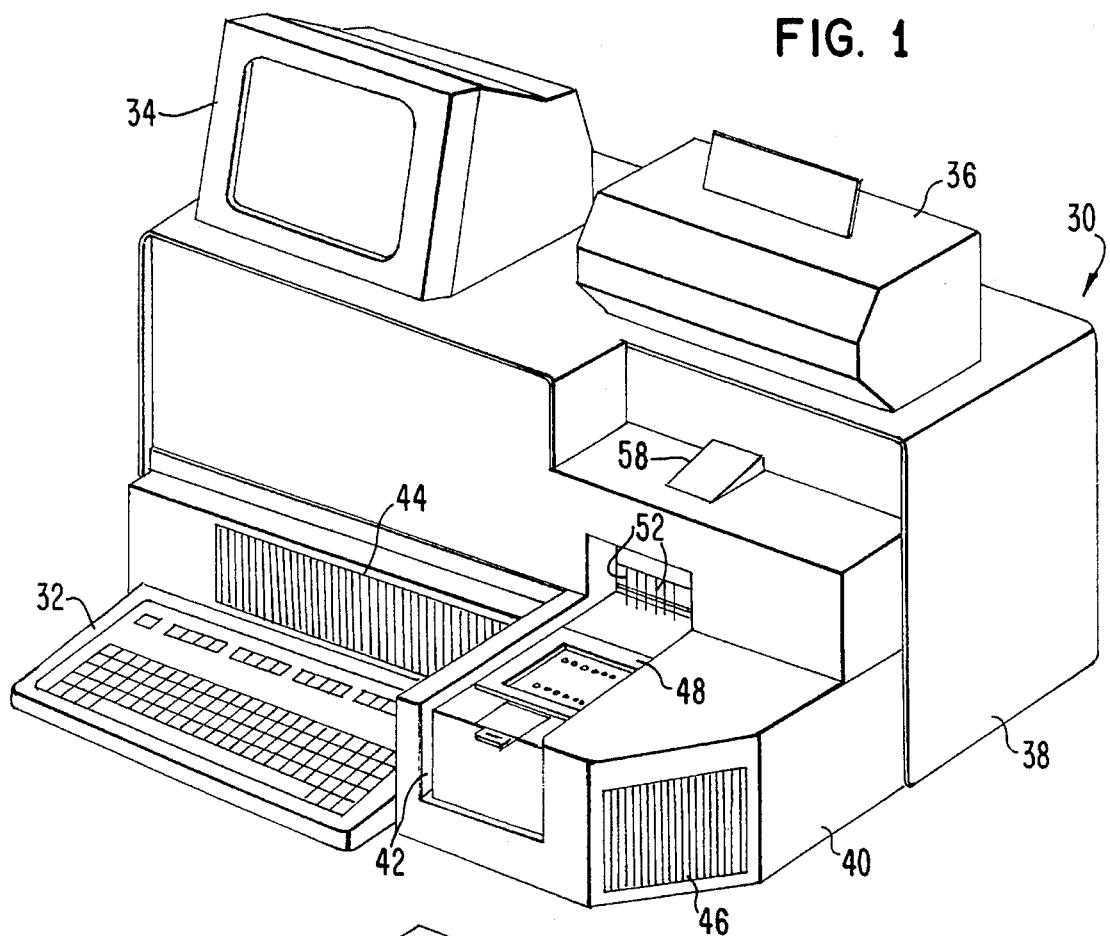
FIG. 1 is a perspective view illustrating an electrophoresis apparatus in accordance with the present invention, along with auxiliary devices used with the apparatus.

FIG. 1 illustrates an electrophoresis apparatus 30 in accordance with the present invention, along with a keyboard 32, video monitor 34, and printer 36 that are used with apparatus 30. Apparatus 30 has a housing 38 with a forward-projecting portion 40 that has a generally U-shaped channel 42, the channel 42 providing access to the interior of housing 38. Housing 38 also includes an air inlet grill 44, and an air outlet grill 46 is provided on portion 40 of housing 38.

Figure 2:
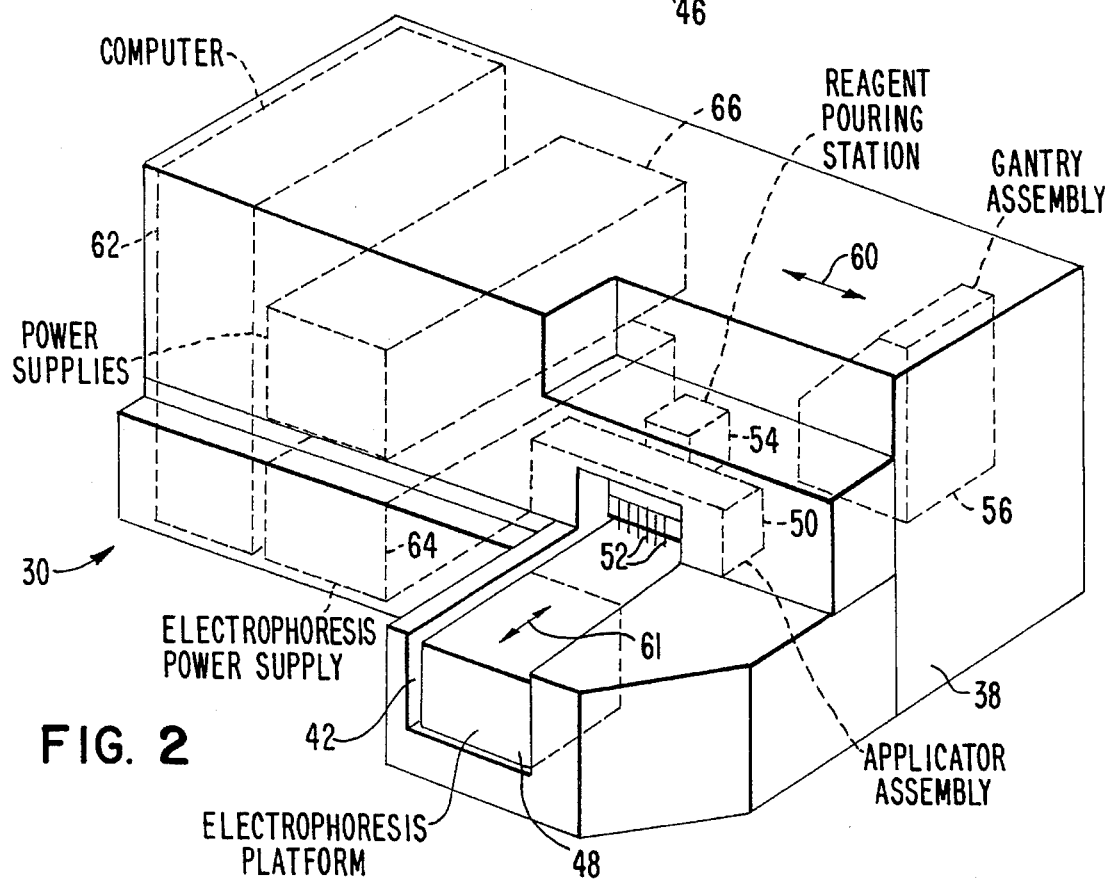
FIG. 2 is a perspective view schematically illustrating major components inside the housing of the apparatus.

FIG. 2 illustrates the major operational components within housing 38. These include an electrophoresis platform 48, an applicator assembly 50 with six pipettes 52, a reagent pouring station 54, and a gantry assembly 56. Reagent pouring station 54 is accessible via a hinged cover 58 (see FIG. 1) from outside housing 38. Gantry assembly 56 is movable within housing 38 in the direction marked by arrow 60. Electrophoresis platform 48 is movable along channel 42 from a position outside housing 38 to a position inside housing 38, as indicated by arrow 61. Platform 48 can be positioned beneath applicator assembly 50, reagent pouring station 54, and gantry assembly 56.

A computer 62, an electrophoresis power supply 64, and additional power supplies 66 are also mounted in housing 38. Computer 62 is a personal computer, such as a Dell (trademark) computer with an Intel (trademark) 386 microprocessor and a hard disk. Electrophoresis power supply 64 is a bipolar supply, meaning that it supplies potentials that are both positive and negative with respect to ground potential.

An air duct conveys air for cooling electrophoresis power supply 64. Another air duct system is provided for supplying air to electrophoresis platform 48 when it is disposed inside housing 38. A further air duct system is provided for supplying air to gantry assembly 56. These air duct systems will be further described with reference to FIG. 3.

In FIG. 3, one air duct 68 has an air entrance 70 at the front of housing 38 and extends straight back to air outlet openings (not illustrated in FIG. 3) at the rear of housing 38. Fans 72 are disposed near entrance 70 to force air through duct 68. Electrophoresis power supply 64 is disposed inside duct 68.

The air duct system for supplying air to gantry assembly 56 has an air inlet portion 74 and an air outlet portion 76. Air inlet portion 74 has an air entrance 78 disposed adjacent air entrance 70. A fan 80 is disposed in inlet portion 74, and an air duct valve 82 is provided in front of fan 80 to selectively open or close air inlet portion 74 of the duct. A collar 84 at the inner end of air inlet portion 74 is connected by a bellows 86 (see FIG. 15) to gantry assembly 56. The inner end of air outlet portion 76 has a similar collar (not illustrated) which is connected to a bellows 88 (see FIG. 15) which in turn is connected to gantry assembly 56. A fan 90 is provided in air outlet portion 76 and an air duct valve 92 is disposed just outside of fan 90 to selectively open or close portion 76. Air outlet portion 76 has an air exit 94.

The air duct system for electrophoresis platform 48 includes an air inlet portion 96 and an air outlet portion 98. Portion 96 has an air entrance 100 adjacent air entrance 78 and, at its inner end, has fans 102 to direct incoming air to electrophoresis platform 48 when the latter is in its withdrawn position. The inner end of portion 98 has an opening (not illustrated) which receives this air. Fans 104 are disposed in portion 98 of the duct, which has an air exit 106 that is positioned adjacent air exit 94. Air exit 106 and 94 are positioned behind air outlet grill 46 (see FIG. 1). Air entrances 70, 78, and 100 are positioned behind an air intake filter 108, which is housed behind air inlet grill 44.

Figure 4:
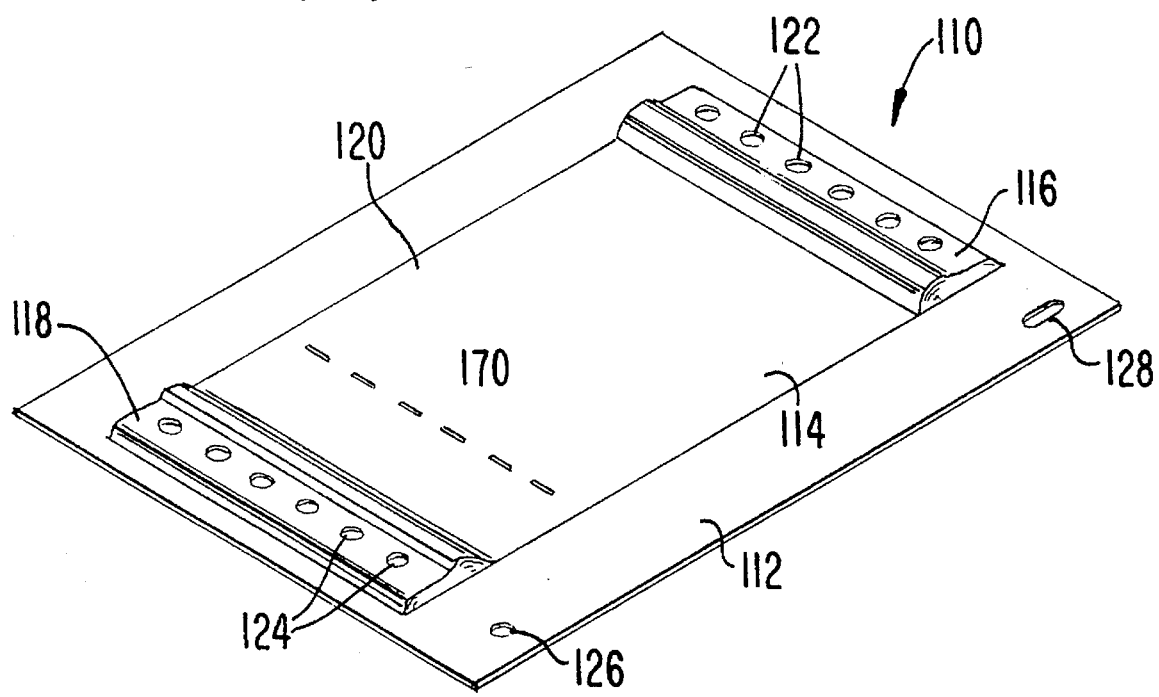
FIG. 4 is a perspective view of an electrophoresis plate that is used with the electrophoresis apparatus.

FIG. 4 illustrates an electrophoresis plate 110 which is used on electrophoresis platform 48. Plate 110 includes a substrate 112 made, for example, of a thin Mylar (trademark) plastic sheet. Substrate 112 supports an electrophoresis medium layer 114 having a first end portion 116, a second end portion 118, and a central portion 120. Electrophoresis medium layer 114 is a stiff gel which includes water and a microporous support medium such as agarose for the water. The term "microporous" means that the electrophoresis medium has tiny pores which releasably hold the water, somewhat in the manner of an extremely fine-grain sponge. A buffer is added to the water to make it electrically conductive and to adjust its Ph. A surfactant such as methyl cellulose and other components are preferably included in the water.

End portion 116 has six holes 122 and, similarly, end portion 118 has six holes 124. Substrate 112 has an alignment hole 126 and an alignment slot 128. Although not illustrated in FIG. 4, substrate 112 also has six holes aligned with the holes 122 in the end portion 116 of electrophoresis medium layer 114 and six holes aligned with the holes 124 in the end portion 118 of electrophoresis medium layer 114.

From the above description of electrophoresis plate 110 it will be apparent that the term "plate" does not imply a rigid structure; instead, electrophoresis plate 110 is rather flexible. Further details about electrophoresis plate 110 are available in application Ser. No. 08/086,918, filed 7th, 1993 by Philip A. Guadagno et al, the disclosure of which is incorporated herein by reference.

Figure 5:
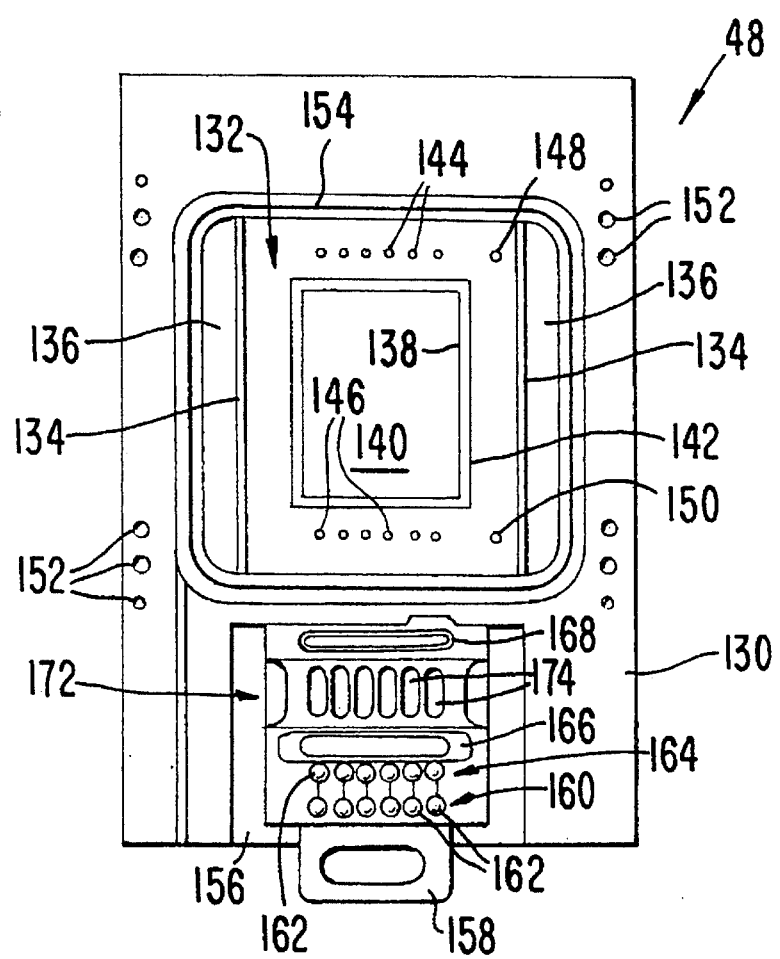
FIG. 5 is a top view of an electrophoresis platform in the apparatus, and additionally shows a sample tray resting on the platform.

FIG. 5 illustrates a top view of electrophoresis platform 48. Platform 48 includes a plastic tray 130 with a recessed region 132. A pair of ribs 134 extend upward from tray 130 in recessed region 132, and troughs 136 are provided in recessed region 132 outside of ribs 134. Tray 130 has a central opening 138 in recessed region 132. A heat-transfer member 140 is mounted beneath tray 130 and protrudes through opening 138. Member 140 has a top surface that is flush with the surface of tray 130 in recessed region 132. A plastic film 142 is adhesively attached to tray 130 at the periphery of opening 138 and covers member 140 to protect it from moisture.

Six electrodes 144 are mounted on tray 130 at one end of opening 138 and six electrodes 146 are mounted on tray 130 at the other end of opening 138. These electrodes are made of compressed graphite. Alignment pegs 148 and 150 extend upward from tray 130 in recessed region 132. Holes 152 are provided in tray 130 to accommodate screws (not illustrated) for mounting tray 130 on underlying components of electrophoresis platform 48 (which will be described later). A flexible sealing member 154 is mounted on tray 130 around recessed region 132.

When electrophoresis plate 110 of FIG. 4 is mounted in tray 130, alignment peg 150 extends through hole 126 and alignment peg 148 extends through slot 128. Furthermore, electrodes 146 extend through holes 124 and electrodes 144 extend through holes 122.

Tray 130 also has another recessed region, identified by reference number 156, for accommodating a removable sample tray 158. Tray 158 has a first row 160 of sample wells 162 and a second row 164 of sample wells 162. As shown, each row has six sample wells 162. Sample tray 158 additionally includes a trough 166 for a cleaning solution to wash the pipettes 52 (see FIG. 2, for example) of applicator assembly 50, and a trough 168 for water to wash the cleaning solution from the pipettes. The pipettes 52 transfer liquid samples from one of the row's sample wells 162 to wells 170 (see FIG. 4) molded into electrophoresis medium layer 114. A strip of paper (not illustrated) is deposited on region 172 of sample tray 158 so that the pipettes 52 can be blotted during the pipette cleaning procedure. Blotting region 172 has six depressions 174 which are positioned beneath the blotting the paper to avoid damaging pipettes 52 when they are pressed against the blotting paper.

Figure 6:
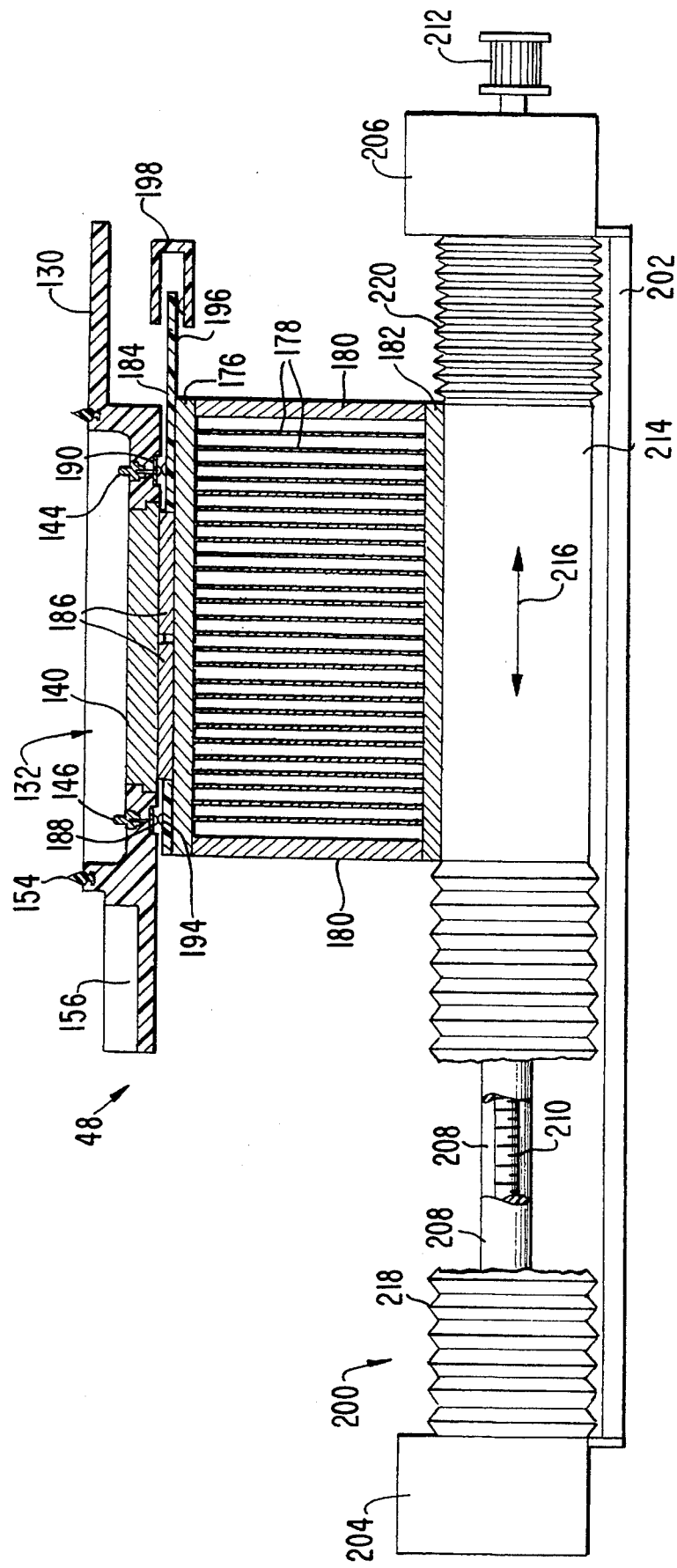
FIG. 6 is a side view, partially in section, illustrating the electrophoresis platform, a transport assembly which moves the platform, and an interlock receptacle which transfers power for electrophoresis when the platform is at a withdrawn position.

Turning next to FIG. 6, electrophoresis platform 48 also includes a heat sink 176 having fins 178. Side plates 180 connect heat sink 176 to a bottom plate 182. A printed circuit board 184 is connected to the top side of heat sink 176. PCB 184 has a central opening (not numbered) in which a pair of Peltier devices 186 are disposed. Peltier devices 186 are sandwiched between heat-transfer member 140 and heat sink 176, and can supply heat to or withdraw heat from heat-transfer member 140 in order to heat or cool electrophoresis plate 110.

As will be seen from FIG. 6, the electrodes 146 are mounted in blind bores in tray 130 and are connected by screws (not numbered) to a metal strap 188. Similarly, electrodes 144 are mounted in blind bores and are connected by screws (not numbered) to a metal scrap 190.

Although not shown in FIG. 6, PCB 184 has a conductor pattern on its top surface and a conductor pattern on its bottom surface, the conductor pattern on the bottom surface of PCB 184 being electrically insulated from heat sink 176. The conductive patterns on the top and bottom surfaces of PCB 184 are connected where appropriate by plated-through holes. Electrical power is supplied to Peltier devices 186 through the conductor patterns. Additionally, a platform temperature sensor (identified by reference number 192 in FIG. 19) is mounted on heat-transfer member 140 and is electrically connected to conductors on PCB 184. A flexible cable (not illustrated) is attached to PCB 184 to permanently connect Peltier devices 186 and temperature sensor 192 to external circuitry. However, as a safety feature the electrodes 146 and 144 are not permanently connected to electrophoresis power supply 64 (FIG. 2).

In FIG. 6, a spring contact 194 is connected to a conductor on the top surface of PCB 184. A similar spring contact, not numbered due to the small scale of the drawing, makes electrical contact with electrodes 144. These spring contacts are electrically connected to corresponding conductors at the bottom side of outer end 196 of PCB 184. An interlock receptacle 198 mounted inside housing 38 (FIG. 1) makes electrical contact with these conductors and is thus able to provide high voltage for electrodes 144 and 146 only when platform 48 is in its withdrawn position.

Further details about electrophoresis platform 48 are explained in application Ser. No. 08/079,229, filed Jun. 21, 1993 by Robert J. Sarrine, the disclosure of which is incorporated herein by reference.

Electrophoresis platform 48 is mounted on a transport assembly 200 which includes a base 202 and end members 204 and 206 mounted on base 202. Two guide bars 208 are fixed to end members 204 and 206, and a shaft 210 is journalled for rotation on members 204 and 206 and disposed midway between the guide bars 208. Shaft 210 is finely threaded along most of its length. A toothed pulley 212 is connected to the outer end of shaft 210. Bottom plate 182 of electrophoresis platform 48 is mounted on a chassis 214 which rides on guide bars 208 and which encloses a nut (not illustrated) that meshes with the threaded portion of shaft 210, so that rotation of pulley 212 and thus shaft 210 causes chassis 214 to move along guide bars 208 as indicated by arrow 216. A bellows 218 is connected between end member 204 and chassis 214 and another bellows, numbered 220, is connected between chassis 214 and end member 206. The purpose of bellows 218 and 220 is not to convey air as part of the previously-described duct systems, but instead to protect guide bars 208 and shaft 210 from dust and debris. Transport assembly 200 is commercially available from Thompson Industries, Inc. of Fort Washington, N.Y., under the trademark "Superslide."

FIG. 7 illustrates air duct valve 82. It includes a back plate 222 and a front plate 224 that is connected to back plate 222 with screws. Front plate 224 has a rectangular opening 226 which is aligned with a corresponding opening in back plate 222. A duct valve motor 230 has a flange 228 that is connected to back plate 222 by screws 232. Motor 230 has an internal nut (not illustrated) which engages a threaded shaft 234, which is moved linearly when the nut is rotated by motor 230. The bottom end of shaft 234 is connected to an intermediate plate 235 which is slidably mounted between plates 222 and 224. It will be apparent that motor 230 can move plate 235 into a position where it blocks opening 226, or withdraw it from the opening to permit passage of air through the duct portion in which valve 82 is mounted. Air duct valve 92 has the same construction as valve 82.

Figure 8:
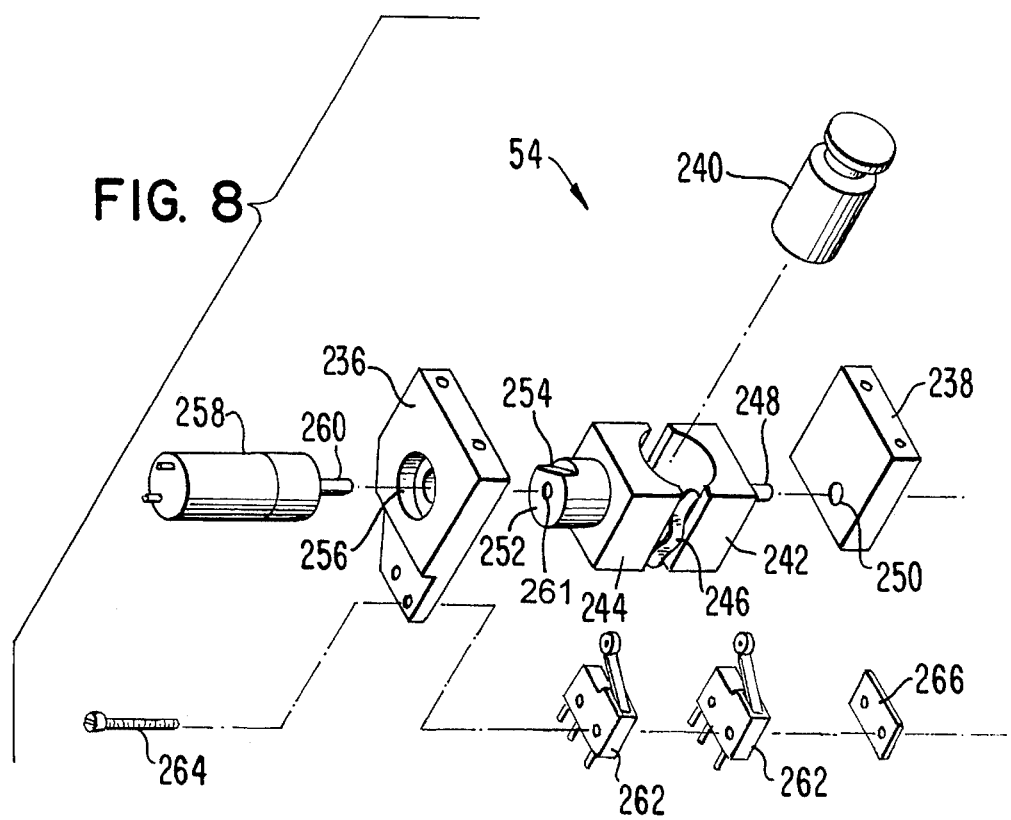
FIG. 8 is an exploded perspective view of a reagent applicator assembly.
Figure 14:
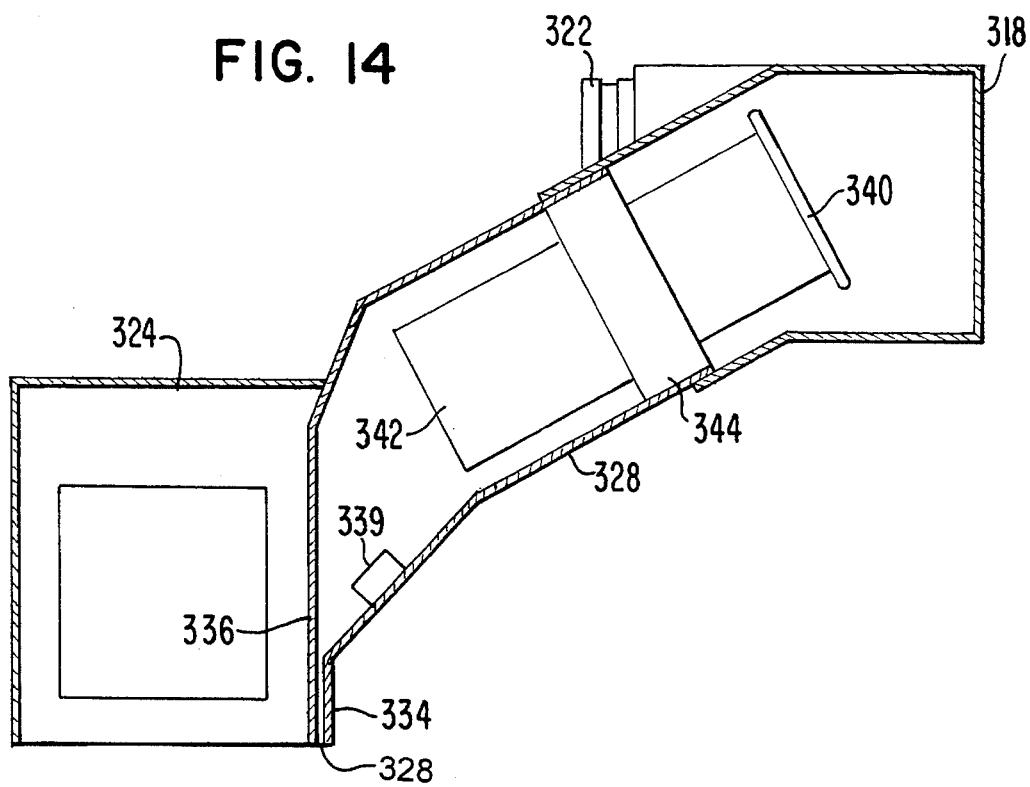
FIG. 14 is a sectional view illustrating air guides provided by the gantry assembly.
Figure 11:
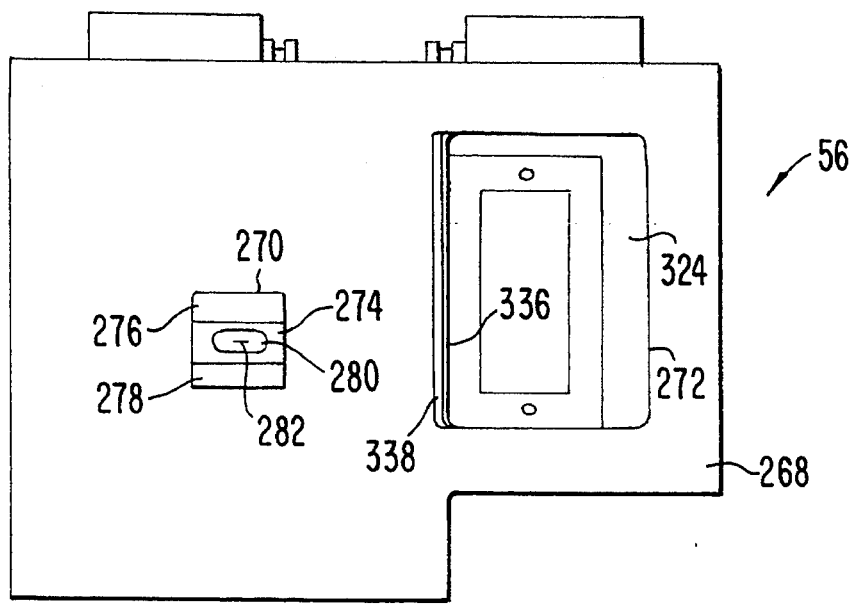
FIG. 11 is a bottom view of the gantry assembly.
Figure 12:
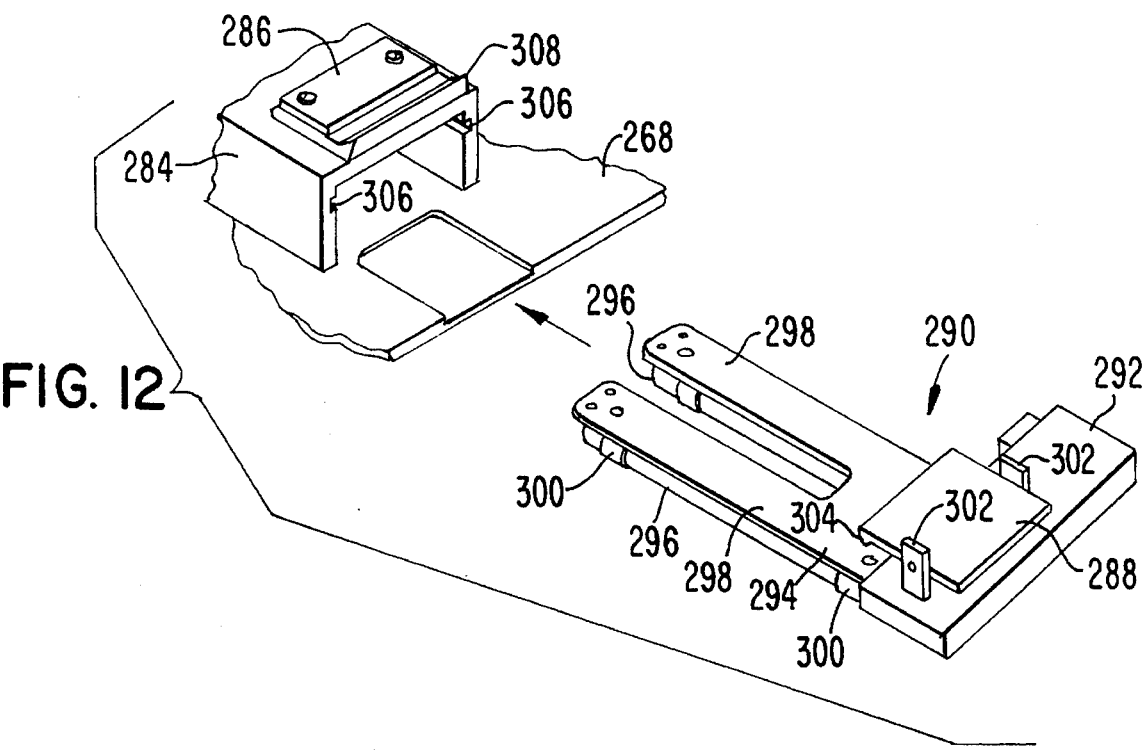
FIG. 12 is an exploded perspective view, partially broken away, illustrating a lamp assembly which is releasably received in a lamp housing of the gantry assembly.
Figure 13:
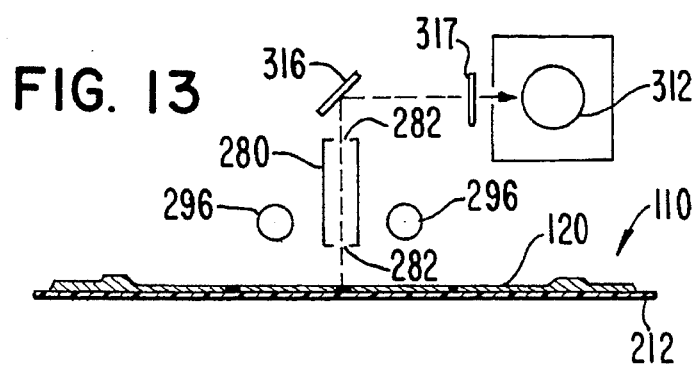
FIG. 13 schematically illustrates exposure of the electrophoresis plate by ultraviolet lamps in the gantry assembly and measurement of the resulting florescence by a photomultiplier tube in the gantry assembly.

FIG. 8 illustrates reagent pouring station 54, which includes mounting members 236 and 238. A receptacle for a reagent vial 240 includes a first receptacle portion 242 and a second receptacle portion 244. A spring finger 246 is mounted on receptacle portions 242 and 244 to retain vial 240 in the receptacle. Receptacle portion 242 has a peg 248 which extends into a bore 250 to journal portion 242 for rotation with respect to mounting member 238. Receptacle portion 244 has a stem 252 with a pair of flat cam surfaces 254 (only one of which is shown) on it. One side of mounting member 236 has a recess 256 which receives the front end of a reagent drive motor 258. Motor 258 is a gear motor (that is, it includes reduction gearing built into the motor housing). The shaft 260 of motor 258 is connected to stem 252, extending into an opening 261 in the stem.

Limit switches 262 are attached to mounting member 236 by screws 264 (only one of which is shown) and a backing plate 266. Switches 262 are positioned to engage the cam surfaces 254 to detect whether vial 240 is upside down or right side up. As was indicated previously, an empty vial 240 can be withdrawn from reagent pouring station 54 via hinged cover 58 (see FIG. 1) and replaced by a full vial of reagent.

Gantry assembly 56 will now be described with reference to FIGS. 9–14. Gantry assembly 56 has a base 268 with an optical window 270 and a pneumatic window 272 in it. A brace 274 is mounted on base 268 and extends across window 270, leaving two equal portions 276 and 278 of window 270 unobstructed. A collimator 280 is mounted on brace 274. Collimator 280 is a short, hollow tube which is closed at its upper and lower ends, except for slits 282 in the ends. Slits 282 are aligned, so that light passing through the lower slit 282 also passes through the upper slit 282 only if the rays are parallel to the longitudinal axis of collimator 280.

A lamp housing 284 is mounted on base 268 above optical window 270. Housing 284 has a latch plate 286 (see FIG. 12; latch plate 286 is not shown in FIGS. 9 and 10) to cooperate with a latch 288 (see FIG. 12) on a lamp assembly 290. Lamp assembly 290 includes a support 292, a generally U-shaped printed circuit board 294 connected to support 292, and a pair of ultraviolet lamps 296 which are connected to the arms 298 of PCB 294 by straps 300. Latch 288 is pivotally mounted on protrusions 302 extending from support 292 and is biased by a spring (not illustrated) so as to urge the tooth 304 of latch 288 downward.

The walls of lamp housing 284 have grooves 306 which slidably receive the edges of arms 298 of PCB 294. When lamp assembly 290 is fully inserted, the tooth 304 of latch 288 slips over the tooth 308 of latch plate 286 to releasably lock lamp assembly 290 inside housing 284. In this inserted position, part of one of the lamps 296 is exposed through unobstructed portion 276 of optical window 270 and part of the other lamp 296 is exposed through unobstructed portion 278 of window 270; collimator 280 extends upward between the arms 298 of PCB 294.

A housing 310 for a photomultiplier tube or PMT 312 is mounted on lamp housing 284. A socket 313 for PMT 312 is mounted on housing 310. Reference number 316 identifies a mirror which is mounted on a plate 314 which in turn is mounted on an extending portion 315 of housing 284. Mirror 316 is positioned at an opening (not illustrated) in the side of PMT housing 310. Collimator 280 extends through lamp housing 284 and into PMT housing 310, and mirror 316 reflects light that has passed through collimator 280 to PMT 312. Reference number 317 identifies an ultraviolet filter.

A first air guide 318 is supported over base 268 by braces 319 and 320. First air guide 318 has a collar 322 for connection to bellows 86 (see FIG. 15). A second air guide 324 is mounted on base 268 over pneumatic window 272. Second air guide 324 is open at the bottom, so that pneumatic opening 272 in base 268 provides an entrance into guide 324. Guide 324 has a collar 326 for connection to bellows 88 (see FIG. 15).

An air knife guide 328 is mounted on guide 324 by screws 330 and is sealingly connected to guide 318 by duct tape 332. Air knife guide 328 includes a wall 334 which is spaced slightly apart from a wall 336 to provide an air knife slot 338. An air knife or gantry blower 340 and a heater 342 are connected to a mounting member 344 that is attached to guide 328. Reference number 339 designates a temperature sensor. As will be seen from FIG. 14, blower 340 extends into the space inside first air guide 318. When blower 340 is turned on, it forces air toward air knife slot 338, which is positioned at one edge of pneumatic opening 272. This air can then be collected via pneumatic opening 272 and air guide 324.

A brace 348 is screwed to first and second air guides 318 and 324 to increase the structural rigidity of gantry assembly 56 and to provide a support for mounting a printed circuit board (not illustrated) with some of the electrical circuitry of electrophoresis apparatus 30. Slide bearings 350 are mounted on base 268 along the opposite sides thereof.

Figure 15:
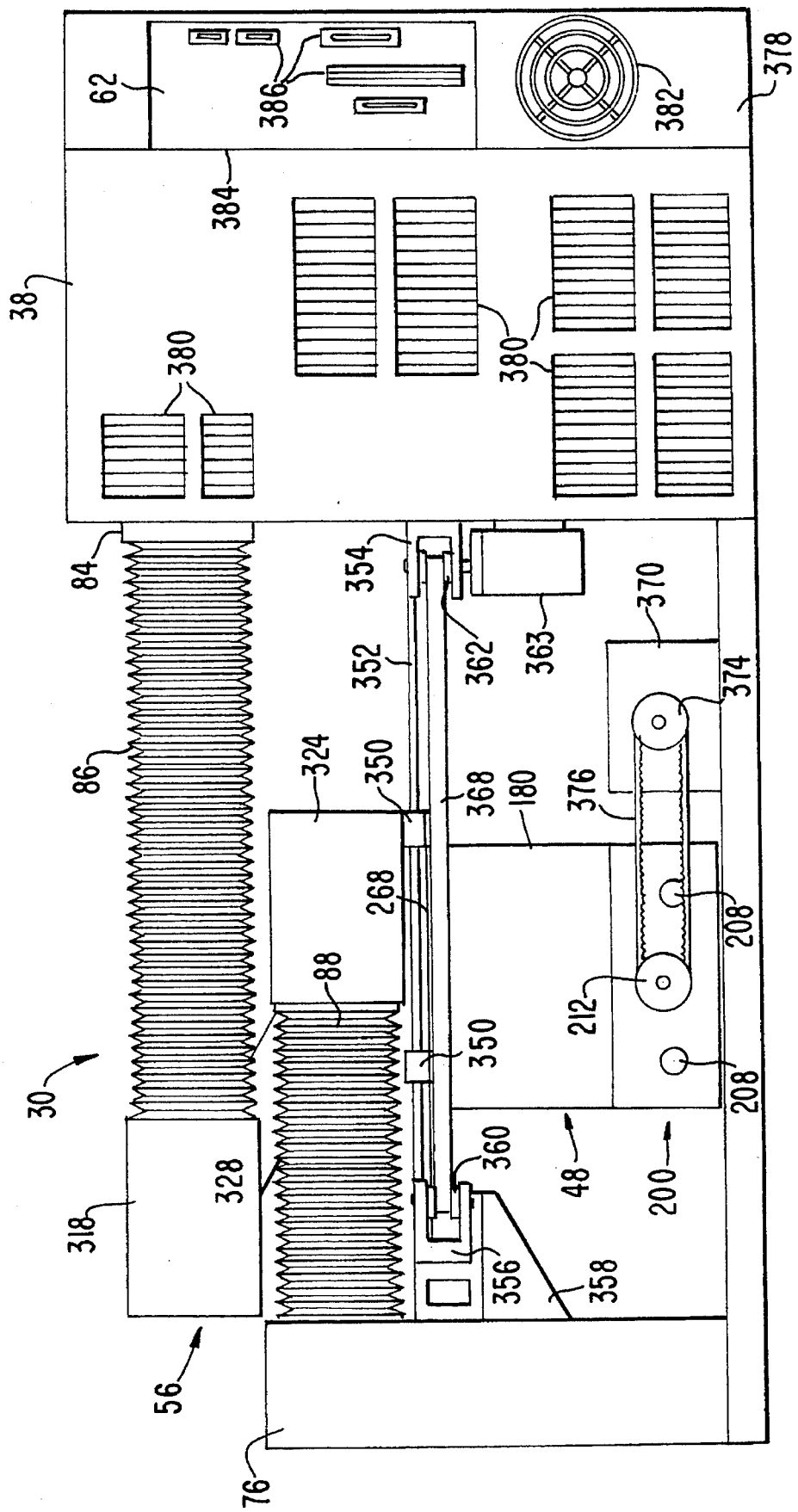
FIG. 15 is a rear view of the electrophoresis apparatus with some of the panels of the housing removed.

Turning next to FIG. 15, which shows the back side of electrophoresis apparatus 30 with some of the outer panels of housing 38 removed, a pair of guide bars 352 (only one of which is shown) are mounted on housing 38. These guide bars extend through bores (not illustrated) in slide bearings 350 to mount gantry assembly 56 for lateral movement. A bracket 354 is connected to housing 38 and another bracket 356 is connected to a support 358 attached to air duct outlet portion 76. A toothed pulley 360 is rotatably mounted on bracket 356. A toothed pulley 362 is rotatably mounted on bracket 354. Pulley 362 is driven by a gantry drive motor 363 which is connected to housing 38. Motor 362 is a stepper motor, with reduction gearing, and furthermore has a rotary position encoder 366 (see FIG. 20) attached to the motor housing. A toothed belt 368 is stretched between pulleys 360 and 362 and is connected to gantry assembly 56, so that motor 363 can slide gantry assembly 56 back and forth along guide rods 352 via belt 368.

A platform drive motor 370 is mounted on housing 38. It, too, is a stepper motor, and has a rotary position encoder 372 (see FIG. 20) attached to its housing. A toothed pulley 374 is connected to the shaft of motor 370. A toothed belt 376 extends between pulleys 374 and 212. It will be apparent that motor 370 moves electrophoresis platform 48 forward and backward via belt 376 and transport assembly 200.

FIG. 15 also illustrates a rear panel 378 of housing 38. It includes various grills 380 for passage of air and a further air vent 382 that is aligned with a cooling fan (not illustrated) that is part of computer 62. Panel 378 also includes a window 384 which exposes various connectors 386 at the rear of computer 62.

Figure 16:
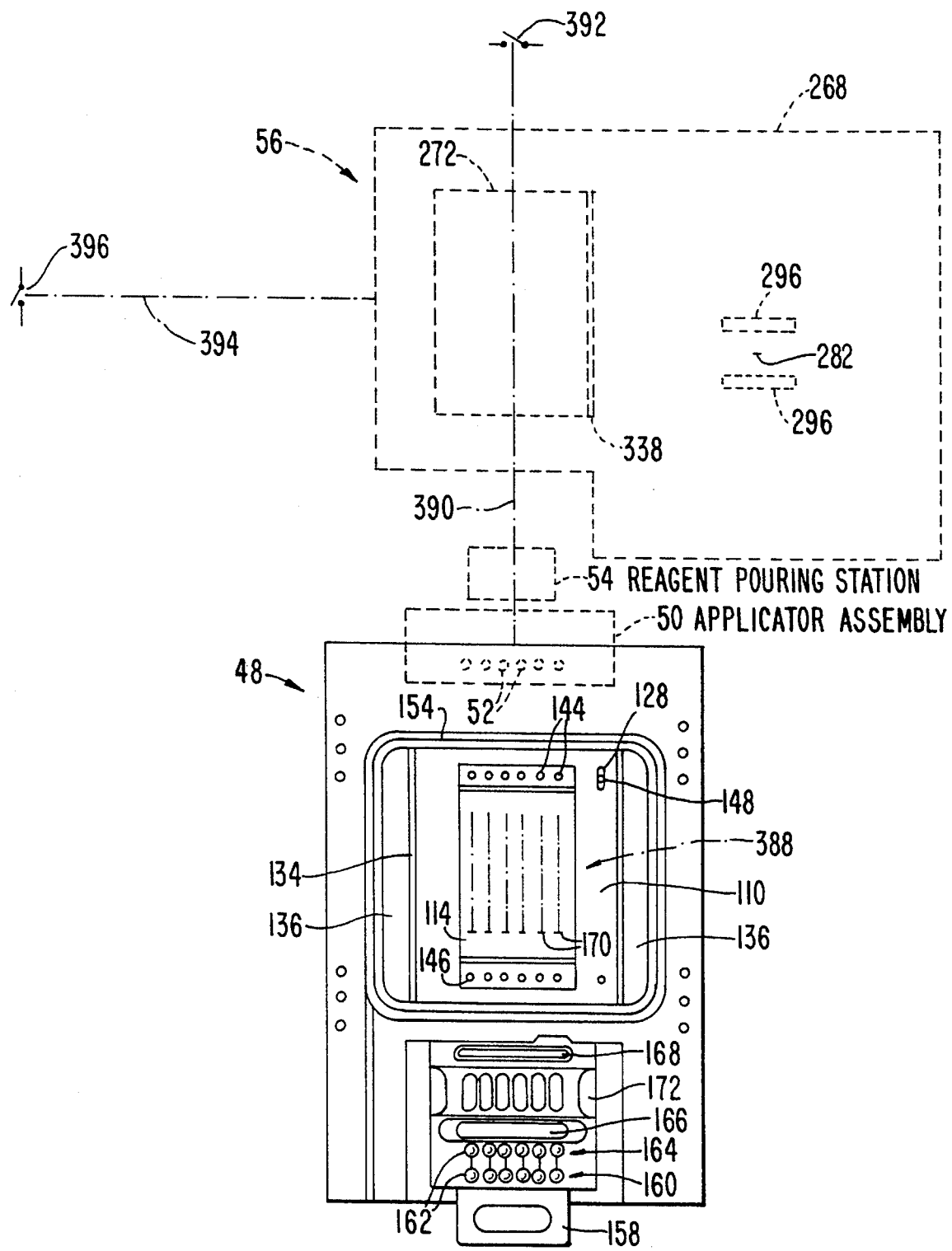
FIG. 16 is a top view schematically illustrating how the platform assembly cooperates with the applicator assembly, the reagent pouring station, and the gantry assembly.

How electrophoresis platform 48 cooperates with gantry assembly 56 will now be further explained with reference to FIG. 16. FIG. 16 illustrates a top view of these components, with platform 48 positioned at the front and gantry assembly 56 positioned at the right as in FIG. 2. Gantry assembly 56 is shown with dotted lines since it is the base 268 thereof that is depicted. During electrophoresis different fractions of samples that have been deposited in wells 170 of electrophoresis plate 110 move physically at different rates along six tracks that are schematically illustrated by dot-dash chain lines 388.

From the foregoing discussion it will be apparent that platform 48 is movable along a platform path 390. By moving it along this path, platform 48 can be positioned beneath applicator assembly 50, reagent pouring station 54, or gantry assembly 56. Reference number 392 schematically illustrates a home switch at the inner end of platform path 390. Gantry assembly 56 is movable along a gantry path 394 that is perpendicular to platform path 390. Reference number 396 schematically illustrates a home switch at the left end of gantry path 394.

During electrophoresis itself, gantry assembly 56 is positioned as shown in FIG. 16 and electrophoresis platform 48 is moved along platform path 390 to an electrophoresis position. In this position, electrophoresis plate 110 is disposed directly under pneumatic window 272, and sealing member 154 engages the underside of base 268 around the periphery of window 272, so that platform 48 and gantry assembly 56 together constitute an electrophoresis chamber. After electrophoresis has been conducted, platform 48 is moved forward along platform path 390 to a position beneath reagent pouring station 54, where a vial of reagent is poured onto plate 110. Platform 48 is then moved back along platform path 390 to a reagent spread position, which is the same as the electrophoresis position. Gantry assembly 56 is moved back and forth along gantry path 394 while air is blown downward gently through air knife slot 338. This spreads the reagent uniformly across electrophoresis medium layer 114. The air received through air knife slot 338 is exhausted via pneumatic window 272. The reagent can later be removed by blowing air rapidly through air knife slot 338 while moving gantry assembly 56 across electrophoresis plate 110. This sweeps the reagent into troughs 136.

After incubation and drying of the reagent, which will be described in more detail subsequently, gantry assembly 56 again cooperates with platform 48 to obtain optical data for analysis using densitometry techniques. With platform 48 at the inner position, gantry assembly 56 is moved along gantry path 394 until slit 282 is aligned with a first one of the tracks 388. Ultraviolet light from lamps 296 causes the reagent-treated sample along this track to fluoresce, and fluorescent light that is emitted directly upward passes through collimator 280 and is reflected by mirror 316 to PMT 312. This is shown schematically in FIG. 13, where ultraviolet filter 317 absorbs any ultraviolet light that may be reflected from plate 110. Platform 48 is moved along platform path 390 to move the first track 388 with respect to slit 282, after which the position of gantry assembly along gantry path 394 is shifted slightly to bring slit 282 over the second path 388. In this way the electrophoresis platform 48 and gantry assembly 56 cooperate to scan the six tracks 388 one by one.

Figure 17:
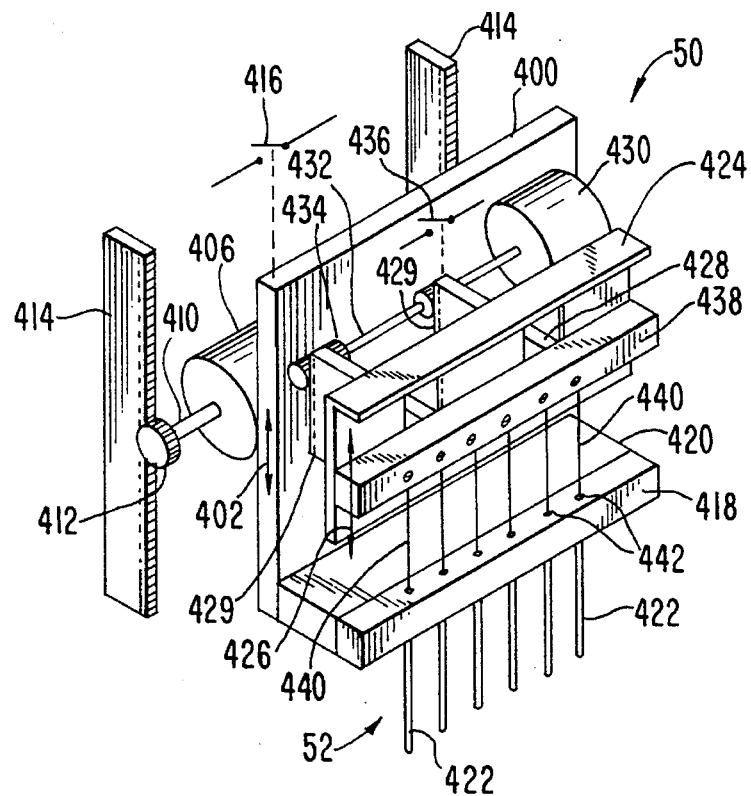
FIG. 17 is a perspective view schematically illustrating the applicator assembly.

FIG. 17 depicts a schematic illustration of applicator assembly 50 to demonstrate its operational features. Applicator assembly 50 includes a back plate 400 that is mounted (by means not shown) for up and down movement, as indicated by arrow 402. A pipette barrels motor 406 is connected to the rear side of plate 400. Motor 406 is a gear motor having a positioning encoder 408 (see FIG. 20) built into its housing. Motor 406 has a shaft 410 which protrudes from both ends of the motor. A pinion 412 is connected to each end of shaft 410 and meshes with a respective rack of teeth 414 that is connected to housing 38 of the electrophoresis apparatus. It will be apparent that motor 406 can be actuated to move plate 400 in the direction of arrow 402. Reference number 416 schematically designates a home switch which is closed when motor 406 raises plate 400 to a predetermined elevated position.

A pipette bar 418 is connected to a spacer 420 which in turn is connected to back plate 400. Six pipette barrels 422 are attached to pipette bar 418 at the bottom side thereof.

An actuator yoke 424 is mounted (by means not shown) on back plate 400 for movement up and down, as indicated by arrow 426. A pair of legs 428 extend backward from yoke 424 and terminate in racks of teeth 429. A pipette plungers motor 430 is attached to plate 400 and has a shaft 432 to which a pair of pinions 434 are connected. Motor 430 is a gear motor with an encoder 431 (see FIG. 20) built into its housing. Pinions 434 mesh with racks of teeth 429, so that yoke 424 can be moved with respect to back plate 400 in the direction of arrow 426 by actuation of motor 430 in the appropriate direction. A home switch that is connected to back plate 400 is schematically illustrated at 436. Switch 436 is closed when motor 430 has raised yoke 424 to a predetermined position above spacer 420.

A plunger bar 438 is connected to the front side of actuator yoke 424. Six pipette plungers 440 are connected to the bottom side of bar 438 and extend through openings 442 in pipette bar 418 and into pipette barrels 422. Each barrel 422 and its associated plunger 440 cooperate to form a pipette 52. The vertical position of the pipettes 52 is controlled by motor 406, and motor 430 controls the drawing of fluid into the pipettes 52 or the expelling of fluid from the pipettes.

Figure 18:
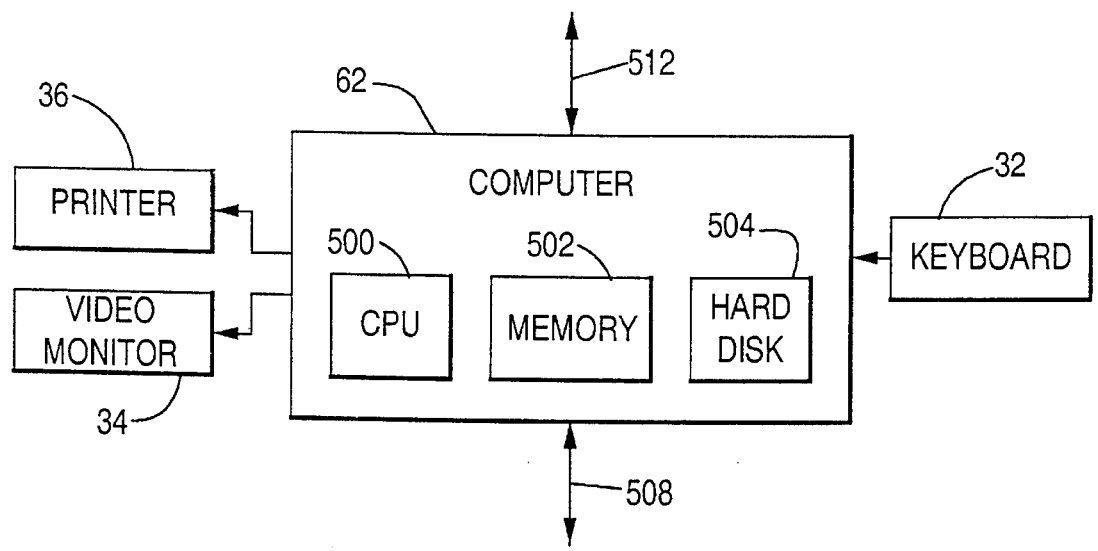
FIGS. 18, 19, and 20 illustrate a block diagram of the electrical circuitry of the electrophoresis apparatus.

The electrical circuitry of electrophoresis apparatus 30 will now be described with reference to FIGS. 18–20.

Computer 62 includes, inter alia, a CPU 500, a read/write memory 502, and non-volatile memory in the form of hard disk 504. Disk 504 stores programs for operating the electrophoresis apparatus 30 and also stores values needed during such operation, such as calibration values. Computer 62 is connected to a digital I/O circuit 506 by a bus 508. Computer 62 is also connected to an analog I/O circuit 510 by a bus 512. Analog I/O circuit 510 includes D/A and A/D converters (not illustrated) so that circuit 510 can receive digital values from computer 62 and supply corresponding analog voltages to the analog circuitry connected to circuit 510, and so that it can receive analog voltages from this circuitry and convey the digital equivalents to computer 62.

Power supplies 66 (see FIG. 2) include a lamp power supply 513, a Peltier power supply 514, and a power supply 516 for photomultiplier tube 312. The PMT power supply 516 receives a voltage control signal from analog I/O circuit 510 and supplies a PMT voltage designated by this control signal to the anode (not shown) of PMT 312. A PMT voltage monitor 518 is connected to power supply 516 in order to supply a monitor signal to circuit 510. This monitor signal is proportional to the actual output voltage of power supply 516. The output of PMT 312 is amplified by an amplifier 520 and supplied to circuit 510, which transfers the amplified PMT output to computer 62 in digital form. Amplifier 520 has a gain input port and an offset input port which respectively receive signals from I/O circuit 510 to set the gain or signal multiplication factor of amplifier 520 and to set the offset or DC level of amplifier 520.

Peltier power supply 514 supplies current, in either a heating direction or cooling direction, to Peltier devices 186. A current monitor 522 is connected to power supply 514 to provide circuit 510 with a monitor signal proportional to the actual current output and polarity. As was previously mentioned, platform temperature sensor 192 is mounted on heat-transfer member 140 (see FIG. 6) and thus effectively senses the temperature of Peltier devices 186. Sensor 192 supplies a sensor signal to circuit 510.

Electrophoresis power supply 64 is a bipolar power supply. It has two output ports 524 and 526, one of which is positive with respect to ground and the other of which is negative with respect to ground. Circuit 510 supplies power supply 64 with a control signal which serves to set the potential at the positive port to a designated value between 0 and 750 volts and to set the potential at the negative port to minus the designated value. Ports 524 and 526 are connected to electrodes 144 and 146 by interlock receptacle 198 (see FIG. 6) when electrophoresis platform 48 is at the electrophoresis position. An electrode current and voltage monitor 528 is connected to power supply 64 to supply monitor signals to circuit 510.

A gantry heater control circuit 530 receives a control signal from circuit 510 and drives gantry heater 342 at a power level determined by the control signal. Gantry temperature sensor 443 supplies circuit 510 with a sensor signal.

Air knife or gantry blower 340 (see FIG. 14) includes a gantry blower motor 532 that is driven by a motor control circuit 534 which receives a control signal from circuit 510.

Fans 102 and 104 (see FIG. 3) include duct fan motors 536 and fans 80 and 90 (FIG. 3) include duct fan motors 538. Motor control circuits 540 and 542 receive signals from circuit 506 to turn these fans on or off. A motor control circuit 544 connected to I/O circuit 506 controls duct valve motors 230 to open or close air duct valves 82 and 92 (see FIG. 3). Similarly, a motor control circuit 546 receives a control signal from circuit 506 and drives gantry drive motor 364 accordingly; a motor control circuit 548 receives a control signal from circuit 506 and drives pipette plungers motor 430 accordingly; a motor control circuit 550 receives a control signal from circuit 506 and drives pipette barrels motor 406 accordingly; a motor control circuit 552 receives a control signal from circuit 506 and drives reagent drive motor accordingly; and a motor control circuit 554 receives a control signal from circuit 506 and drives platform drive motor 370 accordingly. Position encoders 366, 372, 408, and 431 emit pulses to circuit 506 as the respective motors rotate, each pulse indicating that the respective motor has rotated through a small predetermined angle.

Home switch 392 emits a signal to circuit 506 when electrophoresis platform 48 is located at its home position (see FIG. 16, for example). Home switch 396 emits a signal to circuit 506 when gantry assembly 56 is at its home position. Similarly, home switches 416 and 436 emit signals to circuit 506 when the pipette barrels motor 406 and pipette plungers motor 430 are at their home positions.

Hard disk 504 stores a program for operating electrophoresis apparatus 30 during normal operation to perform an assay. It also stores various user-programmable values, such as temperatures and times to be used during assays, along with user-programmable options such as how the results of assays are to be presented. Hard disk 504 additionally stores values which characterize various components of apparatus 30 and which are used by the program when apparatus 30 is employed to conduct an assay. For example, the characteristics of the temperature sensors and the summed values of encoder pulses which represent particular positions of mechanical components are stored beforehand for use by the program. Approximately-correct default values are stored when apparatus 30 is manufactured but it is preferable to calibrate apparatus 30 before use to replace these default values with improved values that are characteristic of the individual apparatus 30. However, a discussion of the calibration procedures will be delayed until normal operation of apparatus 30 to conduct an assay is described with reference to the program illustrated in FIGS. 21A–21M.

This program will be described in the context of a typical use for electrophoresis apparatus 30, which is to assay the isoforms of creatine kinase of a patient to confirm a diagnoses of myocardial infarction. These isoforms include the MM isoenzyme or fraction (which is associated with muscular exercise or injury or a muscle-wasting disease), the MB isoenzyme or fraction (which is associated with heart tissue), and the BB isoenzyme or fraction (which is associated with the nervous and digestive systems). Measurements of the actual and relative quantities of these isoenzymes, particularly at different times to indicate trends, provide physicians with valuable diagnostic information.

In a typical situation blood would be drawn from a patient three times at hourly intervals and centrifuged to provide three plasma samples. The operator conducting the assay would place these three samples in three of the wells 162 (see FIG. 5) in one of the rows 160 or 164 of sample tray 158. The operator would place a normal control fluid, an abnormal control fluid, and a reference/calibrator fluid in the remaining three wells 162 of the row. The operator would then place the sample tray 158 and an electrophoresis plate 110 on electrophoresis platform 48 before turning electrophoresis apparatus 30 on.

Figure 20:
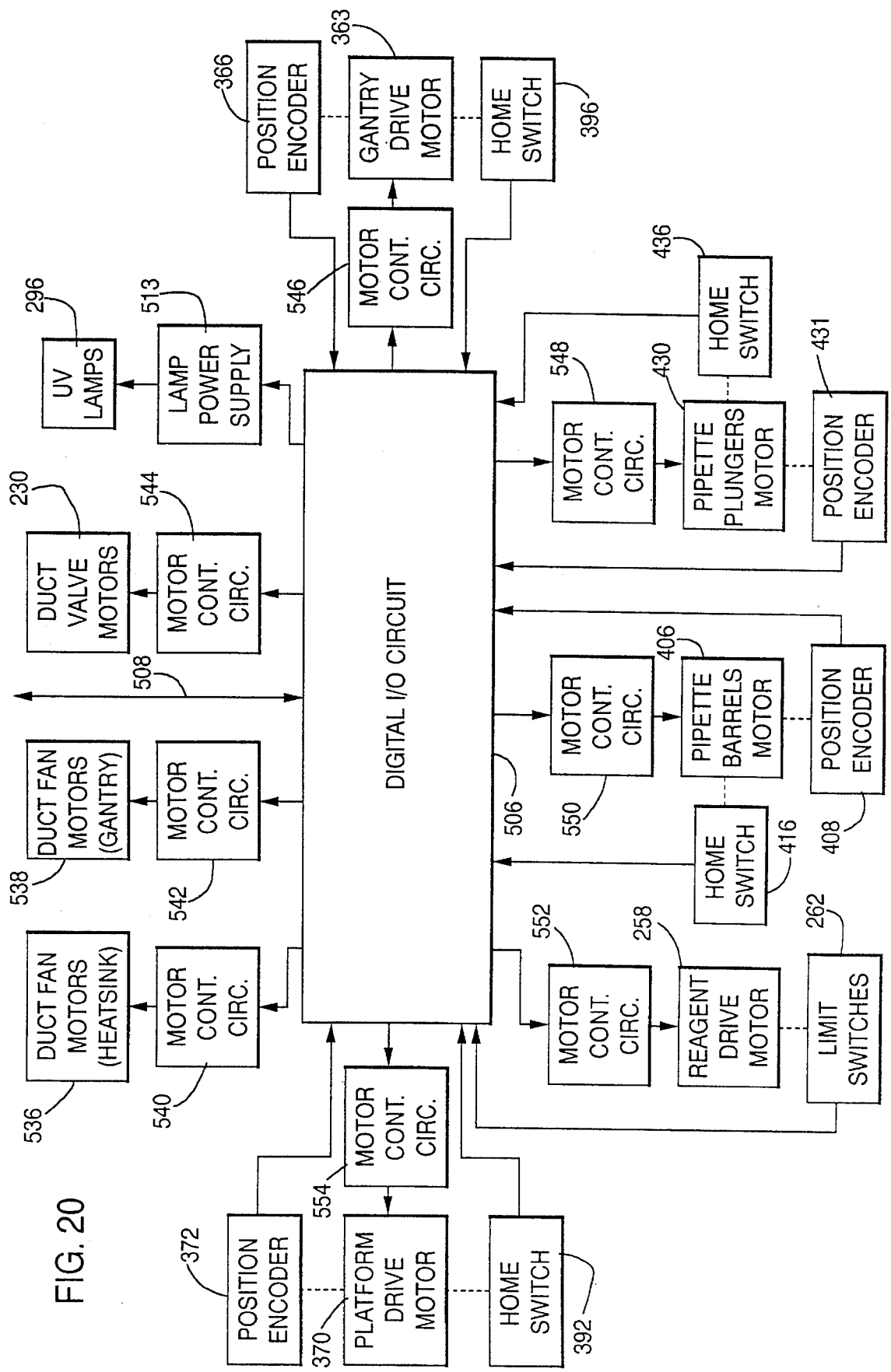
Figure 21A:
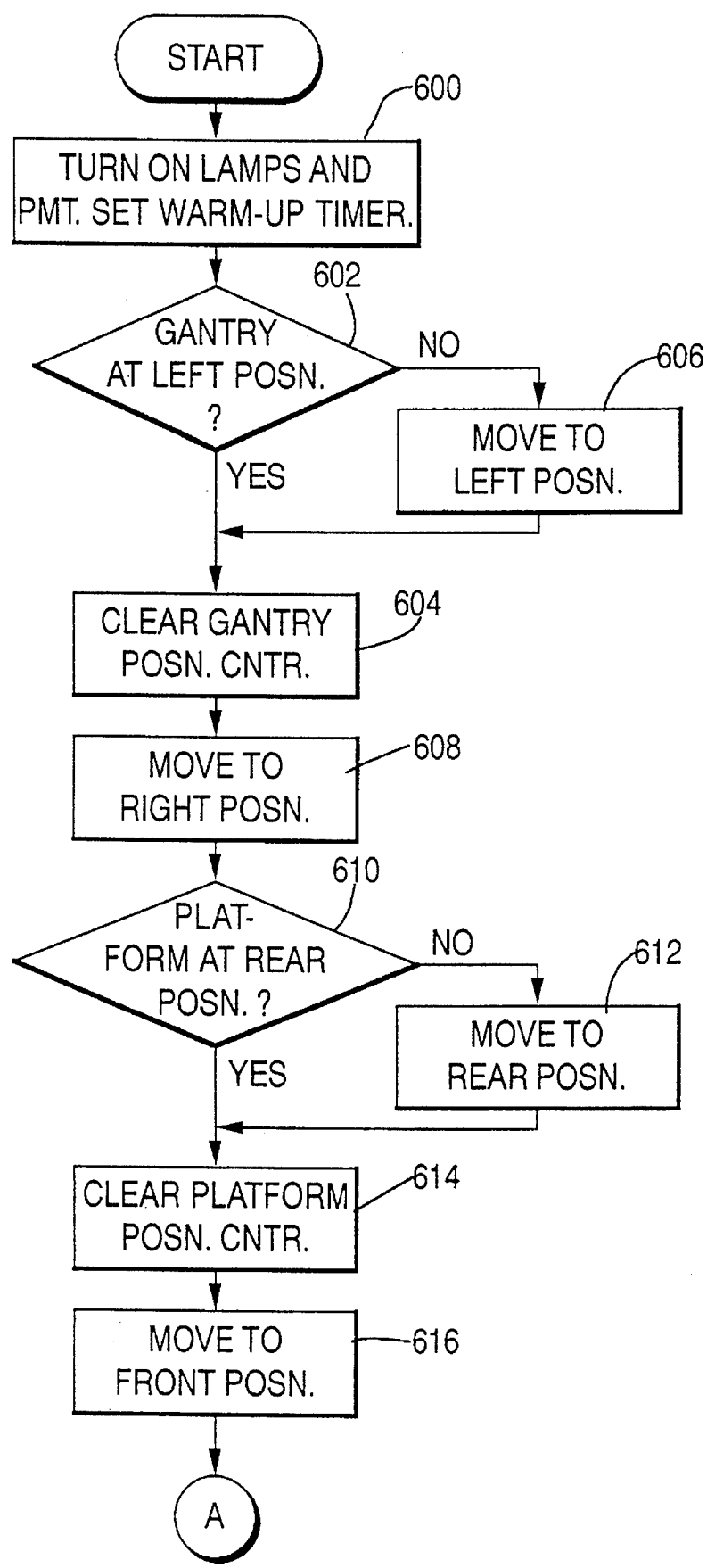
FIGS. 21A–21M illustrate a flow chart for normal operation of the electrophoresis apparatus.
Figure 21B:
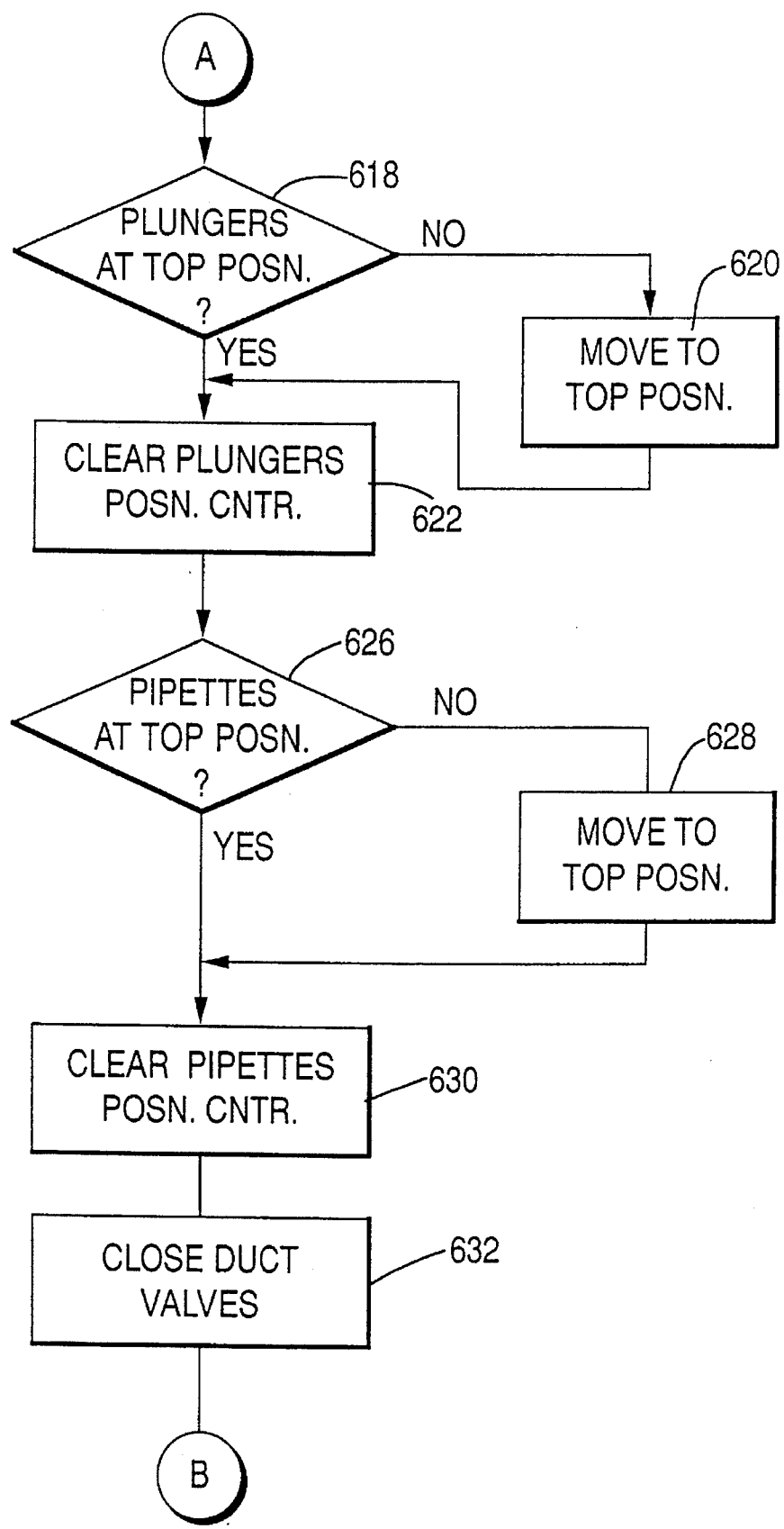
Figure 21C:
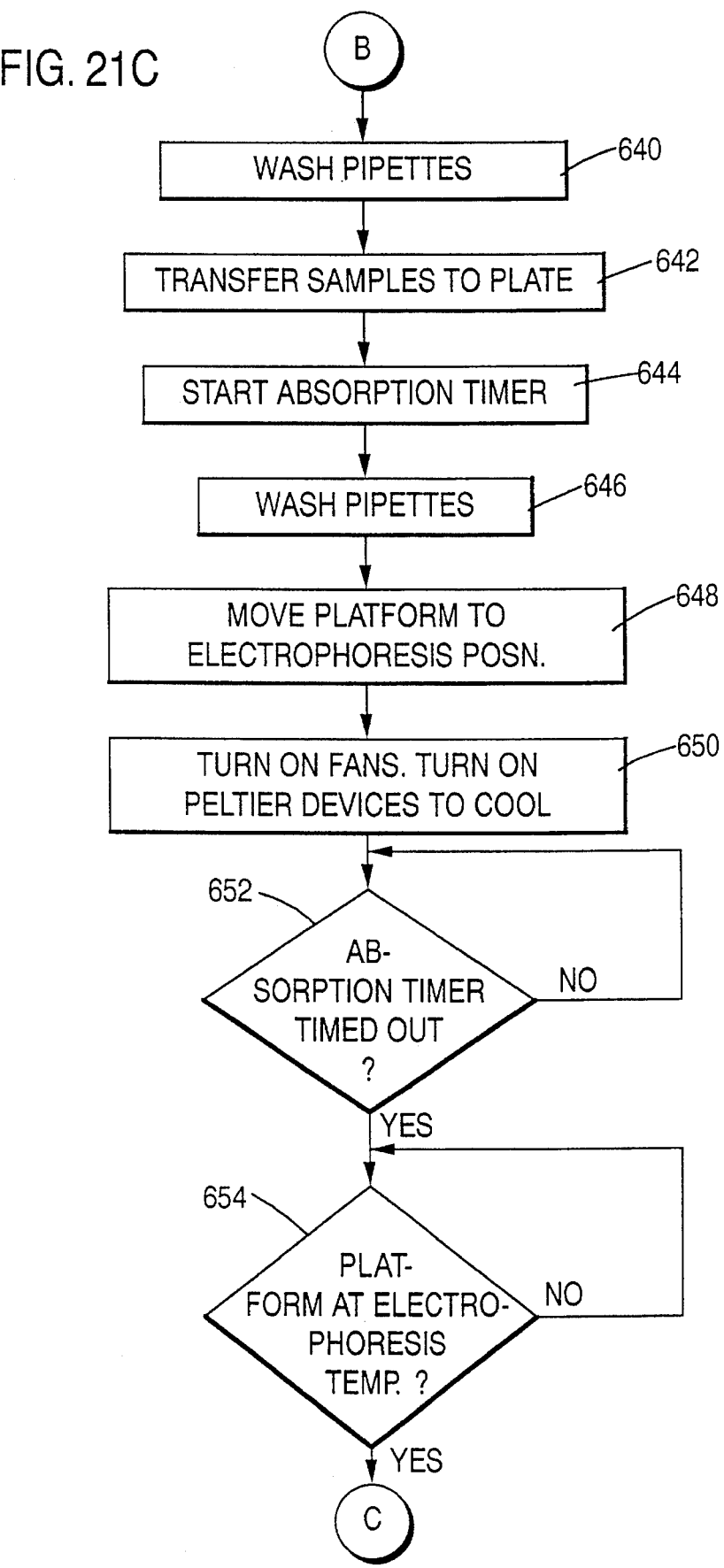
Figure 21D:
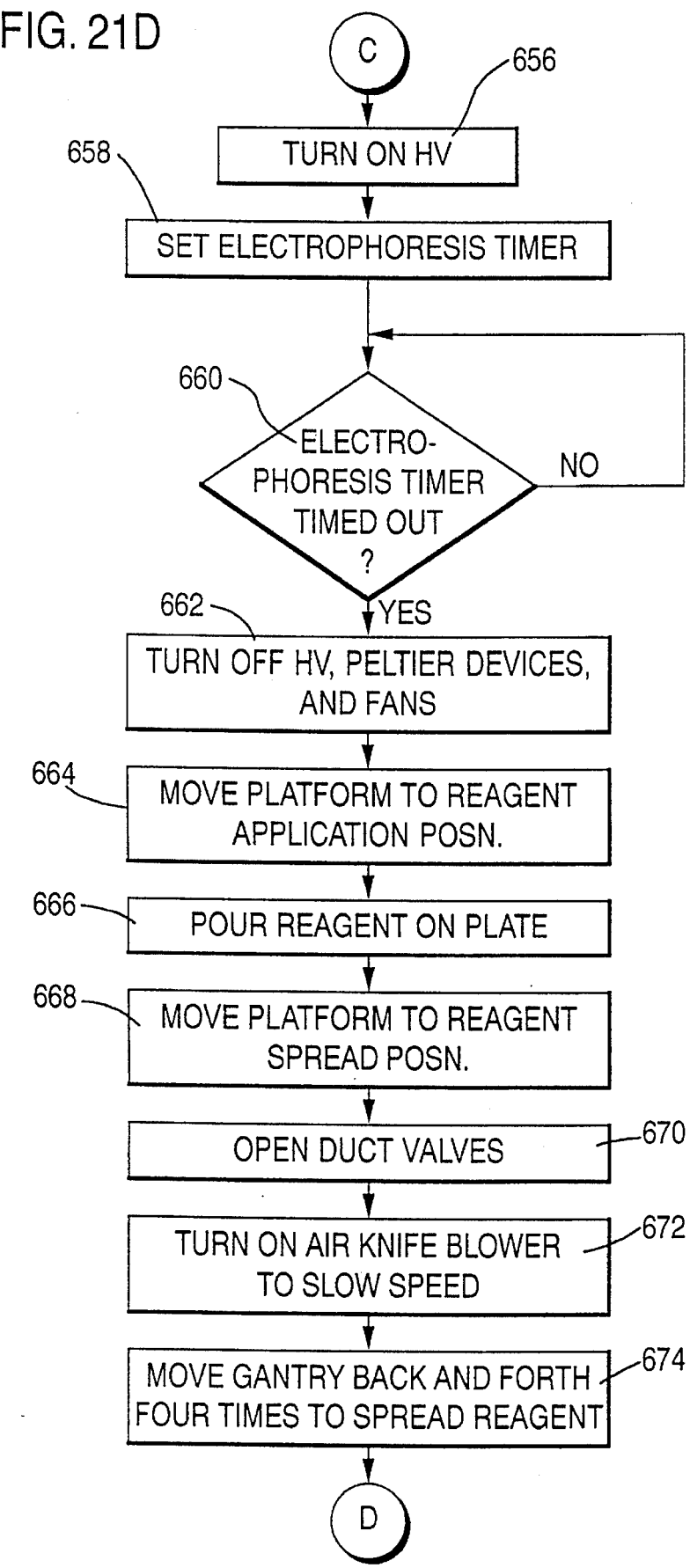
Figure 21E:
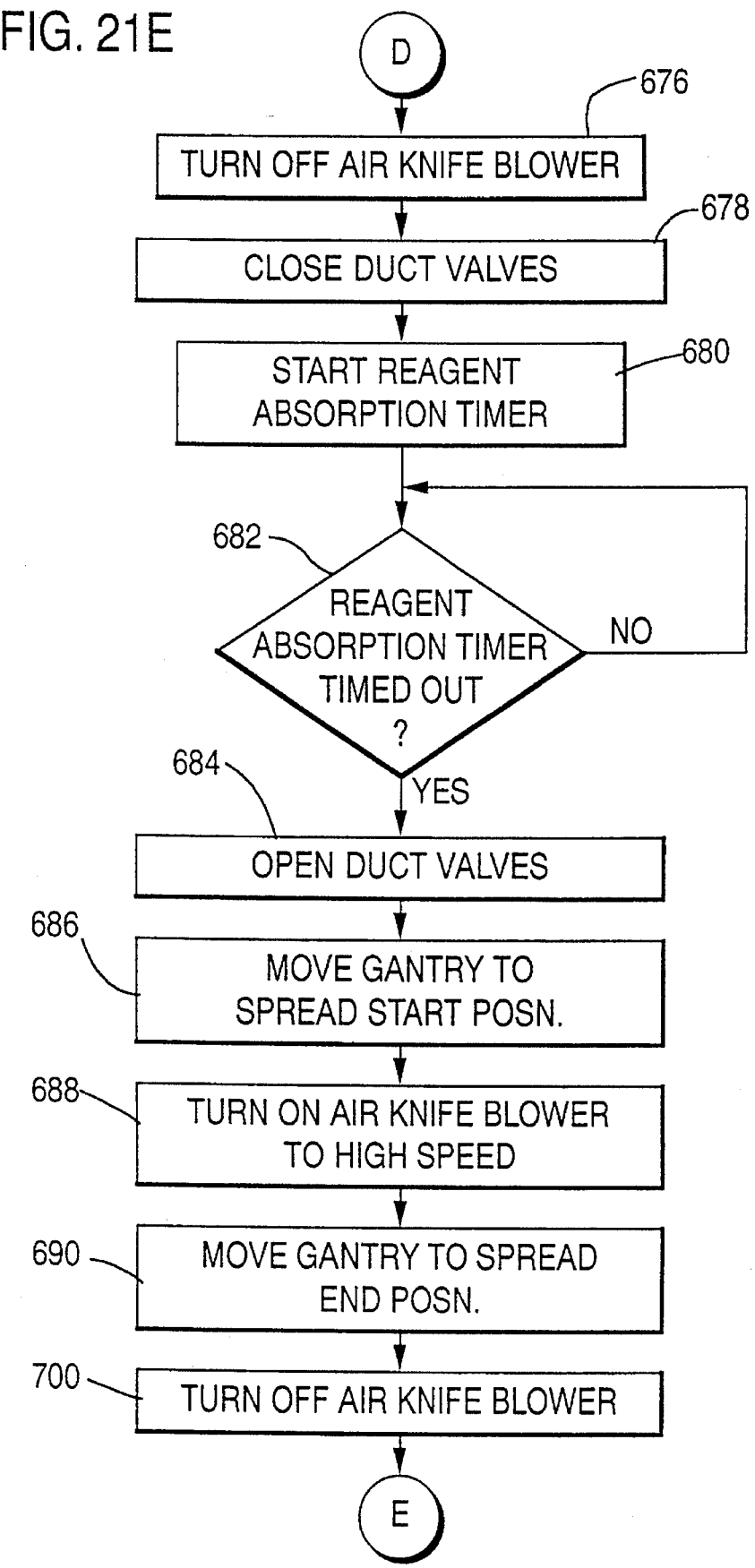
Figure 21F:
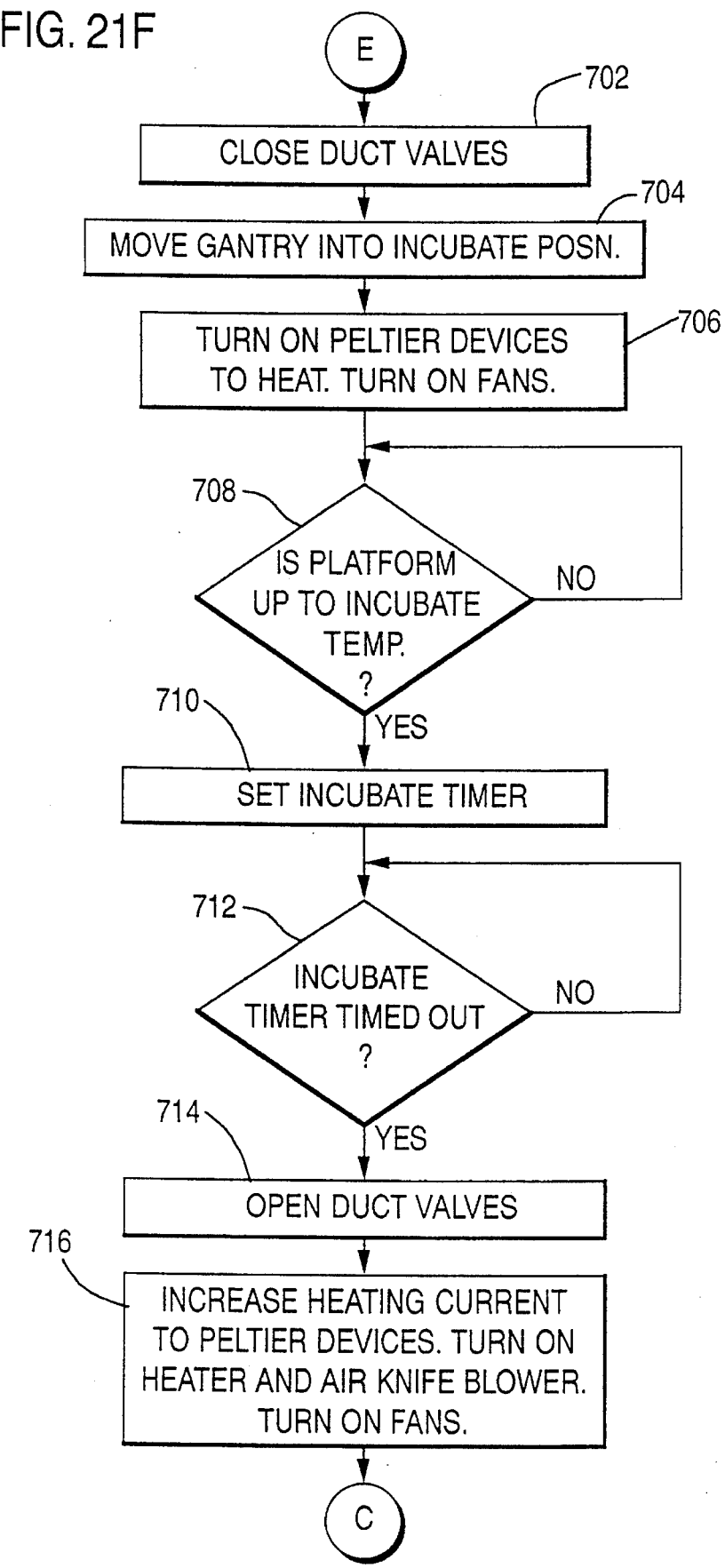
Figure 21G:
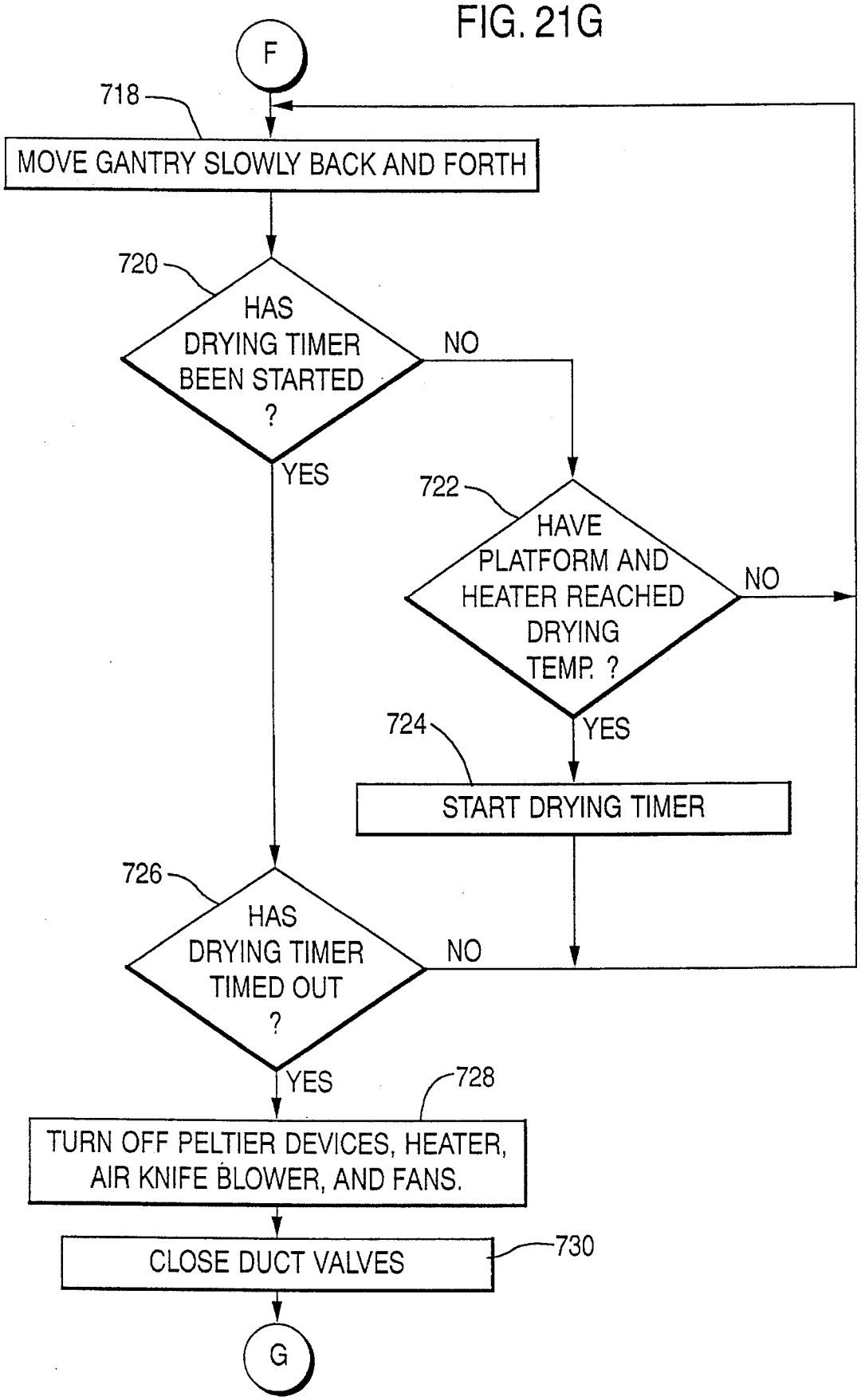

With reference to FIG. 21A, ultraviolet lamps 296 and photomultiplier tube 312 are turned on in step 600. The lamps and PMT need to warm up before they stabilize, so a warm-up timer is set to two minutes. Next, at step 602, the position of gantry assembly 56 is ascertained. If it is positioned at home switch 396 (see FIG. 16), a gantry position counter is cleared in step 604. If gantry assembly 56 is not located at switch 396 when step 602 is conducted, it is moved to that position in step 606 before the gantry position counter is cleared. The gantry position counter is an up/down counter which counts pulses from the position encoder 366 (see FIG. 20), counting up when gantry assembly 56 moves away from home switch 396 and counting down when it moves toward home switch 396, so after step 604 has been completed the content of the gantry position counter continuously corresponds to the position of gantry assembly 56 along gantry path 394. Gantry assembly 56 is moved in the right direction, to the position shown in FIG. 16, during step 608. This is done by using motor control circuit 546 (see FIG. 20) to drive motor 364 in the desired direction until the contents of the gantry position counter are equal to a previously-stored count value corresponding to the gantry position shown in FIG. 16.

Similarly, the position of electrophoresis platform 48 is ascertained in steps 610, and if it is not already located at home switch 392 (FIG. 16) it is moved there in step 612 before a platform position counter is cleared in step 614. Platform 48 is moved to the front position shown in FIG. 16 in step 616. Similarly, the position of plungers 440 (see FIG. 17) is checked in step 618, and if they are not at their top position they are moved to that position in step 620 before a plunger position counter is cleared in step 622. Like the remaining position counters to be described below, the plunger position counter and the platform position counter are up/down counters. In step 626 the position of pipette 52 (or, more accurately, barrels 422) is checked, and if they are not at their top position already they are moved there in step 628, after which a pipette position counter is cleared in step 630. Duct valve motors 230 (see FIGS. 7 and 20) are stepping motors which are over-driven in step 632 to ensure that duct valves 82 and 92 are at the closed position, regardless of their positions before step 632 was conducted. After step 632 has been completed, duct valves 82 and 92 can be opened or closed simply by driving motors 230 to move their shafts 234 a predetermined distance in the opened or closed direction.

Pipettes 52 are washed in step 640. With reference to FIGS. 2 and 16, this is done by moving electrophoresis platform 48 so that the trough 166 of washing solution is beneath pipettes 52, lowering the pipettes into the washing solution, reciprocating plungers 440 several times while the pipettes are immersed, raising the pipettes above trough 166 and lowering the plungers to expel any remaining washing solution, moving platform 48 until water trough 168 lies beneath pipettes 52, lowering the pipettes again and reciprocating the plungers several times, raising the pipettes and lowering the plungers to expel any remaining water, moving platform 48 until blotting region 172 lies beneath pipettes 52, lowering the pipettes to blot them against a strip of paper (not illustrated) deposited on region 172, and then raising the pipettes again.

In step 642 samples are transferred from a row of wells 162 on sample tray 158 to the corresponding wells 170 of electrophoresis plate 110 (see FIG. 4). Step 642 is conducted by moving electrophoresis platform 48 until the row of wells 162 lies beneath pipettes 52. The pipettes are then lowered into the wells. Plungers 440 are then raised to draw one microliter of fluid into each pipette, and the pipettes are then raised. Platform 48 is then moved so that pipettes 52 are above blotting region 172, whereupon the plungers are lowered to expel the samples onto the blotting paper. Platform 48 is then moved slightly so that a fresh region of the blotting paper lies beneath pipettes 52, which are then blotted against the paper. After the pipettes are raised, platform 48 is moved until the rows 162 again lie beneath pipettes 52. The pipettes are lowered into the wells and the plungers are raised to draw five microliters of fluid into each pipette. While the pipettes are still immersed, the plungers are lowered to expel the samples back into wells 162. This agitates the samples and removes any bubbles that may previously have been present. Then the plungers are raised to draw two microliters into each pipette. The pipettes themselves are then raised and one microliter is expelled back into the sample wells, leaving one microliter in each pipettes. Drawing in two microliters and expelling one helps to avoid bubbles at the lower ends of the pipettes. At this point the platform 48 is moved again until the wells 170 of electrophoresis plate 110 lie beneath pipettes 52. The plungers 440 are lowered first, so that a drop is formed on the end of each barrel 422, and then the barrels 442 are lowered so that the drops are placed in the sample wells 170. Precisely one microliter of fluid is transferred to each well 170.

It takes a certain amount of time for the samples in the wells 170 to diffuse into the electrophoresis medium layer 114. To this end, an absorption timer is set to a user-programmed value (a typical value would be a minute and a half) in step 644. The absorption time and other user-programmable values which will be discussed later are stored beforehand, replacing default values that were stored when apparatus 30 was manufactured. The pipette washing procedure is executed again in step 646 and thereafter electrophoresis platform 48 is moved to the electrophoresis position. As was mentioned before in conjunction with FIG. 16, platform 48 is moved to its electrophoresis position by moving it to the rear along platform path 390 until electrophoresis medium layer 114 lies directly beneath opening 272 in gantry assembly 56 when the gantry assembly is positioned at the right as shown in FIG. 16.

Fans 102 and 104 (see FIG. 3) are turned on in step 650. When platform 48 is in the electrophoresis position, heat sink fins 178 (see FIG. 6) are positioned in front of fans 102, and the air blown through fins 178 by fans 102 is collected by air outlet portion 98 of the air duct system and subsequently expel through air exit 106. Additionally, in step 650 the Peltier devices 186 (see FIG. 6) are turned on, with the polarity of the current supplied to the Peltier devices being such that their bottom surfaces are heated and their top surfaces are cooled. As a result, heat-transfer member 140 (see FIG. 6) begins to withdraw heat from electrophoresis plate 110.

In step 652, a check is made to determine whether the absorption time set by the absorption timer has expired. After expiration of this period a further check is made, at step 654, to determine whether platform temperature sensor 192 (see FIG. 19) has reached the temperature for conducting electrophoresis. Then electrophoresis power supply 64 is turned on in step 656 and an electrophoresis timer is set in step 658. A typical value for the voltage applied across electrodes 144 and 146 (see FIG. 5) would be 1500 volts, with a current of 30 milliamps. A typical electrophoresis time would be five minutes. During the electrophoresis operation the 45 watts dissipated in electrophoresis medium 114 is transferred by heat-transfer member 140 (see FIG. 6) and Peltier devices 186 to heat sink 176, and the air current through air duct inlet and outlet portions 96 and 98 (see FIG. 3) carries this heat away. As a result the electrophoresis medium layer 114 remains at the electrophoresis temperature despite the current flowing through it. Although not illustrated in the flow chart, monitor 528 (see FIG. 19) continuously monitors the electrophoresis voltage and current throughout the electrophoresis procedure.

After the electrophoresis time has expired (step 660), electrophoresis power supply 64, fans 102 and 104, and Peltier devices 186 are turned off (step 662). In step 664 the electrophoresis platform 48 is moved forward to the reagent application position, beneath reagent pouring station 54. Reagent drive motor 258 (FIG. 8) is then actuated to invert vial 240 (step 666). Platform 48 is then moved to the rear along platform path 390 until it reaches the reagent spread position (step 668), which is the same as the electrophoresis position. Duct valves 82 and 92 (see FIG. 3) are then opened (step 670) and air knife blower 340 (see FIG. 14) is turned on to a slow speed (step 672). Air is drawn through air inlet portion 74 (FIG. 3), bellows 86 (FIG. 15), and into air guide 316 (FIG. 14) of gantry assembly 56. This air is directed against electrophoresis plate 110 through air knife slot 338 (FIG. 14) and is then removed via air guide 324 of gantry assembly 56, bellows 88 (FIG. 15), and air duct outlet portion 76 (FIG. 3). Gantry assembly 56 is moved back and forth four times (step 674) to permit the air knife to spread the reagent over portion 120 (see FIG. 4) of electrophoresis medium layer 114. Then air knife blower 340 is turned off (step 676), duct valves 82 and 92 are closed again to pneumatically isolate gantry assembly 56 from the external atmosphere (step 678), and a reagent absorption timer is started to time a two minute period for the reagent to be absorbed (step 680).

After the two minute absorption period has expired (step 682), duct valves 82 and 92 are opened again (step 684). In step 686 gantry assembly 56 is moved to a spread start position. With reference to FIG. 16, in the spread start position air knife slot 338 lies to the right of electrophoresis medium layer 114. Air knife blower 340 is then turned on at a high speed in step 688 and gantry assembly 56 is moved to a spread end position, in which air knife slot 338 is positioned to the left of electrophoresis medium layer 114. Thus the air knife makes one sweep across electrophoresis medium layer 114 and the air blows at a relatively high speed to remove the reagent remaining on electrophoresis medium layer 114. Blower 340 is turned off in step 700. During operation of the air knife (steps 672–676 and, particularly steps 686–700) the reagent blown from electrophoresis plate 110 accumulates in troughs 136 (see, for example, FIG. 16). Duct valves 82 and 92 are closed in step 702.

Electrophoresis plate 110 must then be incubated while the reagent chemically combines with the isoenzymes that have been separated by the electrophoresis procedure. Gantry assembly 56 is moved to an incubation position (which is the same as the electrophoresis position) in step 704. Peltier devices 186 are turned on in step 706, with the polarity of the current being such that electrophoresis plate 110 is heated. Furthermore, fans 102 and 104 are turned on to blow air across the heat sink fins 178 (see FIG. 6). In step 708 a check is made to determine whether electrophoresis platform 48 (or, more accurately, platform temperature sensor 192 as shown in FIG. 19) is up to the incubation temperature of 45° C. An incubation timer is set in steps 710 after the temperature reaches a user-programmed value (such as 45° C.). The time set by the incubation timer is also user-programmable (a typical time would be five minutes).

Duct valves 82 and 92 are opened in step 714 after the incubation period has expired. In a matter analogous to the fixing step during photographic processing, the electrophoresis medium layer 114 must now be dried to halt the chemical reaction between the reagent and the isoenzymes. In step 716 the heating current to Peltier devices 186 is increased and, furthermore, heater 342 (see FIG. 14) is turned on. Air knife blower 340 is also turned on. Furthermore fans 102 and 104 are turned on to blow air across heat sink fins 178. Gantry assembly 56 is moved slowly back and forth across electrophoresis plate 110 during step 718.

The drying temperature and the drying time are user-programmable. Typical values would be 54° C. and two minutes, respectively. In step 720 a check is made to determine whether a drying timer has been started. If not, a check is made in step 722 to determine whether platform temperature sensor 192 (see FIG. 19) and gantry temperature sensor 443 have reached the drying temperature. The drying timer is started in step 724 after the drying temperature has been reached.

Returning to step 720, after the drying timer has been started a check is made at step 726 to determine whether it has timed out. Peltier devices 186, gantry heater 342, air knife blower 340, and fans 102 and 104 are turned off after the drying time has expired, and duct valves 82 and 92 are closed again (step 728 and 730).

The voltage supplied to the anode of photomultiplier tube 312 must be set before PMT 312 is used to collect data from electrophoresis plate 110. The gain of a PMT is a function of the anode voltage. The general equation for the gain G is set forth in Equation 1:

$$G = kV^{\alpha n} \qquad (1)$$

In Equation 1, V represents the anode voltage, n represents the number of stages in the photomultiplier tube, and k and $\alpha$ are constants which are available from the manufacturer of the tube. The PMT 312 is preferably a nine stage tube (n=9) available from Hamamatsu Photonics K. K. of Japan, with a US sales office at 360 Foothill Road, P.O. Box 6910, Bridgewater, N.J. 08807.

As was mentioned earlier the gain of PMT amplifier 520 (see FIG. 19) is adjustable. However it is desirable for PMT tube 312 itself to contribute a substantial portion of the overall gain in order to achieve a good signal to noise ratio.

Figure 19:
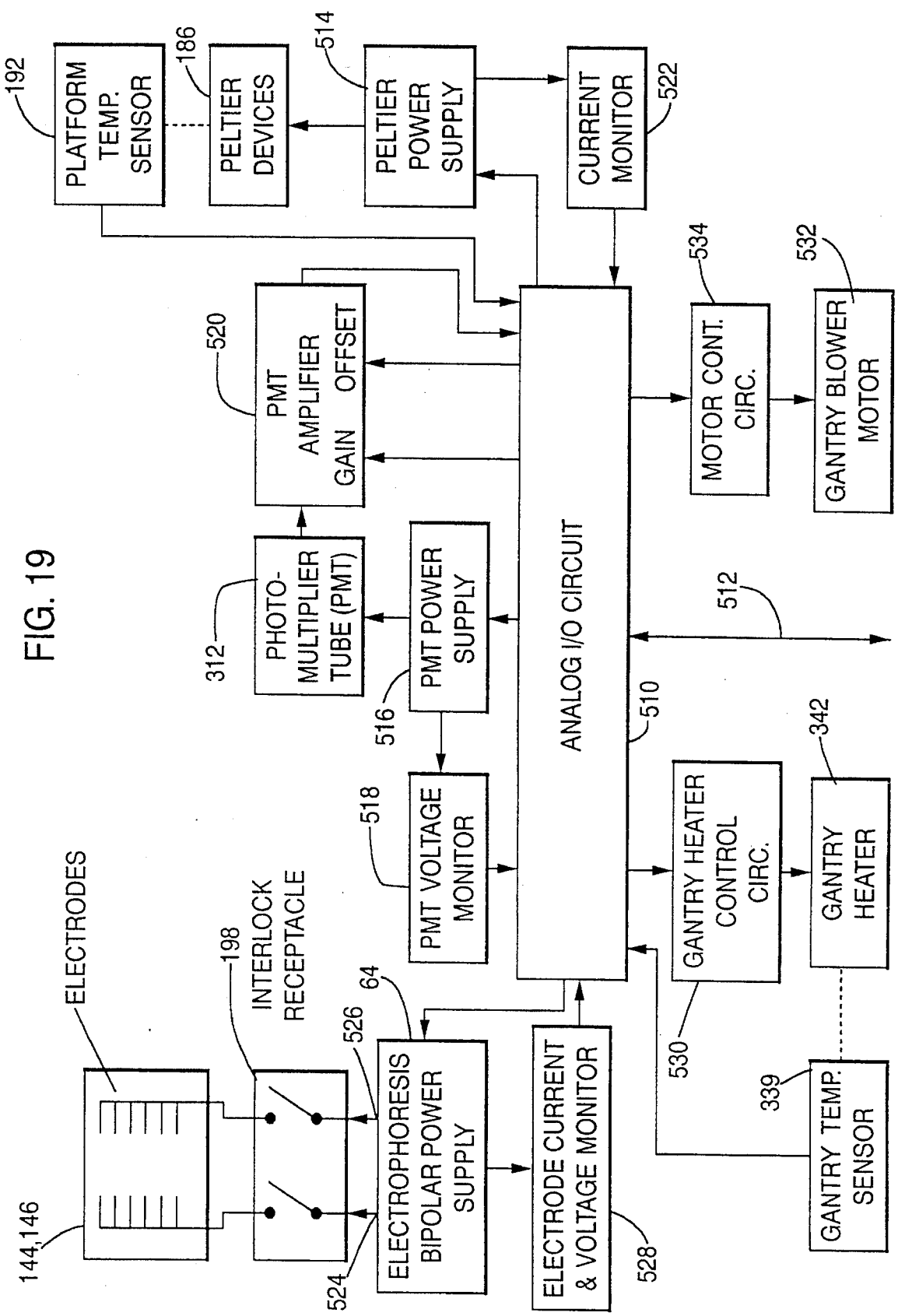

Although not illustrated in FIG. 19, analog I/O circuit 510 includes an A/D converter which receives the output of amplifier 520. This A/D converter is capable of converting analog signals in the minus five volts to plus five volts range to twelve bit digital signals, plus a sign bit. That is, the A/D converter is capable of dividing an input signal into 1.22 millivolt segments, with $2^{12}$ (=4096) such segments being available. A malfunction would occur if the absolute value of the output signal from amplifier 520 to the A/D converter exceeded five volts, which will hereafter be call the "full scale" value. Plus five volts will be called the "positive" full scale value.

In accordance with the present invention, the anode voltage of PMT 312 is initially set at a relatively high value to obtain a relatively high gain. Then the six tracks 388 (see FIG. 16) are scanned sequentially. Each time the measured value (that is, the output of amplifier 520) exceeds some predetermined fraction of the full scale value, a new gain is calculated and a reduced voltage is applied to PMT 312 to achieve a reduced gain. The new gain is found by dividing the measured value into a reduction factor, expressed as a fraction of full scale, and by multiplying the quotient by the old gain. This is shown in Equation 2.

$$G_{new} = G_{old} \times \frac{R}{M} \qquad (2)$$

In Equation 2, R represents the reduction factor and M represents the measured value. In electrophoresis apparatus 30, M has been selected to be one-half of the positive full scale value, or 2.5 volts, and R has been selected to be one-fourth of the positive full scale value, or 1.25 volts. Accordingly, each time the measured value exceeds 2.5 volts, a new gain which does not exceed one-half the old gain is calculated, with the exact value of the new gain depending upon the measured value.

The voltage that needs to be applied to the anode of PMT 312 to achieve the desired gain can be determined by solving Equation 1. This voltage is shown in Equation 3.

$$V = \left( \frac{G}{K} \right)^{\frac{1}{\varpi}} \qquad (3)$$

In Equation 3, the gain value G is, of course, the new gain.

Figure 21H:
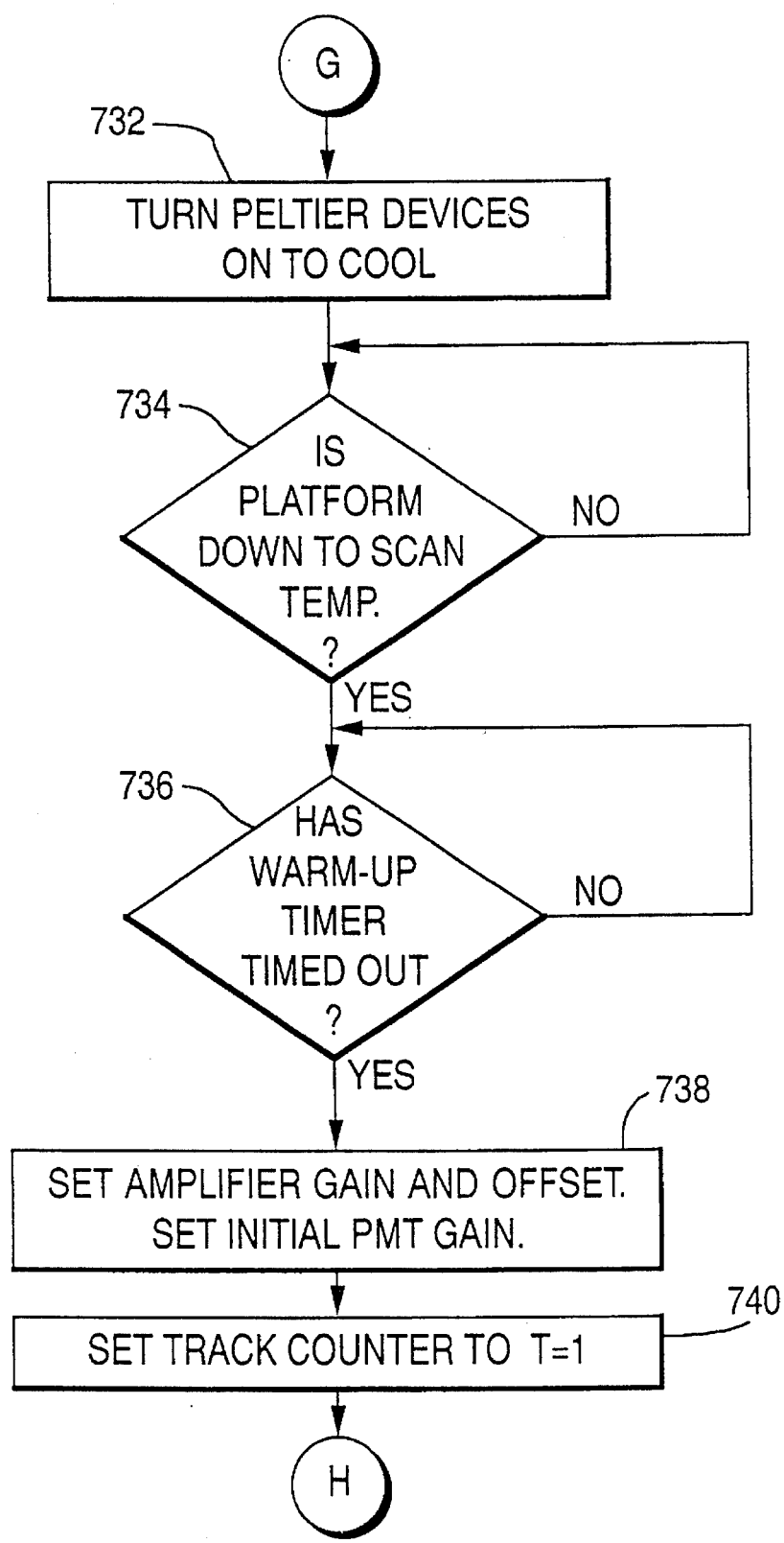
Figure 21I:
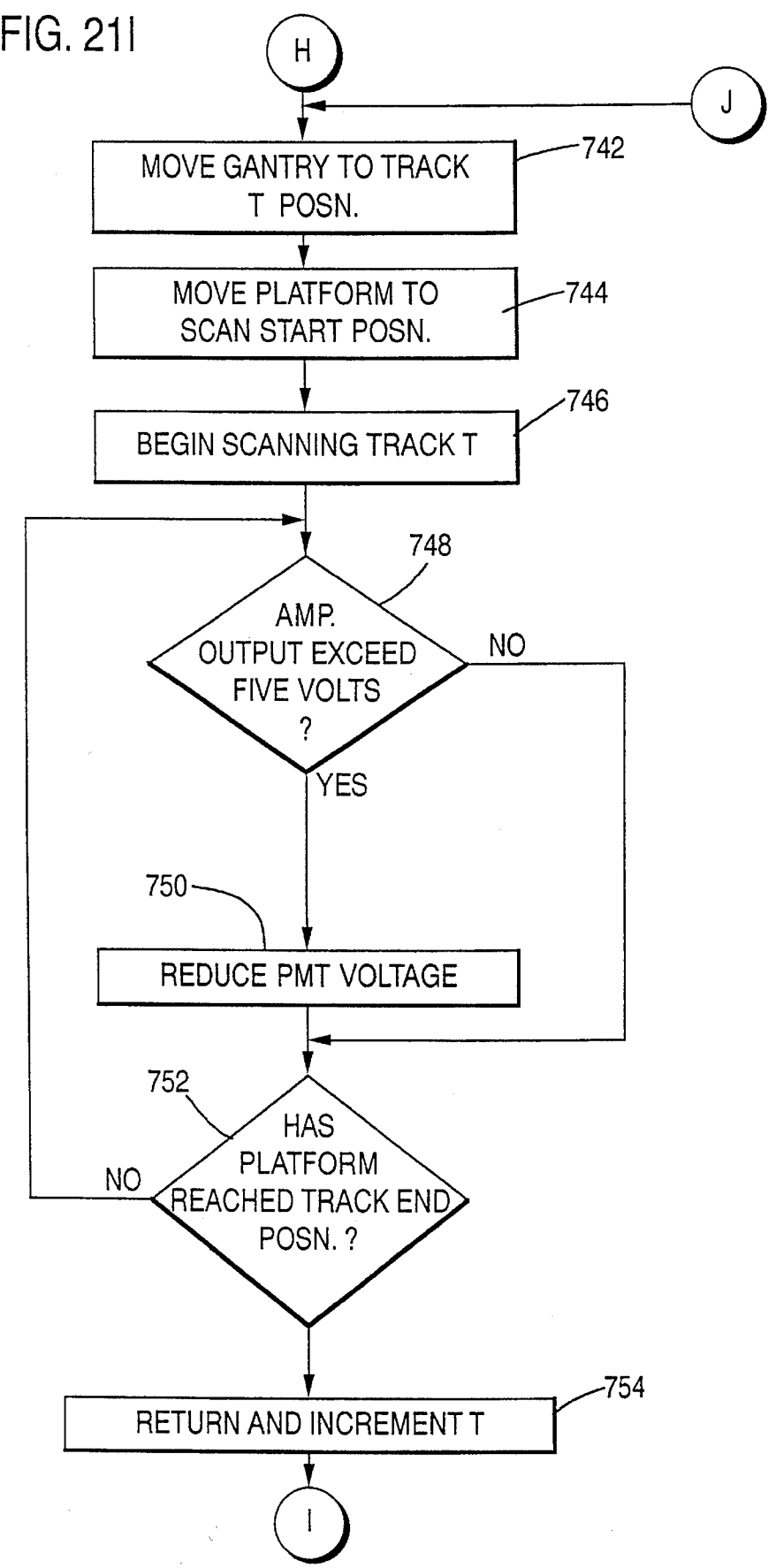
Figure 21J:
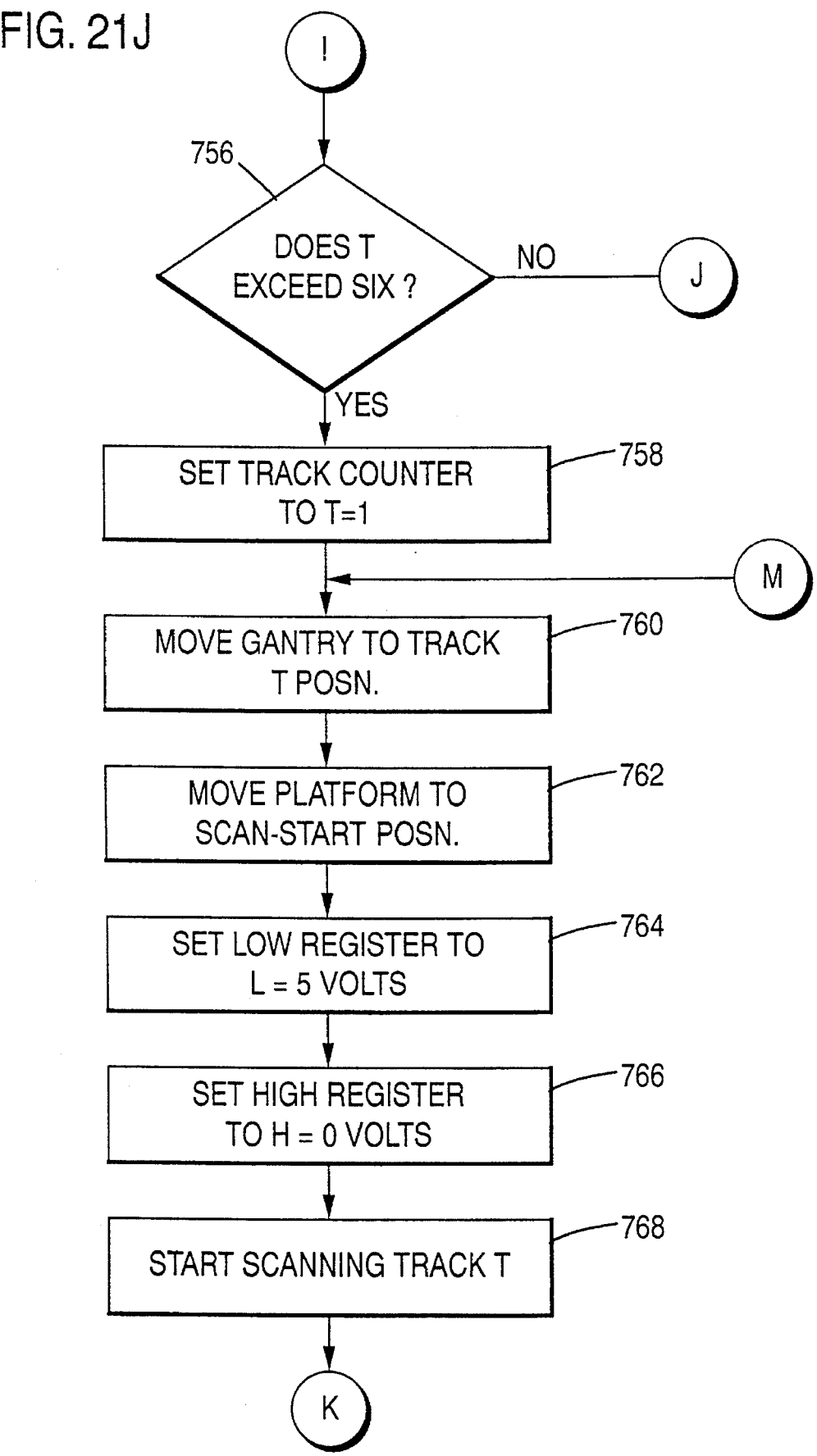
Figure 21K:
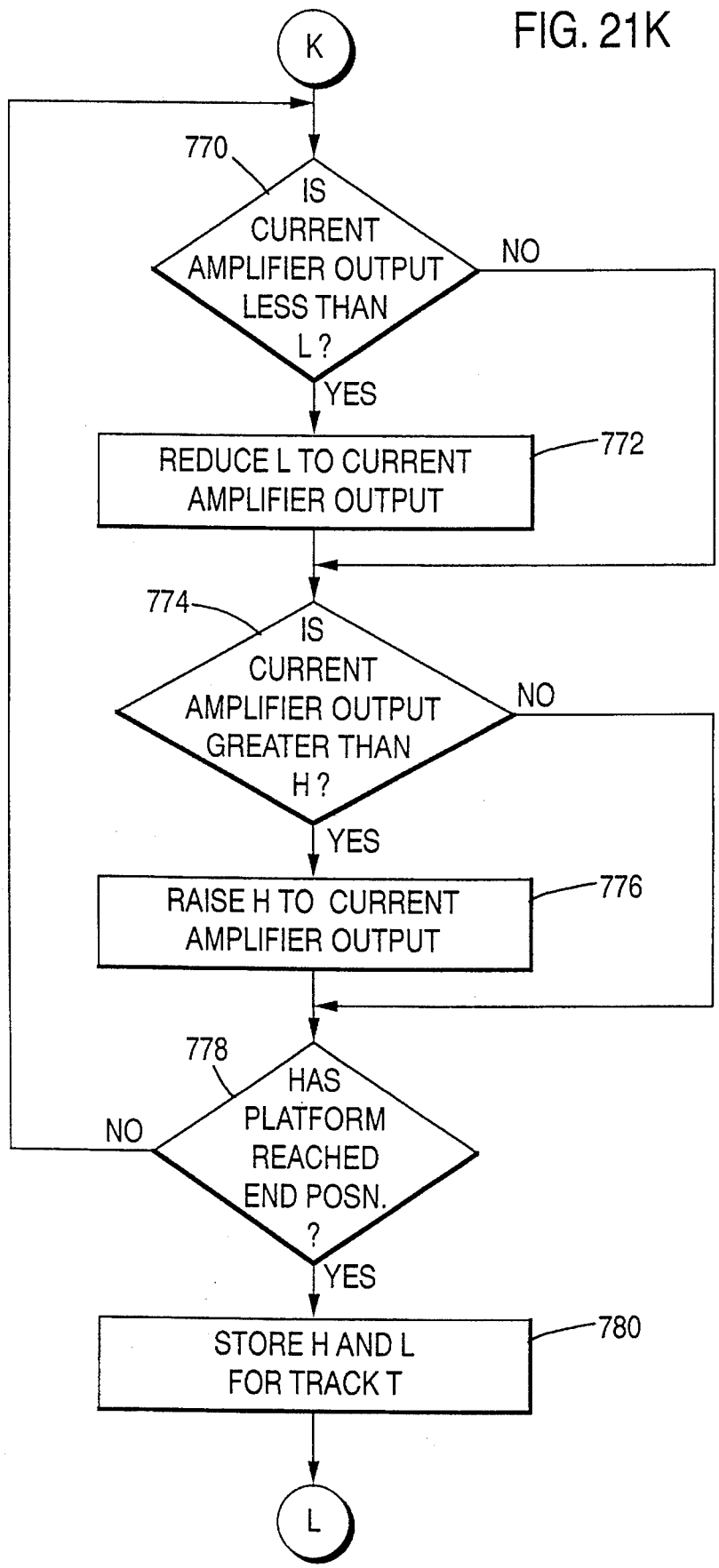
Figure 21L:
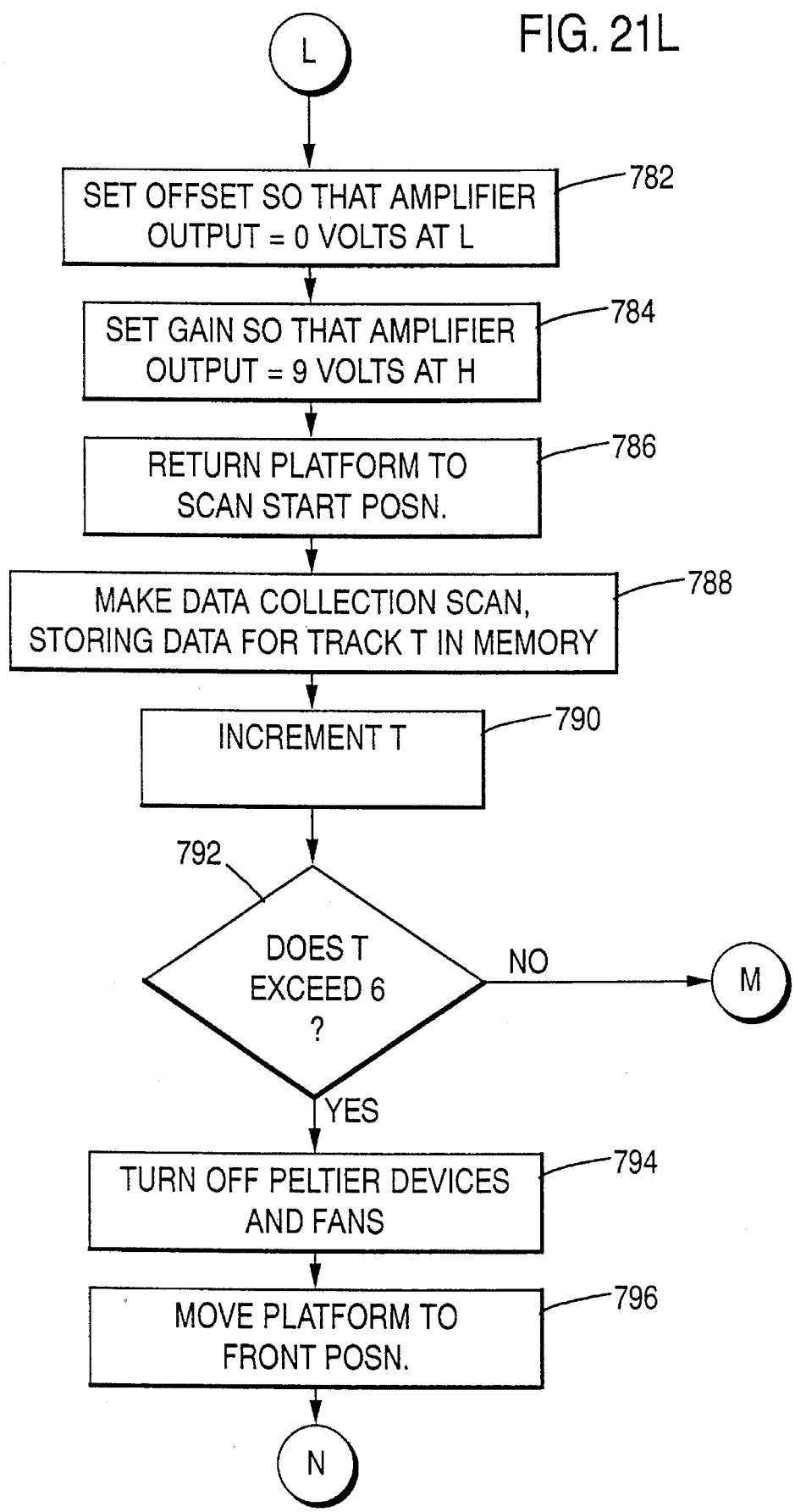
Figure 21M:
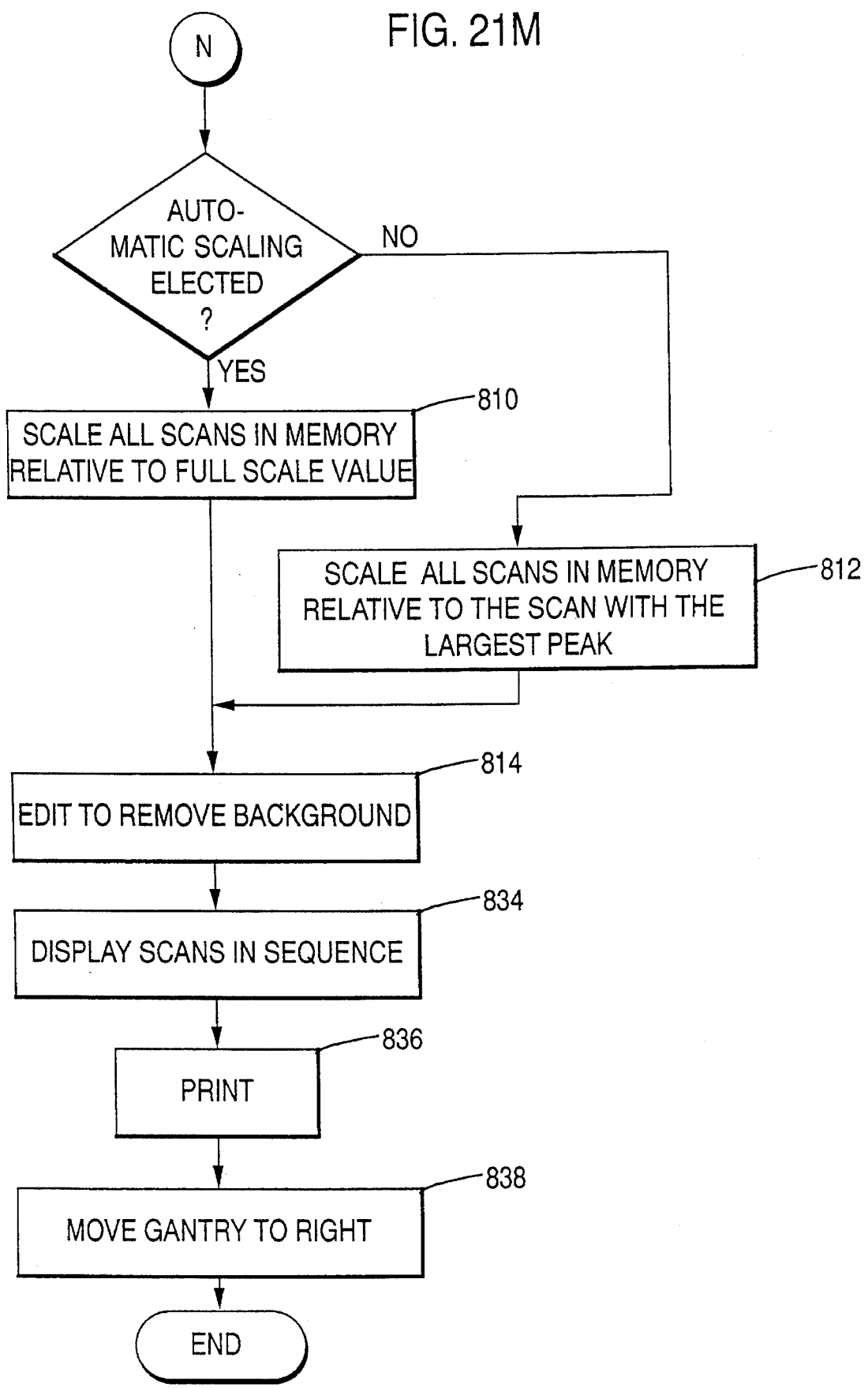

In FIG. 21H, Peltier devices 186 are turned on to cool electrophoresis plate 110 in step 732. In step 734 a check is made to determine whether platform temperature sensor 192 (FIG. 19) is down to the scan temperature (200° C.). When it has reached the scan temperature, a further check is made at step 736 to determine whether the warm-up timer that was set in step 600 has timed out. Then the gain of PMT amplifier 520 is set to one and the offset is set to zero in step 738. Additionally, the anode voltage is set at 647 volts for an initial PMT gain of approximately 400 with the tube that is used. In step 740 a track counter is set to one. Track one is the right-most track 388 shown in FIG. 16. Track six is the left-most track 388.

Gantry assembly 56 is moved so that slit 282 is aligned with track one in step 742. In step 744 electrophoresis platform 48 is moved to the scan start position. In the scan start position slit 282 is located before the tracks begin, below wells 170 as depicted in FIG. 16. Platform 48 begins moving toward the front of apparatus 30 in step 746 to begin scanning track one. The reagent that is bound to the isoforms along track one fluoresces under the influence of ultraviolet lamps 296 (see FIG. 13, for example), and collimator 280 (see FIG. 11) permits fluorescent light that is emitted directly beneath it in a direction perpendicular to electrophoresis plate 110 to reach PMT 312. The output of PMT 312 is amplified by PMT amplifier 520, the output of which is monitored during the scan. If the output of amplifier 520 exceeds 2.5 volts (that is, half of the positive full scale value), the anode voltage on PMT 312 is reduced (as previously discussed) in step 750 to reduce the PMT gain. A check is made, at step 752, to determine whether platform 48 has reached the track end position. In FIG. 16, the track end position is located above the dot-dash chain lines that are used to depict tracks 388. After it reaches the track end position, platform 48 returns at a relatively high speed to the track start position (step 754) and the track counter is incremented. In step 756 a check is made to determine whether the track number exceeds six. If not, further tracks remain to be scanned and processing returns to step 742. The brightest point on plate 110 will lead to an amplifier output between 1.25 and 2.5 volts after all six tracks have been scanned.

After the anode voltage for the PMT has been set, the gain and offset of PMT amplifier 520 are set on a track-by-track basis, with a data-gathering run being made over each track after the gain and offset have been set. To do this, the track counter is set again to one in step 758, and gantry assembly 56 is moved again to the track one position in step 760. Platform 48 is moved to the scan-start position in step 762. Initial values for a low register and a high register are set in steps 764 and 766 and platform 48 begins moving toward the front of apparatus 30 in step 768 to begin scanning track one. A check is made in step 770 to determine whether the present or current output of PMT amplifier 520 is greater than the value stored in the low register; if so, the value stored in the low register is replaced by the present or current output of amplifier 520 in step 772. A check is then made in step 774 to determine whether the present or current output of amplifier 520 is higher than the value stored in the high register, and if so the old value is replaced by the present value in step 776. The high and low values detected during the scan are stored after platform 48 has reached its end position (step 778 and 780). Then the offset of amplifier 520 is set so that the amplifier output is zero at the lowest point detected during the scan and the amplifier gain is set so that the highest point detected during the scan leads to an output of 4.5 volts (steps 782 and 784). Platform 48 is returned to the scan start position in step 786. Then a data collection scan is made in step 778, and the data is stored. The track counter is incremented at step 790, and a check is made at step 792 to determine whether the last track has been read. If not, processing returns to step 760. Peltier devices 186 and fans 102 and 104 are turned off (step 794) after the last track has been read, and platform 48 is returned to its final position at the front of apparatus 30 (step 796).

How the results of the measurements are to be presented is a user-programmable option. The testing facility at which apparatus 30 is employed can elect to have the results automatically scaled or to have them graphically expressed in international units. This election is made beforehand, and if automatic scaling is elected the user also selects the number of international units that are to represent full scale. During an assay, a check is made at step 800 to determine if the results are to be depicted in international units. If so, all six stored scans are scaled in step 810 relative to the selected full-scale value. If the results are to be automatically scaled ("no" in step 800), the stored scans are all scaled relative to the largest peak in step 812. After scaling (steps 810 or 812), the stored values are edited in step 814 to remove background noise and unwanted signals.

Figure 22:
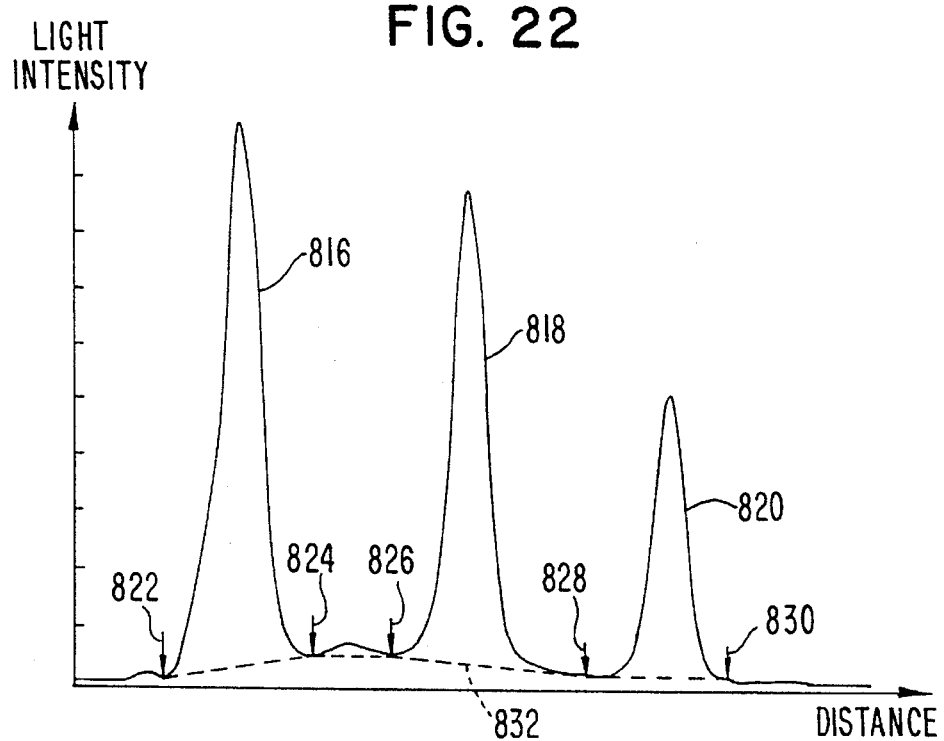
FIG. 22 is a graph illustrating an example of data collected by the electrophoresis apparatus before automatic editing.

Step 814 will be described in more detail with reference to FIG. 22, a graph showing an example of a scan of one track. In FIG. 22, the ordinate axis represents the intensity of the light detected by photomultiplier tube 312 and the abscissa axis represents the distance along the relevant track 388. The graph shown represents a scan scaled relative to the largest peak (step 812). Spike 816 represents the MM isoenzyme of creatine kinase. Spike 818 represents the MB isoenzyme, and spike 820 represents the BB isoenzyme.

There are three main sources of background noise. One is airborne lint. Many laundry detergents employ fluorescent materials as brighteners, so an errant fiber from clothing may produce a spurious signal if it happens to fall on one of the tracks 388. Albumin is another potential source of background noise. It is normally present in blood serum or plasma but ordinarily does not cause problems during an assay of the isoenzymes of creatine kinase. The reason is that normal albumin does not chemically combine with the reagent used in such an assay. However a modified form of albumin which is naturally fluorescent may be present in the blood of kidney patients or patients taking an anti-clotting drug.

The third potential major source of background noise is macro creatine kinase, which is also naturally fluorescent under ultraviolet light. Macro creatine kinase results when certain antibodies bind to creatine kinase, as occasionally happens in elderly patients with certain auto-immune disorders.

The first order of defense employed by electrophoresis apparatus 30 against background noise arising from airborne contaminants is avoidance. Duct valves 82 and 92 (see FIG. 3) mechanically isolate electrophoresis plate 110 from the ambient atmosphere during major portions of the analytic procedure described above. The risk of contamination is reduced accordingly. The duct valves are open only when this is necessary for operation of air knife blower 340 (see FIG. 14).

Even if electrophoresis plate 110 does become contaminated with lint, perhaps when the operator installed plate 110 in apparatus 30 or during the initial portion of the automatic operation of apparatus 30 before electrophoresis platform 48 is withdrawn into the machine, it is frequently possible to remove the resulting background noise electronically. Arrows 822, 824, 826, 828 and 850 have been added to FIG. 22 to mark the minima of the curve. These minima are identified by detecting where the slope of the curve changes from negative to positive. Since spikes 816, 828, 820 lie at approximately the same positions on the distance axis from one assay to the next when the electrophoresis conditions are constant, as they are in apparatus 30, any peaks that lie outside spikes 816, 818, and 820 can be eliminated as spurious. For example, the small peak shown between arrows 824 and 826 may be due to dust or some other cause such as macro creatine kinase, but it is definitely not attributable to the MM, MB or BB isoenzyme of creatine kinase. Such out-of-position peaks are eliminated during editing step 814.

Furthermore, during editing step 814 a baseline 832 which passes through the minima identified by arrows 816, 828, 820 is also calculated. The area beneath baseline 832 may, for example, represent a spurious signal due to a modified form of albumin present in the patient's blood. Baseline 832 is subtracted from spikes 816, 818, and 820 during editing step 814.

While background noise due to modified forms of albumin can be edited electronically by determining a baseline as noted above, the problem can be eliminated chemically as an alternative. Methyl red, a Ph indicator dye, binds tightly with albumin and displaces whatever substances may previously have been bound to it. Albumin bound to methyl red does not fluoresce and in fact absorbs ultraviolet light. Accordingly, background noise due to modified albumin can be avoided by adding one percent by volume of methyl red to the patient's serum and waiting five minutes for it to bind before beginning the electrophoresis procedure. It is believed that a reduction in albumin-origin noise could also be achieved by including the Ph indicator dye in the electrophoresis medium layer of the electrophoresis plate or in the reagent. Methyl orange can also be used, but superior results are obtained with methyl red.

Figure 23:
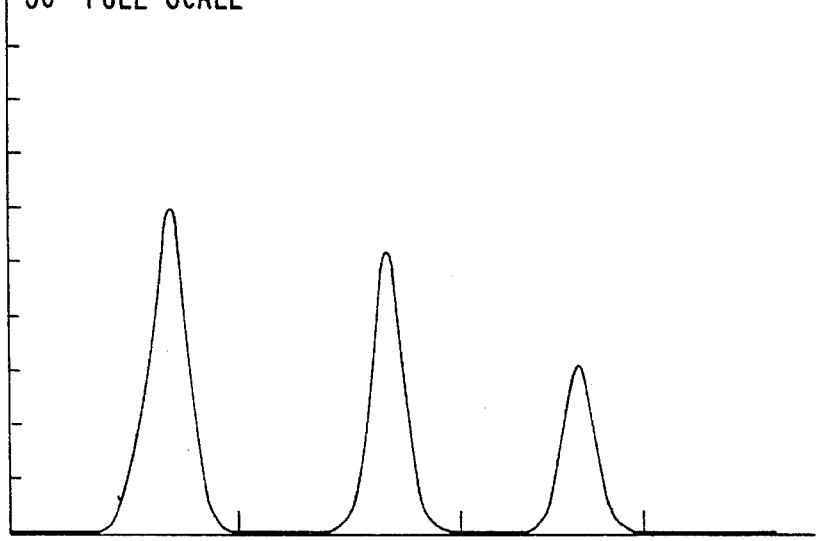
FIG. 23 is a graph illustrating the edited data, scaled to show international units on the vertical axis.
Figure 24:
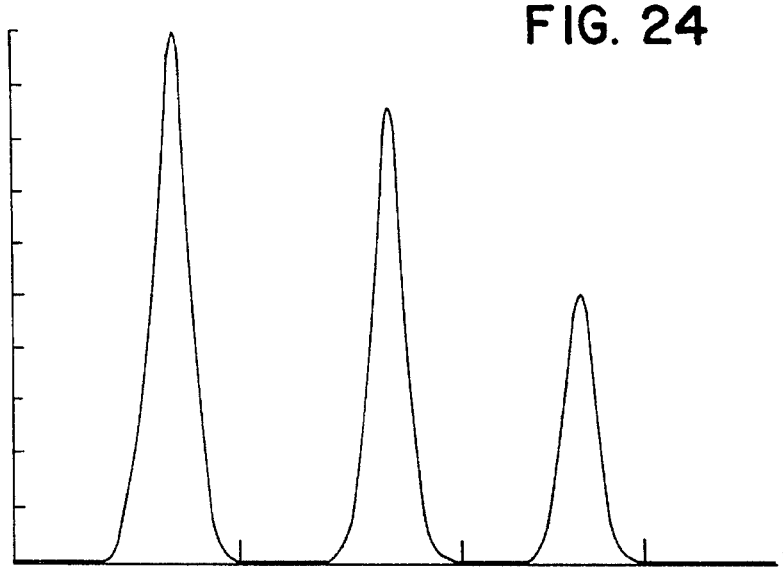
FIG. 24 is a graph illustrating the edited data, scaled so that the most prevalent isoenzyme is depicted at 100% full scale.

The six edited scans are displayed sequentially on video monitor 34 (see FIG. 1) in step 834 and printed by printer 36 in step 836. FIG. 23 illustrates the video display and hard copy corresponding to the un-edited scan depicted in FIG. 22 if the option to have the results expressed in international units is elected and if 50 international units are selected to represent full scale. FIG. 24 illustrates the same information if the option to have the results automatically scaled is elected. In both cases, quantitative measures of the relative percentages of the three fractions and the international units are preferably also depicted, as illustrated.

Finally, in step 838 gantry assembly 56 is returned to its original position in preparation for the next run.

While the program of FIGS. 21A–21M has been described in the context of an assay of creatine kinase, apparatus 30 can assay other substances, such as lactate dehydrogenase. A lactate dehydrogenase assay is useful to physicians when diagnosing heart or kidney ailments.

Electrophoresis plate 110 (FIG. 4) is typically packaged with a protective plastic film (not illustrated) on central portion 120. Due to a phenomenon known as syneresis, liquid is expressed from the electrophoresis medium layer and accumulates under the protective film. As was noted previously, the electrophoresis medium layer preferably includes a surfactant such a methyl cellulose, which alters the surface tension of the electrophoresis medium layer and causes the accumulated liquid to wet central portion 120 in a uniform film when the protective plastic film is removed prior to use of electrophoresis plate 110. Otherwise, the expressed liquid remaining on central portion 120 would form thin, irregular patches when the protective plastic film is removed and these irregular patches would have to be removed prior to use of plate 110 in order to keep them from undermining the electrical homogeneity of the electrophoresis medium layer. Typically the operator removes irregular patches of liquid from an electrophoresis plate that lacks a surfactant such as methyl cellulose by blowing them away, for example, or by blotting the electrophoresis plate.

If electrophoresis plates 110 without methyl cellulose are used with electrophoresis apparatus 30, the program illustrated in FIGS. 21A–21M can readily be modified to remove the irregular patches of liquid automatically in a preliminary step. This is accomplished using the air knife, with blower 340 operating at high speed as gantry assembly 56 sweeps back and forth over electrophoresis plate 110.

It will be apparent that information about various aspects of electrophoresis apparatus 30 is needed by computer 62 during execution of the program shown in FIGS. 21A–21M. Some of this information is very accurately known at the time apparatus 30 is made. For example, due to mechanical considerations the distance moved by gantry assembly 56 during successive pulses from encoder 366 (see FIG. 19) is known with precision and can be stored in hard disk 504 (see FIG. 17) during manufacture of apparatus 30 for use throughout the life of apparatus 30. Other values needed during execution of the program are not precisely known during manufacture due to variations in individual components and due to manufacturing tolerances when electrophoresis apparatus 30 is constructed. For example, the performance of commercially available temperature sensors may vary slightly from one sensor to the next, and the exact position of slit 282 (see FIG. 16) when it is over a predetermined track 388, in terms of encoder pulses from home switch 396, depends upon precisely how the relative components are mounted in electrophoresis apparatus 30 and may vary slightly from one apparatus 30 to the next. Approximately correct default values for such parameters are stored in hard disk 504 when apparatus 30 is made, and it is desirable to calibrate apparatus 30 prior to use to replace these default values with more accurate values. Calibration procedures will be described below. Another class of information stored in hard disk 504 need not be known with extreme accuracy (e.g., the exact position of electrophoresis platform 48 in terms of encoder pulses from home switch 392 when the reagent is poured at station 54) or can be accurately determined from the calibrated values (e.g., the position of electrophoresis platform 48 during the electrophoresis procedure, in terms of counted encoder pulses from home switch 392).

Figure 25A:
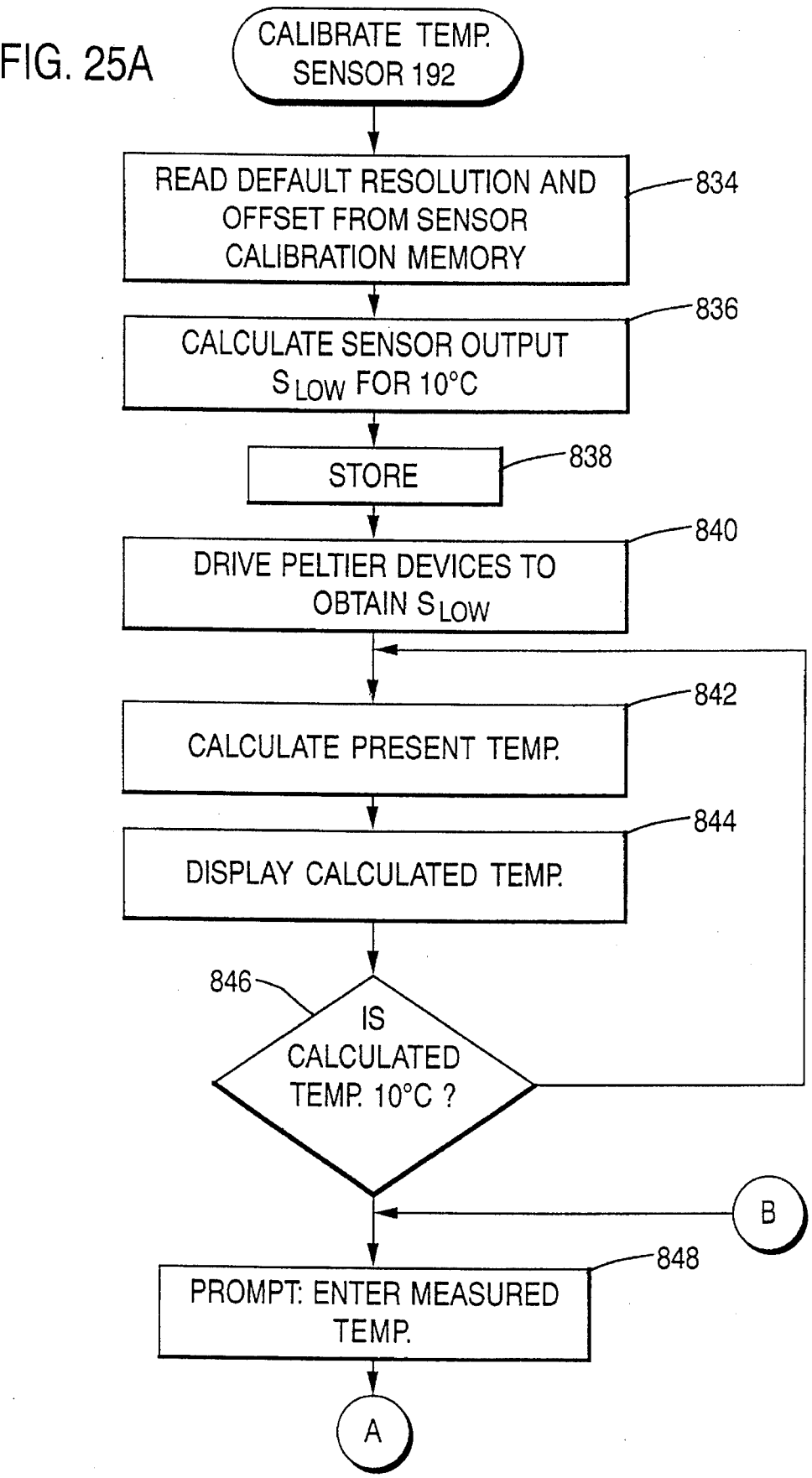
FIGS. 25A–25C illustrate a flow chart for calibrating a temperature sensor in the electrophoresis apparatus.
Figure 25B:
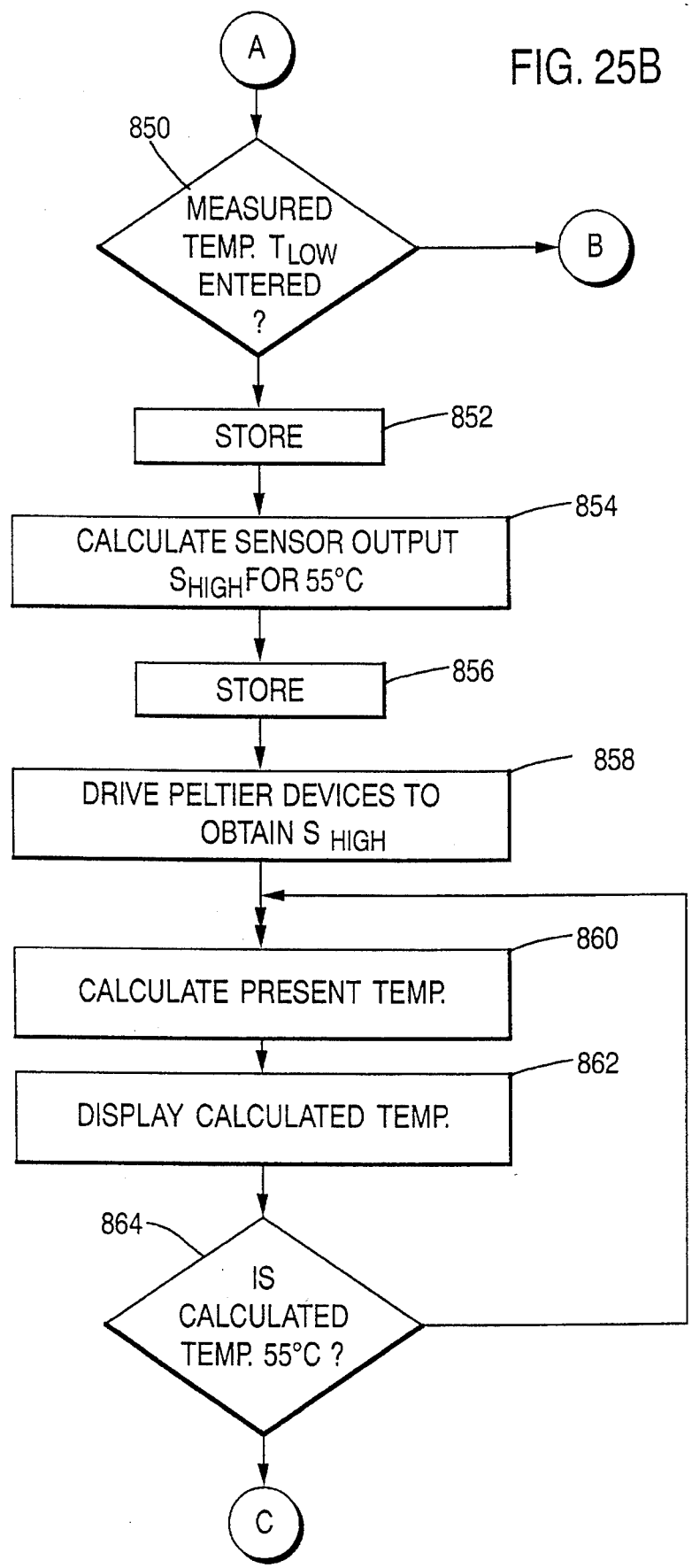
Figure 25C:
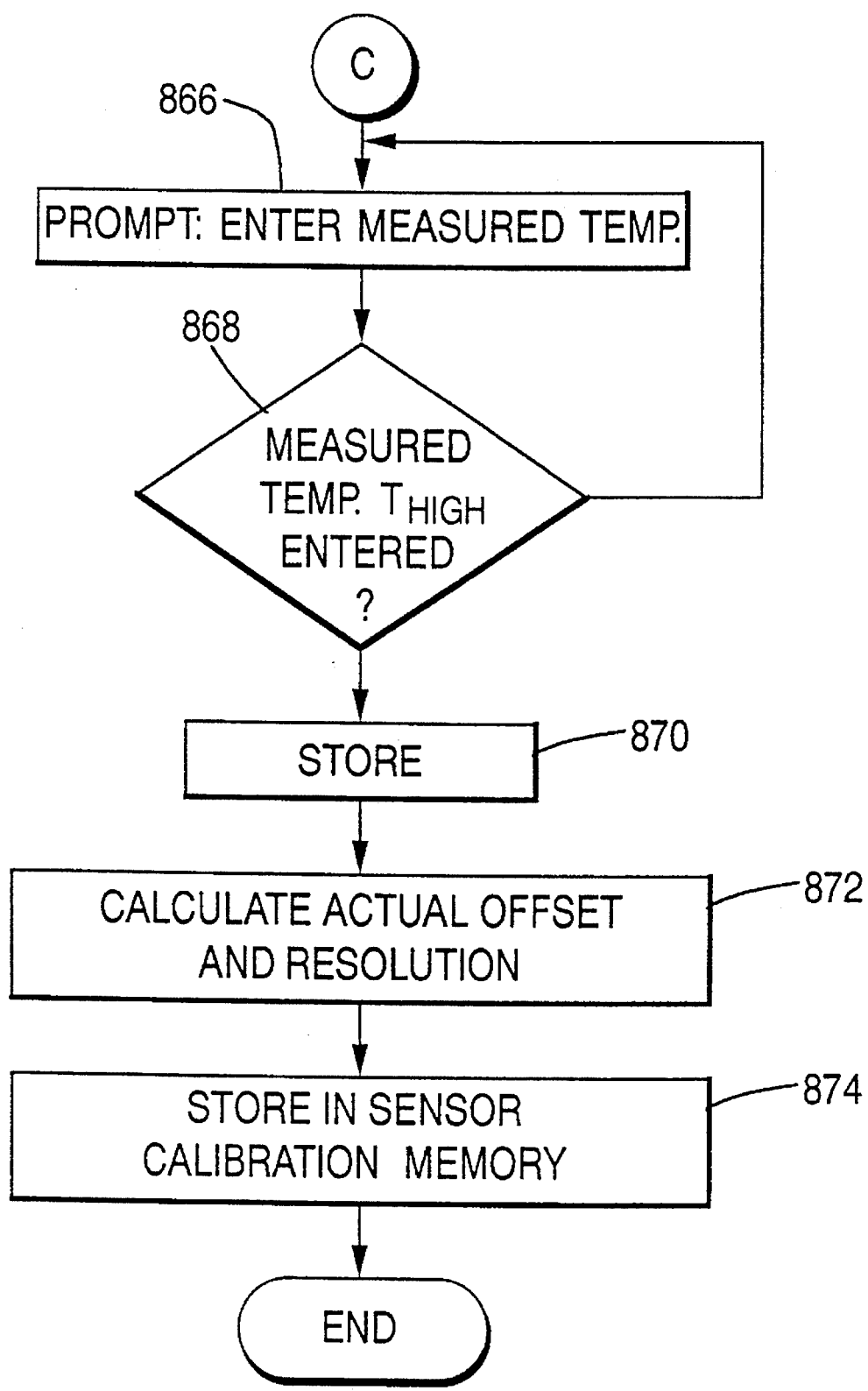
Figure 27A:
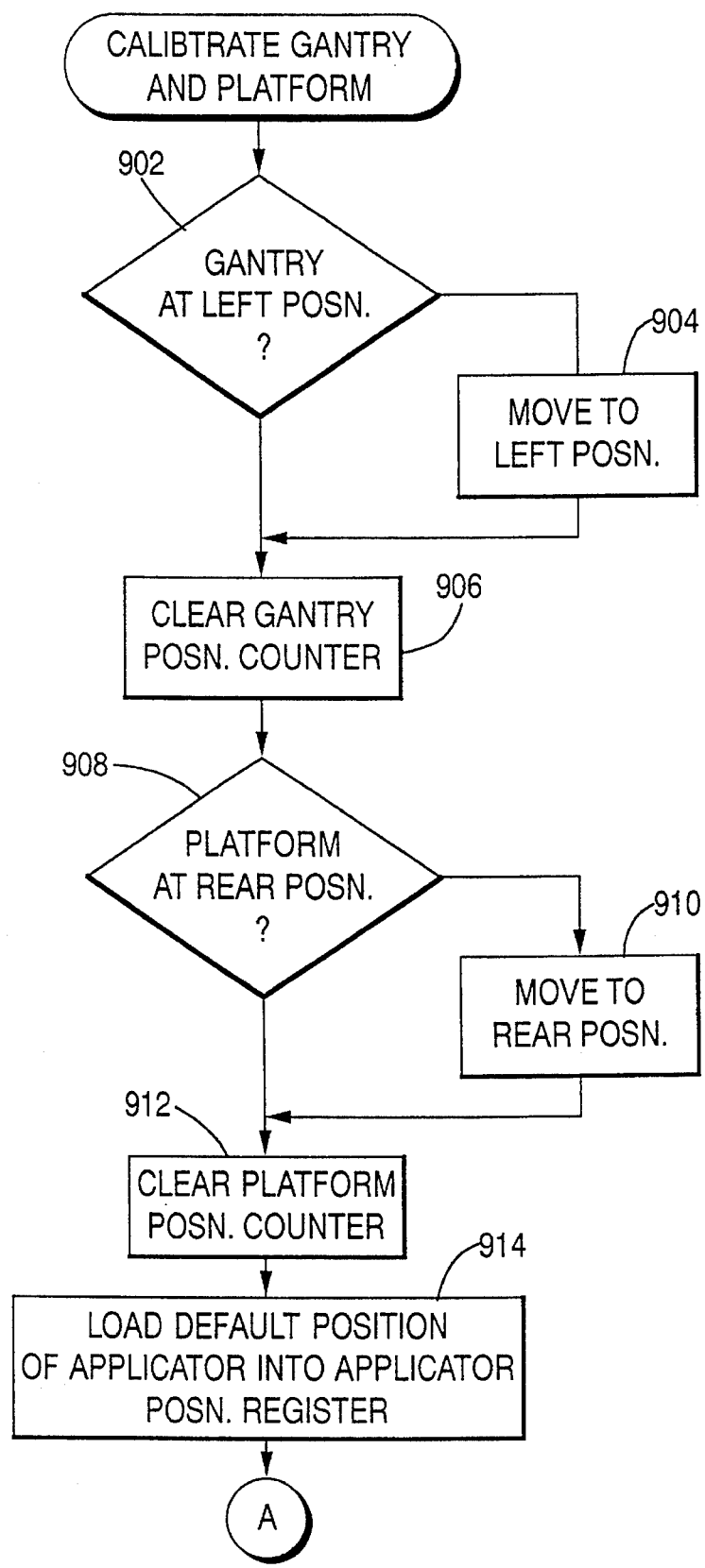
FIGS. 27A–27D illustrate a flow chart for a calibration procedure which uses the template of FIG. 26.
Figure 27B:
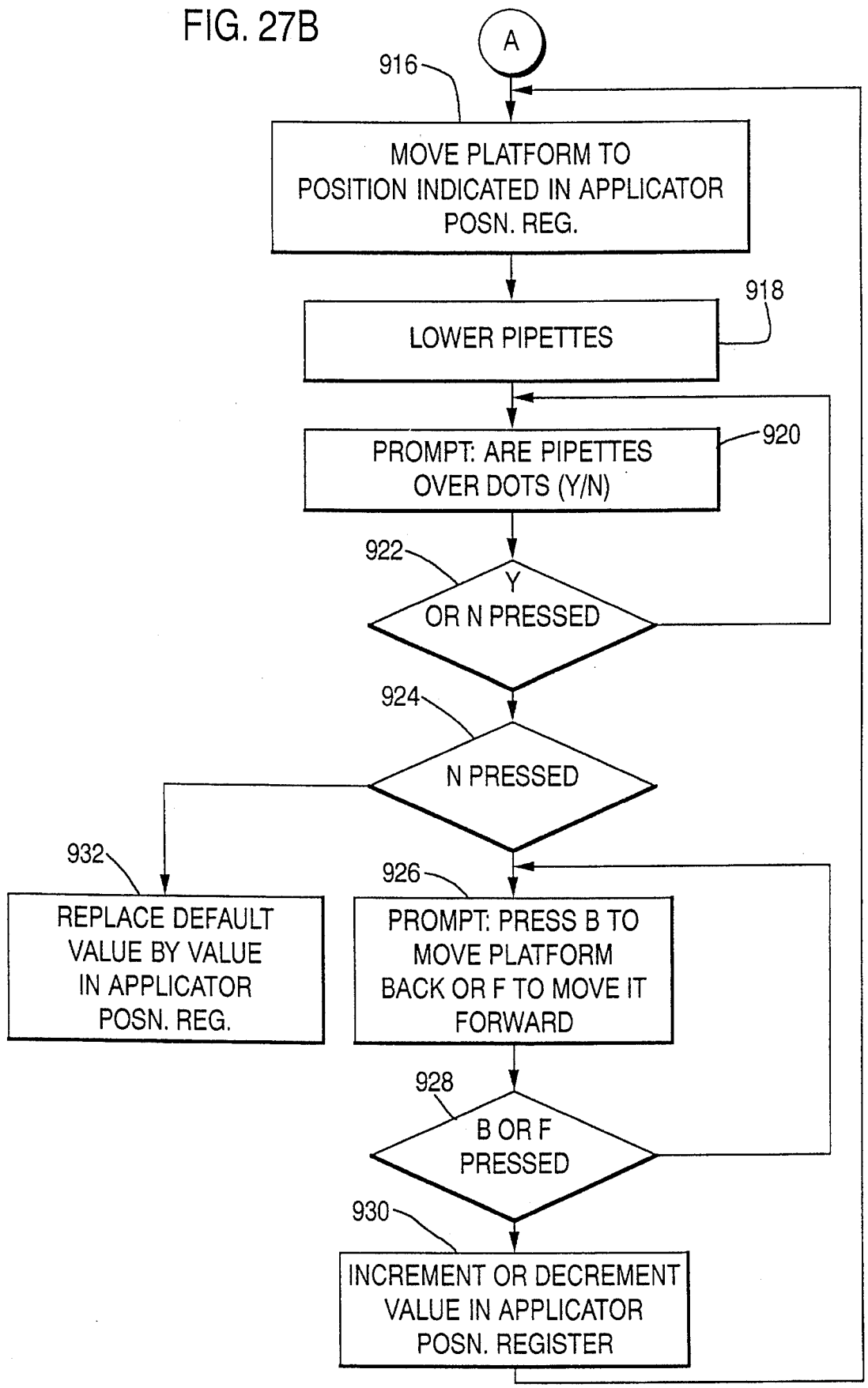
Figure 27C:
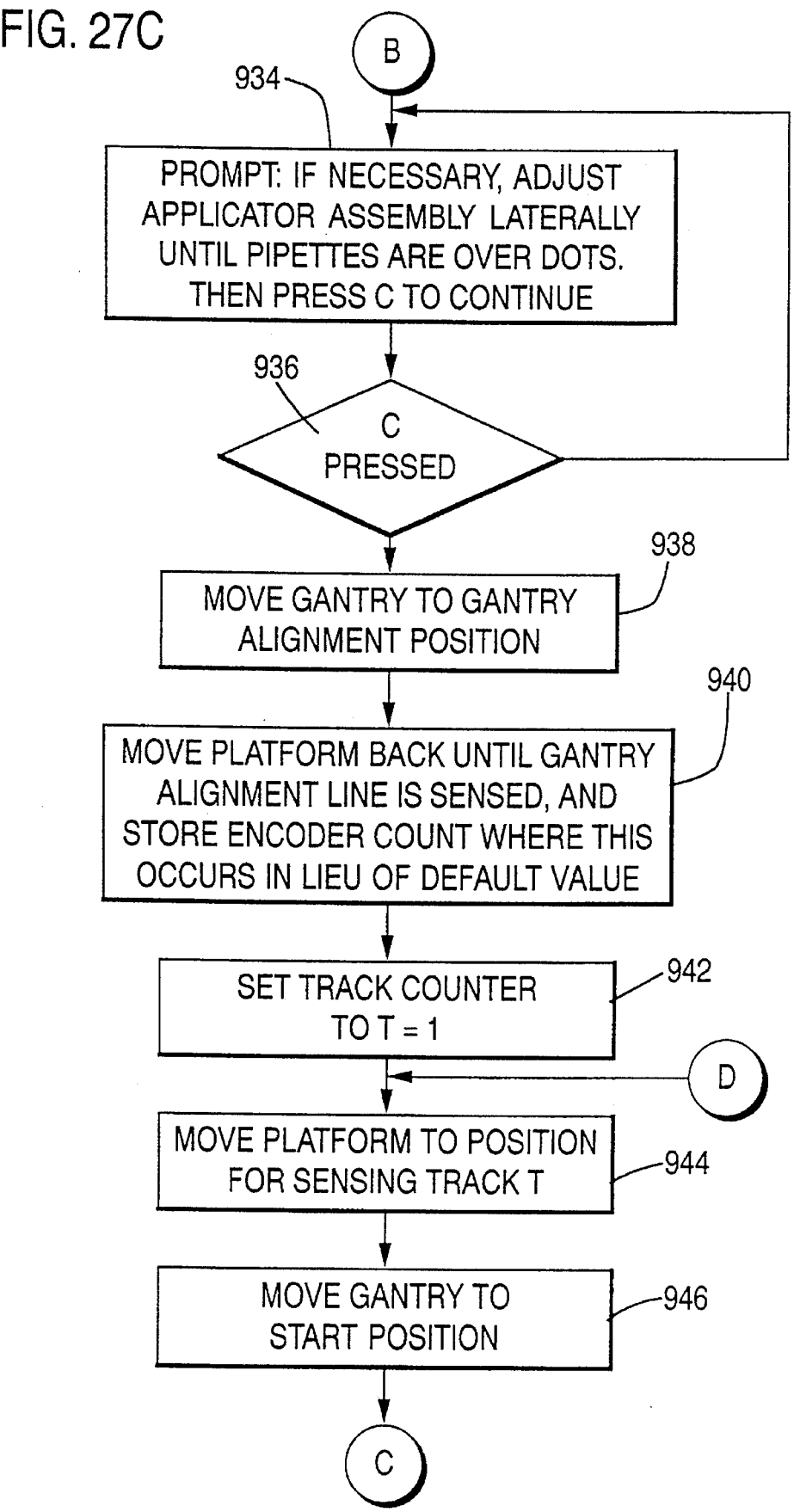
Figure 27D:
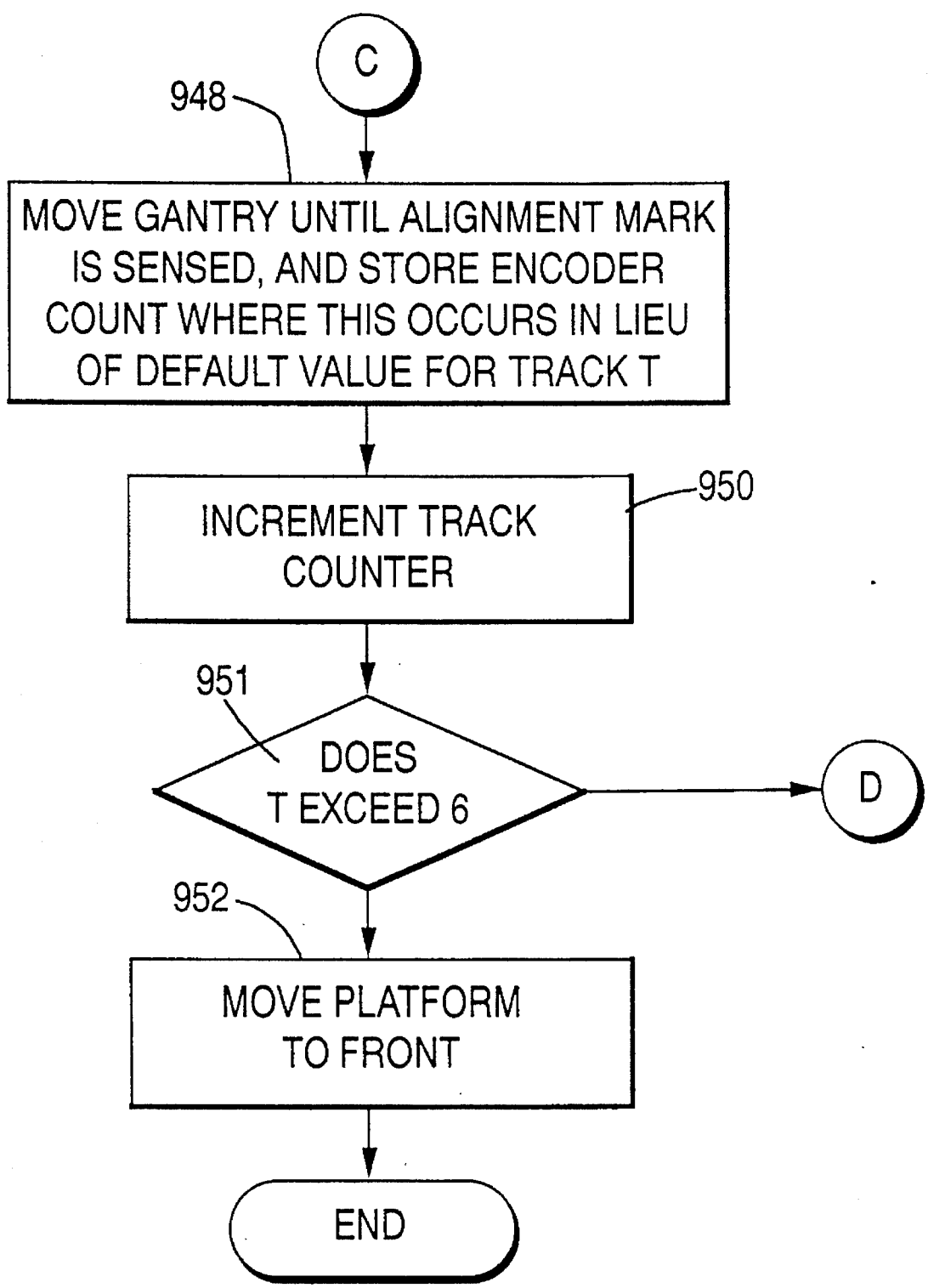
Figure 28A:
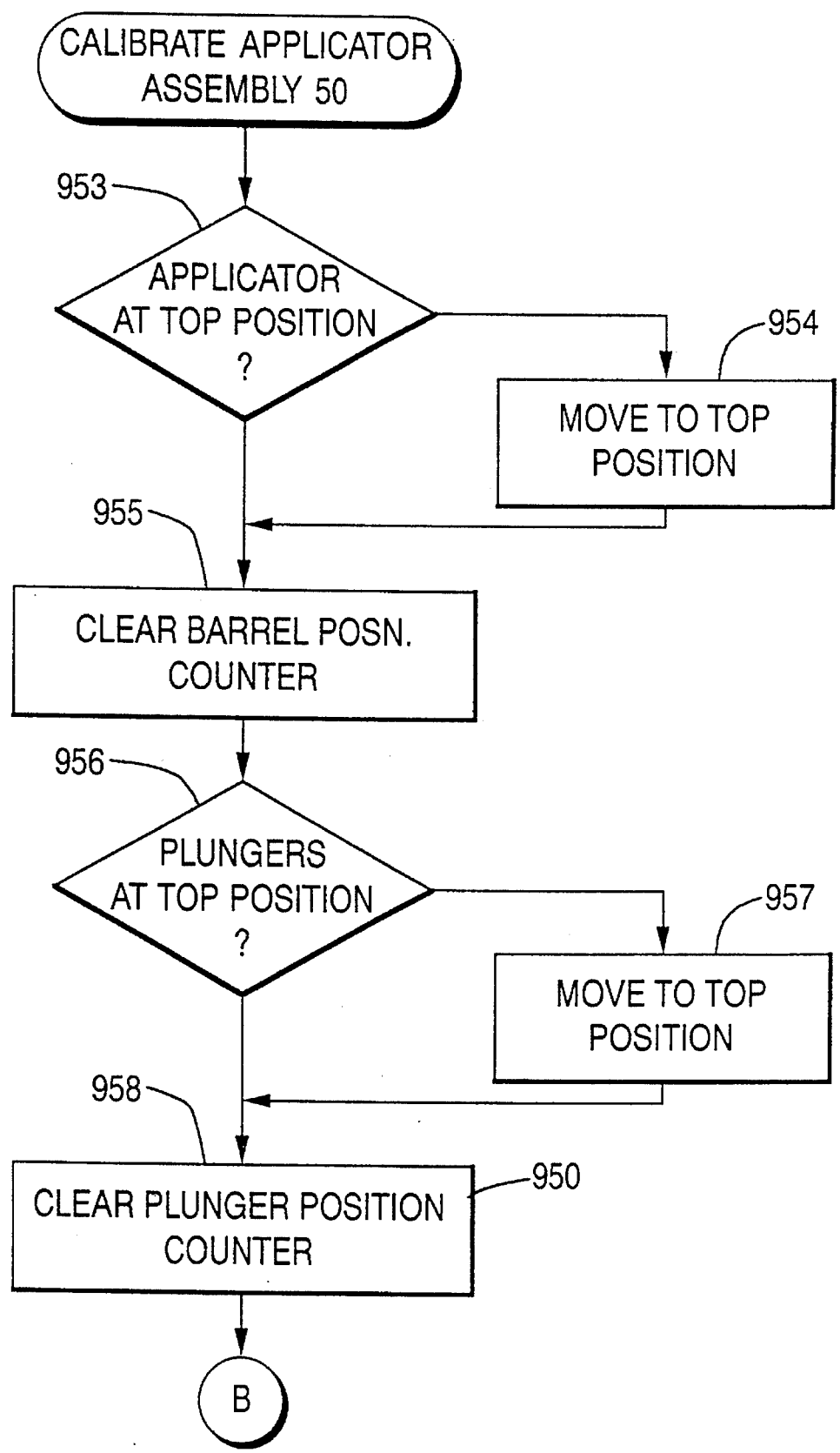
FIGS. 28A–28D illustrate a flow chart for an applicator calibration procedure.
Figure 28B:
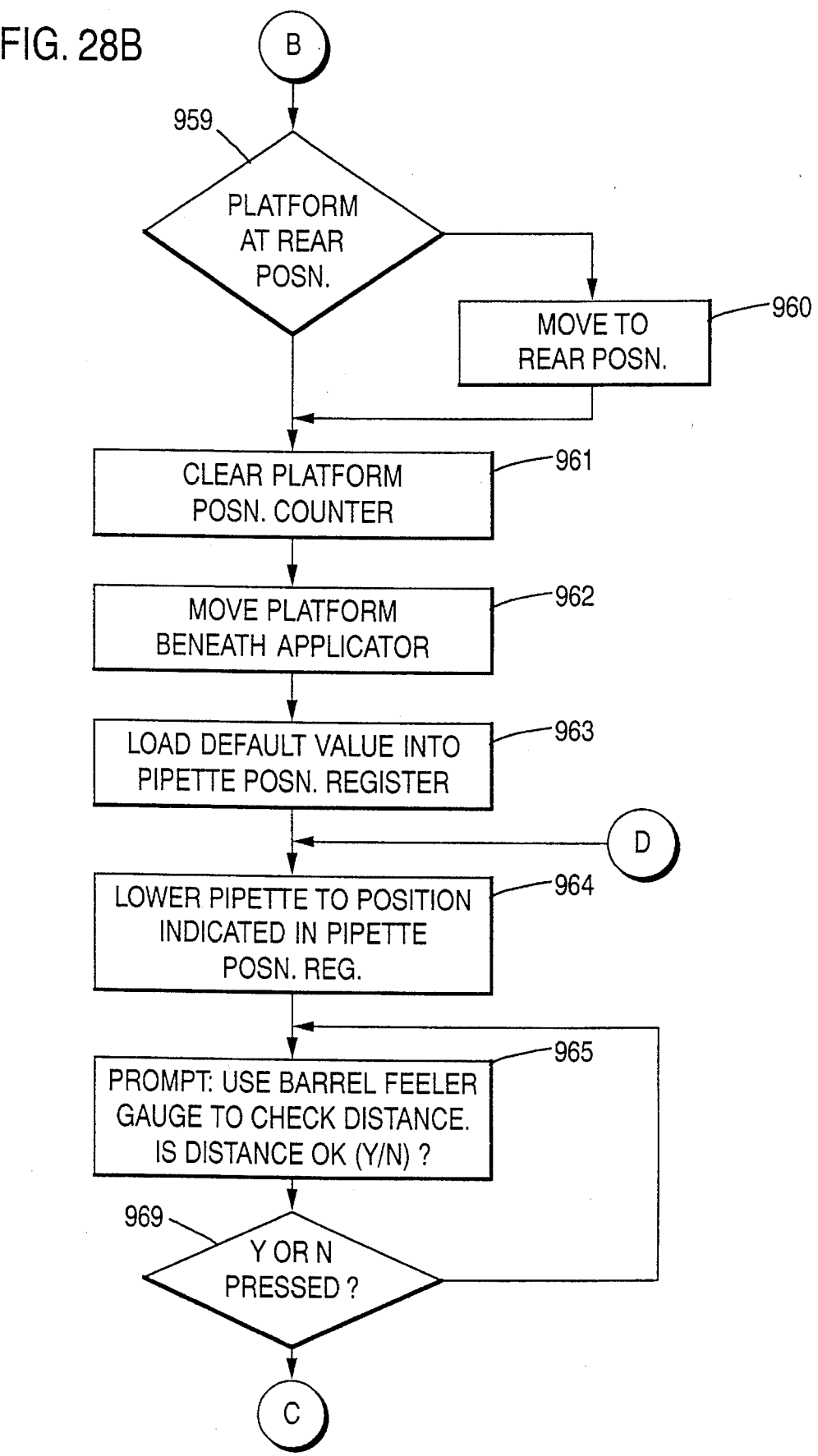
Figure 28C:
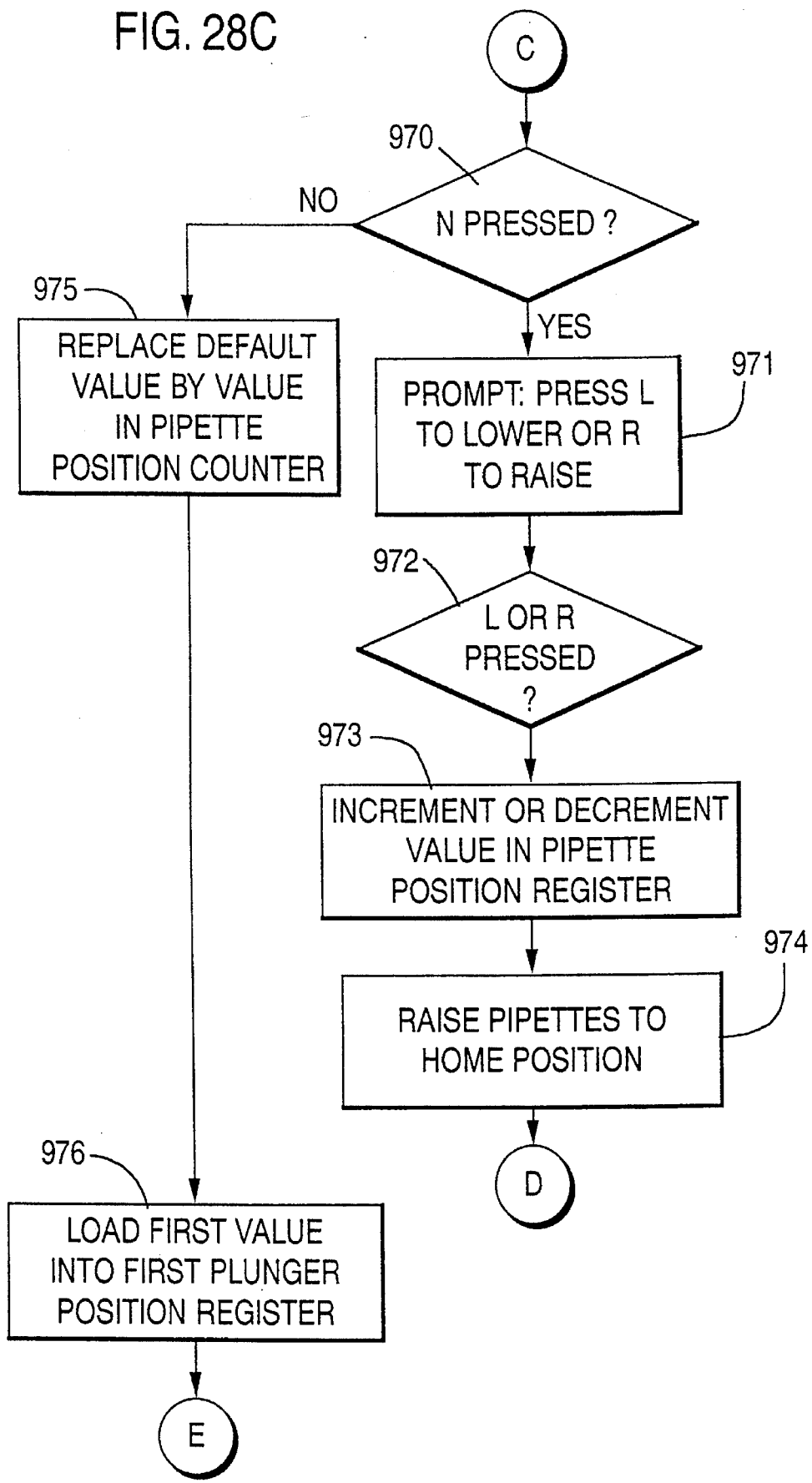
Figure 28D:
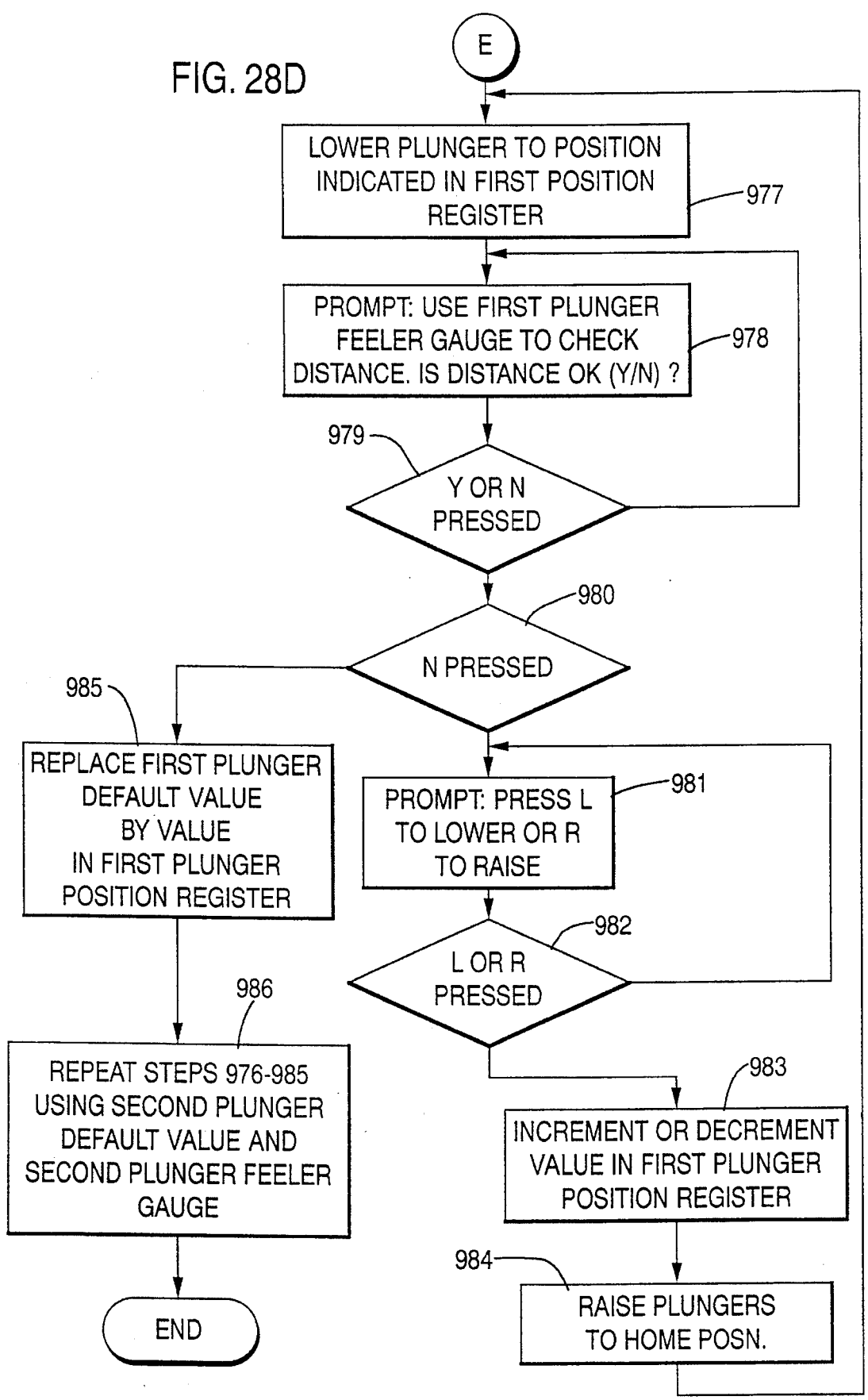

FIGS. 25A–25C illustrate the procedure for calibrating platform temperature sensor 192. An accurate electronic thermometer (not illustrated) with a probe is used during this procedure. Before the procedure begins, the probe is inserted on top of heat-transfer member 140 (FIG. 6).

Temperature sensor 192 is highly linear and its performance can be represented very accurately by the following linear Equation (4):

$$T = mS + b \qquad (4)$$

In the above equation, S represents the sensor output in millivolts. T represents the temperature. The term m represents the slope of the linear relationship, and will be called the "resolution." The term b represents the intercept with the ordinate axis, and will be called the "offset." In the calibration procedure described below the sensor output is measured at two different temperatures, yielding two linear equations (in the form of Equation 4) which can be solved for the resolution m and the offset b.

In step 834, default values for the resolution m and offset b are read from a sensor calibration register. These values are available from the manufacturer of the sensor or can easily be determined from other data provided by the manufacturer. Using the default values, the sensor output is calculated for a temperature of 10° C. using Equation 4. The calculated sensor output at 10° C. will be designated $S_{LOW}$. The calculated sensor output $S_{LOW}$ is stored in step 838, and in step 840 Peltier power supply 514 (see FIG. 19) drives Peltier devices 186 so that the output of platform temperature sensor 192 becomes $S_{LOW}$. Power supply 514 controls Peltier devices 186 in a closed loop servo control; Peltier devices 186 are driven until sensor 192 outputs the desired output and then the drive current is reduced until the output of sensor 192 departs slightly from the desired output, whereupon Peltier devices 186 are driven with more current. In this way the temperature is controlled by hardware within a narrow band.

The present temperature sensed by sensor 192 is calculated in step 842 using Equation 4 and the default resolution and offset. This is displayed on monitor 34 (see FIG. 1) in step 844. In step 846 a check is made to determine whether the calculated present temperature has reached 10° C. yet. After it has, the operator is asked to enter the measured temperature in step 848. Here, the measured temperature refers to the temperature sensed by the electronic thermometer. After the measured temperature has been entered (step 850), it is stored as $T_{LOW}$ in step 852. Next, a sensor output $S_{HIGH}$ is calculated for a temperature of 55° C. in step 854. The calculated output $S_{HIGH}$ is stored in step 856, and in step 858 Peltier devices 186 are driven by the hardware to achieve $S_{HIGH}$ as an output from sensor 192. The present temperature is calculated on the basis of the Equation 4 and the present output of sensor 192 in step 860, and this calculated temperature is displayed in step 862. A check is made in step 864 to determine whether the calculated temperature has reached 55° C. yet. When it has, the operator is asked in step 866 to enter the temperature measured using the electronic thermometer. After he has entered the measured temperature, step 868, it is stored as $T_{HIGH}$ in step 870. At this point two measured values of the temperature ($T_{LOW}$ and $T_{HIGH}$) and corresponding sensor outputs ($S_{LOW}$ and $S_{HIGH}$) are available, so the actual offset b and resolution m can be calculated in step 872. The actual values are then stored in the sensor calibration memory (step 874) in lieu of the previously-stored default resolution and offset.

Gantry temperature sensor 443 (see FIG. 19) is calibrated in the same way. The temperature probe of the electronic thermometer (not illustrated) is placed at air knife slot 338 and blower 340 is turned on during the calibration procedure. In this case, the low temperature selected for the calibration procedure is 35° C. and the high temperature is 63° C.

A similar procedure is employed to calibrate electrophoresis power supply 64. Instead of a sensor output signal, the variable in the linear equation is a command value from computer 62 which is used with the offset and resolution to determine a control signal for power supply 64. Initially, a voltmeter (not illustrated) is placed across the power supply. Default values for the voltage resolution and voltage offset are employed with a command value for a relatively low voltage (200 volts) and a command signal for a relatively high voltage (1200 volts) to compute low voltage and high voltage control signals for power supply 64. The measured values for the voltage can then be used to find the actual offset and resolution for use with any command values.

The current response of power supply 64 is calibrated in a similar manner. A milliammeter is connected across the output of power supply 64 in series with a 5490 ohm load resistor. Default values for the current resolution and current offset are then used to generate control values commanding a 20 milliamp output and a 91 milliamp output. The actual values obtained from the milliammeter can then be used, in conjunction with the control values supplied by computer 64 for calculating the control signal, to calculate the actual offset and resolution.

Figure 26:
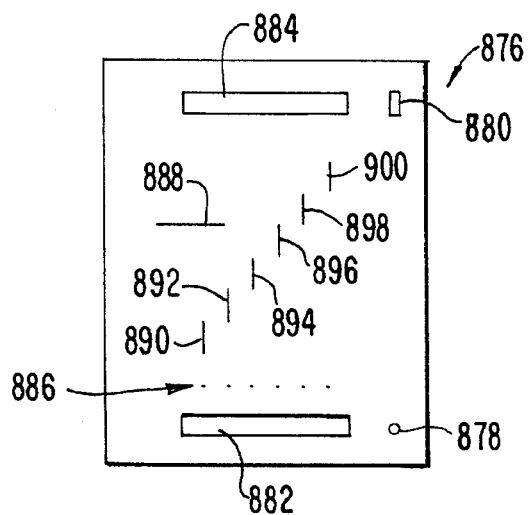
FIG. 26 is a top view of a calibration template.

The procedure for calibrating electrophoresis platform 48 and gantry assembly 56 will now be described with reference to FIGS. 16, 20, and 26 and the flow chart shown in FIGS. 27A–27D. The purpose in this calibration procedure is not to determine actual offset and resolution values for use with a linear equation, but instead to determine the total number of encoder pulses from home switches 392 and 396 when platform 48 and gantry assembly 56 are in predetermined positions.

A calibration template 876 is used when platform 48 and gantry assembly 56 are calibrated. It is a thin rectangular plate made of hard plastic, and has a hole 878, a slot 880, and rectangular openings 882 and 884 through it. Before the calibration procedure, template 876 is installed in recessed region 132 (see FIG. 5) of tray 130, with alignment peg 150 extending through hole 878 and with alignment peg 148 extending through slot 880. This precisely positions template 876 with respect to electrophoresis platform 48. Electrodes 146 extend through opening 882 in template 876 and electrodes 144 extend through opening 884.

The upper surface of template 876 is black, and absorbs ultraviolet radiation. Fluorescent alignment marks are provided on the black surface. These include six pipette alignment dots 886 which, as will be discussed, are used to determine the precise position of platform 48 when it is beneath pipettes 52, in terms of the total number of encoder pulses from home switch 392. The alignment marks additionally include a gantry alignment line 888. It is used to find the exact relationship of platform 48 with respect to slit 282, again in terms of the total number of encoder pulses from home switch 392. Gantry alignment line 888 is parallel to slit 282, and its vertical position (with respect to alignment hole 878, FIG. 26) on template 76 is known. Furthermore the distance moved by electrophoresis platform 48 between two pulses of position encoder 372 is known (such as one thousandth of an inch per pulse). By scanning the line 888, that is, by moving platform 48 along platform path 390 (FIG. 16) until slit 282 lies directly over line 888 and fluorescent light emitted by line 888 is detected by photomultiplier tube 312, the location of alignment pin 150 (FIG. 5) can be determined. All positions along platform path 390 for scanning, sample application, etc., are referenced to pin 150. Finally, the alignment marks include six track alignment lines 890, 892, 894, 896, 898, 890 one for each of the six tracks 388 (FIG. 16). They are used to determine the exact position of each track 388 in terms of the total number of pulses of encoder 366 when gantry assembly 56 moves from home switch 396 to a position in which slit 282 is directly above the respective track 388.

Turning now to the flow chart shown in FIGS. 27A–27D, a check is made in step 902 to determine whether gantry assembly 56 is located at home switch 396. If not, in step 904 it is moved to home switch 396 and a gantry position counter is cleared in step 906. A check is then made in step 908 to determine whether electrophoresis platform 48 is positioned at its home switch 392, and if not it is moved to that position in step 910. A platform position counter is cleared in step 912. Then a default position for applicator assembly 50 is loaded into an applicator position register in step 914, and platform 48 is moved until it reaches that position in step 916. Pipettes 52 (see FIG. 2) are then lowered to a position slightly above template 876 (step 918). The exact distance is not critical.

In step 920 the operator is asked whether pipettes 52 are positioned over pipette alignment dots 886. After the operator has responded (step 922), a check is made to determine whether the operator has entered "N," indicating that pipettes 52 are in front of or behind dots 886 and that adjustments are needed. If adjustments are needed, in step 926 the operator is asked to press keys on keyboard 32 to move platform 48 backward or forward, as needed. After the operator has complied (step 928) the content of applicator position register is decremented if platform 48 needs to be moved backward or incremented if it needs to be moved forward (step 930). Processing then returns to step 916. When pipettes 52 finally lie above dots 886, the value in the applicator position register is stored as a replacement for the default value in step 932.

Although not shown in detail, applicator assembly 50 is mounted so that it is laterally adjustable. In step 934 the operator is asked to mechanically adjust applicator assembly 50 if necessary to move the pipettes 52 laterally until they are over dots 886. After the operator has complied, step 936, gantry assembly 56 is moved to a gantry alignment position in step 938.

In the gantry alignment position, slit 282 is positioned to pass over gantry alignment line 888 when platform 48 is moved back. Since gantry alignment line 888 is relatively long it will be apparent that the gantry alignment position is not at all critical, and can be set with assurance that slit 828 will indeed encounter alignment line 888 even if there are considerable variations from one apparatus 30 to the next due to manufacturing tolerances. In step 940, electrophoresis platform 48 is moved towards its home switch 392 until slit 282 encounters the alignment line 888. The counted number of pulses of encoder 372 between home switch 392 and this position is stored in replacement of a default value that was stored when electrophoresis apparatus 30 was made. The program then proceeds to determining the exact positions of the tracks along gantry path 394, in terms of counted pulses emitted by encoder 366 from home switch 396.

In step 942, a track counter is set to one. Platform 48 is moved to a position for sensing track alignment line 890 in step 944. This is the approximate position where gantry path 394 traverses alignment line 890, and due to the length of line 890 it will be apparent that this position is not critical. Gantry assembly 56 is then moved to a gantry start position in step 946. This position, again not critical, is located at the right (with respect to FIG. 26) of track alignment lines 890–900. Gantry assembly 56 is then moved to the right in step 948 until it senses alignment line 898. It will be noted that the track alignment lines 890–900 overlap slightly at their ends, and it is desirable for an expected range of positions for each alignment line to be established in order to avoid the chance that an unintended alignment line might be detected if a particular apparatus 30 is produced at the extreme range of manufacturing tolerances. A value for the counted pulses from encoder 366 when the alignment line is detected is stored in lieu of a default value that was stored when assembly 30 was manufactured.

In step 950 the track counter is incremented, and in step 951 a check is made to determine whether any more tracks remain to be calibrated. When the sixth track has been calibrated, electrophoresis platform 48 is moved to the front of apparatus 30 (step 952) and the calibration procedure is finished.

Figure 29:
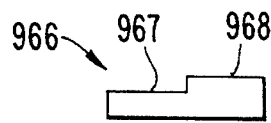
FIG. 29 is a side view of a go/no-go feeler gauge used during the applicator calibration procedure.

The procedure for calibrating applicator assembly 50 will now be described with reference to FIGS. 17, 20, and 29 and the flow chart shown in FIGS. 28A–28D.

In step 953 a check is made to determine whether plate 400 is at its top position, that is, whether home switch 416 is closed. If not, motor 406 is actuated to move plate 400 to its top position in step 954, and then a barrel position counter is cleared in step 955. In step 956 a check is made to determine whether plungers 440 are at their top position, that is, whether home switch 436 is closed. If not, motor 430 is actuated in step 957 to move them to their top position and a plunger position counter is cleared in step 958. A check is made in step 959 to determine whether electrophoresis platform 48 is in its rear position, and if not it is moved to the rear position in step 960, whereupon the platform position counter is cleared in step 961.

Platform 48 is moved beneath applicator assembly 50 in step 962. More particularly, platform 48 is moved so that pipettes 52 lie above the central region of protective film 142 (see FIG. 5). A default value that was stored when apparatus 30 was manufactured is then loaded into a pipette position register in step 963. If it turns out to be accurate, the default value will equal the counted pulses from encoder 408 when the lower tips of barrels 422 are located at a position greater than 0.027 inches and less than 0.037 inches above film 142. In step 964, motor 406 is actuated to move the pipettes 52 to the position indicated in the pipette position register. The operator is then asked, in step 965, to use a barrel feeler gauge to check the distance between the lower tips of barrels 422 and protective film 142. A barrel feeler gauge 966 is shown in FIG. 29. It is a go/no-go gauge having a portion 967 with a thickness of 0.027 inches and a portion 968 with a thickness of 0.037 inches. The operator checks to see whether portion 967 can slide underneath barrels 422 and portion 968 cannot. After the operator has used feeler gauge 966 and entered the result (step 969), a check is made at step 970 to determine whether adjustment is needed. If so, the operator is asked to press keys on keyboard 32 (see FIG. 1) to indicate whether barrels 422 are too high or too low. After he has complied, step 972, the value in the pipette position register is incremented or decremented as appropriate in step 973.

In step 974, motor 406 is actuated to raise plate 400 until home switch 916 is closed, and then processing returns to step 964 for further adjustment. Step 974 is not preparatory to clearing any counters; instead, the purpose of raising plate 400 is to ensure that calibration is accomplished by moving the elements in the same direction during a sequence of trials and refinements so as to avoid erratic results due to mechanical backlash.

When the distance has finally been adjusted so that portion 967 of feeler gauge 966 slides beneath barrels 422 but portion 968 does not (the "Yes" decision at step 970), the default value stored at the time of manufacture is replaced by the value in the pipette position counter (step 975). The program then proceeds to calibration of plungers 440 so that the amount of fluid they draw in or discharge can be determined with accuracy.

In step 976, a first plunger default value is loaded into a first plunger position register. If the default value turns out to be accurate, it will equal the counted pulses from encoder 431 when the lower ends of plungers 440 are even with the lower ends of barrels 422. This is the zero microliter position. In step 977, motor 430 is actuated to bring plungers 440 to the position indicated in the first barrel position register. The operator is then asked to use a first barrel position gauge to check the distance (step 978). The first barrel feeler gauge is a go/no-go gauge with a thick portion and a thin portion, like the barrel feeler gauge 966 shown in FIG. 29. The first plunger feeler gauge is used to determine the distance between bars 418 and 438 (the lengths of plungers 440 are selected such that the lower ends of the plungers would protrude below barrels 422 if bar 438 were moved into contact with bar 418). After the operator has used the feeler gauge (step 979), a decision is made as to whether adjustment is necessary (step 980). If so, in step 981 the operator is asked to use keyboard 32 to indicate whether plungers 440 should be lowered or raised (step 981). After the operator has done this (step 982), the content of the first plunger position register is incremented or decremented in accordance with the operator's entry (step 983) and motor 430 is actuated to raise yoke 424 until home switch 436 is closed (step 984). This is not a preliminary to clearing any position counters but, instead, ensures that plungers 440 are moved in the same direction during the calibration procedure to avoid inconsistent results due to mechanical backlash. After the plungers have been raised, processing returns to step 977.

After plungers 440 have been calibrated at the zero microliter position using the first plunger feeler gauge, the value in the first plunger position register is stored in lieu of the default value (step 985). Then, in step 986, steps 976 through 985 are repeated to calibrate a one microliter position using a second barrel feeler gauge, which is again used to determine the distance between bars 418 and 438.

It will be understood that the above description of the present invention is susceptible to various modifications, changes, and adaptations, and the same are intended to be comprehended within the meaning and range of equivalence of the appended claims.

What we claim is:

1. An apparatus for use with an electrophoresis plate which includes an electrophoresis medium layer to conduct assays of substances in liquid samples, comprising:

a first support for the electrophoresis plate;

first means for moving the first support along a first linear path;

applicator means disposed above the first linear path for depositing at least one liquid sample on the electrophoresis plate;

an optical detector;

a second support for the optical detector; and second means for moving the second support along a second linear path that passes over the first linear path and that is substantially perpendicular to the first linear path.

2. The apparatus of claim 1, wherein the first support comprises a platform having electrodes that contact the electrophoresis medium, and wherein the apparatus further comprises reagent pouring means disposed above the first linear path for pouring a reagent onto the electrophoresis plate.

3. The apparatus of claim 2, wherein the second support comprises a gantry assembly on which the optical detector is mounted, the gantry assembly additionally including air knife means, having an air knife slot, for blowing air toward the electrophoresis plate through the air knife slot.

4. The apparatus of claim 3, further comprising means for conveying air to the gantry assembly along an inlet air path, means for conveying air from the gantry assembly along an outlet air path, and means for selectively closing at least one of the air inlet path and the air outlet path.

5. The apparatus of claim 4, wherein the means for conveying air to the gantry assembly includes a metal air duct and a bellows connected to the air duct and the gantry assembly.

6. The apparatus of claim 4, wherein the means for selectively closing comprises an air duct valve having a slidably mounted plate, and a motor to move the plate between a valve-open position and a valve-closed position.

7. The apparatus of claim 3, wherein the gantry assembly further comprises means for heating the air blown through the air knife slot.

8. The apparatus of claim 3, wherein the gantry assembly further comprises a lamp housing, a lamp assembly having a portion that is configured to slide into the lamp housing and having at least one lamp mounted on the portion that is configured to slide into the lamp housing, and latch means for releasably latching the lamp assembly to the lamp housing.

9. The apparatus of claim 8, wherein the portion of the lamp assembly that is configured to slide into the lamp housing is generally U-shaped and has two parallel arms, wherein the lamp assembly has two lamps, one lamp being mounted on each arm, and wherein the gantry assembly further comprises a collimator that passes between the arms, the collimator conveying light to the optical detector.

10. The apparatus of claim 1, wherein the first support comprises a platform having electrodes that contact the electrophoresis medium layer, wherein the optical detector comprises a photomultiplier tube, wherein the second support comprises a gantry assembly on which the photomultiplier tube is mounted, wherein the gantry assembly additionally comprises an ultraviolet lamp, and wherein the apparatus further comprises electrophoresis power supply means for providing a voltage to the electrodes to cause movement of the samples along respective tracks that are parallel, the samples being separated into different fractions electrophoretically during movement along the tracks, and reagent pouring means disposed along the first linear path for pouring a reagent onto the electrophoresis plate to cause the fractions to emit fluorescent light when they are exposed to ultraviolet light from the lamp.

11. The apparatus of claim 10, further comprising a photomultiplier tube power supply for providing an anode voltage to the photomultiplier tube, means for controlling the first and second means so that the photomultiplier tube scans each track, and means for reducing the anode voltage automatically each time the output of the photomultiplier tube exceeds a predetermined value while the tracks are being scanned.

12. The apparatus of claim 10, further comprising an amplifier connected to the photomultiplier tube, the amplifier having an adjustable offset and an adjustable gain, means for controlling the first and second means so that the photomultiplier tube scans each track a first time and then a second time, means for detecting the lowest output of the amplifier and the highest output of the amplifier when each track is scanned the first time, means responsive to the lowest and highest outputs for adjusting the offset and resolution of the amplifier, and means for storing the output of the amplifier during the second scan of each track to provide stored scans.

13. The apparatus of claim 12, further comprising means for editing the stored scans to remove background noise, the means for editing including means for identifying the minima of each scan.

14. The apparatus of claim 1, further including means for calibrating the position of said first support.

15. The apparatus of claim 14 wherein said calibrating means includes;

a calibration template; and at least one position counter for determining the distance moved by the template.

16. The apparatus of claim 1, further including means for establishing an electric field across said electrophoresis medium layer.

17. The apparatus of claim 1, further including means for dispensing a reagent on said electrophoresis medium layer; and air knife means for spreading said reagent on said electrophoresis medium layer.

18. The apparatus of claim 1, further including:

a light source positioned to reflect light from the electrophoresis medium layer to the optical detector for scanning said electrophoresis medium layer.

19. The apparatus of claim 1, further including means for depositing a specimen on said electrophoresis medium layer.

* * * * *